(12) United States Patent
Peng et al.

(10) Patent No.: US 10,689,362 B2
(45) Date of Patent: Jun. 23, 2020

(54) QUINOXALINE COMPOUNDS AS TYPE III RECEPTOR TYROSINE KINASE INHIBITORS

(71) Applicant: Development Center for Biotechnology, Taipei (TW)

(72) Inventors: Shao-Zheng Peng, Taipei (TW); Chu-Bin Liao, Taipei (TW); Hung-Kai Chen, Taipei (TW); Chen-Hsuan Ho, Taipei (TW); Hung-Jyun Huang, Taipei (TW); Shian-Yi Chiou, Taipei (TW)

(73) Assignee: Development Center for Biotechnology, Taipei (TW)

(*) Notice: Subject to any disclaimer, the term of this patent is extended or adjusted under 35 U.S.C. 154(b) by 0 days.

(21) Appl. No.: 16/340,685

(22) PCT Filed: Oct. 9, 2017

(86) PCT No.: PCT/US2017/055809
§ 371 (c)(1),
(2) Date: Apr. 9, 2019

(87) PCT Pub. No.: WO2018/071348
PCT Pub. Date: Apr. 19, 2018

(65) Prior Publication Data
US 2019/0308949 A1    Oct. 10, 2019

Related U.S. Application Data

(60) Provisional application No. 62/406,328, filed on Oct. 10, 2016.

(51) Int. Cl.
| | | |
|---|---|---|
| A61K 31/44 | (2006.01) |
| A61K 31/498 | (2006.01) |
| A61P 35/00 | (2006.01) |
| C07D 241/40 | (2006.01) |
| C07D 241/44 | (2006.01) |
| C07D 401/06 | (2006.01) |
| C07D 401/12 | (2006.01) |
| C07D 241/52 | (2006.01) |
| C07D 401/14 | (2006.01) |
| C07D 413/04 | (2006.01) |
| C07D 413/14 | (2006.01) |
| C07D 401/04 | (2006.01) |
| C07D 413/12 | (2006.01) |
| C07D 403/04 | (2006.01) |
| C07D 405/12 | (2006.01) |
| C07D 409/12 | (2006.01) |
| C07D 403/12 | (2006.01) |
| C07D 403/14 | (2006.01) |

(52) U.S. Cl.
CPC ............ *C07D 401/12* (2013.01); *A61P 35/00* (2018.01); *C07D 241/44* (2013.01); *C07D 241/52* (2013.01); *C07D 401/04* (2013.01); *C07D 401/14* (2013.01); *C07D 403/04* (2013.01); *C07D 403/12* (2013.01); *C07D 403/14* (2013.01); *C07D 405/12* (2013.01); *C07D 409/12* (2013.01); *C07D 413/04* (2013.01); *C07D 413/12* (2013.01); *C07D 413/14* (2013.01)

(58) Field of Classification Search
CPC ....... A61K 31/44; A61K 31/498; A61P 35/00; C07D 241/40; C07D 241/44; C07D 401/06; C07D 401/12
See application file for complete search history.

(56) References Cited

U.S. PATENT DOCUMENTS

| | | | |
|---|---|---|---|
| 7,304,092 B1 * | 12/2007 | Austin | C07C 233/09 514/529 |
| 8,815,901 B2 * | 8/2014 | Furet | A61K 31/5377 514/311 |
| 2006/0135573 A1 * | 6/2006 | Galcera Contour | A61P 19/02 514/367 |
| 2009/0131461 A1 * | 5/2009 | Davidson | C07D 239/94 514/266.2 |
| 2015/0031669 A1 * | 1/2015 | Woodhead | C07D 401/14 514/210.18 |
| 2015/0057277 A1 * | 2/2015 | Zhu | A61K 45/06 514/234.8 |

* cited by examiner

*Primary Examiner* — Brenda L Coleman
(74) *Attorney, Agent, or Firm* — Liang Legal Group, PLLC

(57) ABSTRACT

A compound, capable of inhibiting kinases, for the treatments of diseases or disorders mediated by such kinases, has a structure of formula (I):

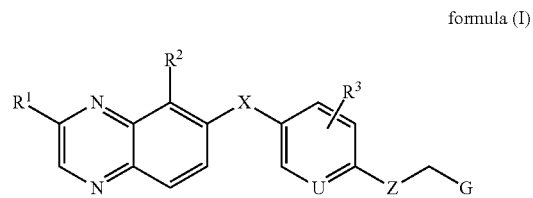

formula (I)

or a stereoisomer, a tautomer, a pharmaceutically acceptable salt thereof. The compound can be used in the treatments of diseases or conditions mediated by CSF-1R, c-KIT, FLT3, or PDGFR kinases. Such diseases or conditions may include cancers, autoimmune diseases, and bone resorptive diseases.

17 Claims, No Drawings

QUINOXALINE COMPOUNDS AS TYPE III RECEPTOR TYROSINE KINASE INHIBITORS

BACKGROUND OF INVENTION

Field of the Invention

The present invention relates to novel chemical compounds and methods for use in therapy, particularly to certain substituted quinoxaline compounds and their uses in the inhibition, regulation and/or modulation of type III receptor tyrosine kinases.

Background Art

Receptor tyrosine kinases (RTKs) are a sub-family of protein kinases. Type III RTKs, including PDGFRα, PDGFRβ, FLT3, c-KIT and CSF-1R, are implicated in various proliferative, inflammatory, and autoimmune diseases. Small molecule inhibitors of type III RTKs provide a rational approach to treatments of these diseases.

CSF-1R (M-CSFR) is a receptor for the macrophage colony stimulating factor (M-CSF or CSF-1). Binding of CSF-1 to its receptor activates signal transduction pathways, including PI3K/Akt and MAPK pathways, resulting in proliferation, survival, motility, and differentiation of cells of the monocyte/macrophage lineage. Elevated expression or activation of CSF-1R and/or its ligand have been found in a variety of cancers and elevated levels of M-CSF is associated with poor prognosis in certain cancers. M-CSF is one of several cytokines implicated in the recruitment of tumor-associated macrophages (TAMs) that contribute to tumor angiogenesis and tumor progression to metastasis. Activation of CSF-1R also leads to proliferation and differentiation of osteoclast precursors, thereby mediating the process of bone resorption. Inhibition of CSF-1R therefore provides treatments of cancers, especially cancer invasion, angiogenesis, metastasis, immunotolerance, and bone metastases. Because of its role in osteoclast biology, CSF-1R is also an important therapeutic target for osteoporosis, inflammatory arthritis, and other inflammatory bone erosion.

Receptor tyrosine kinase of the Platelet growth factor receptor (PDGFR) kinases are implicated in various proliferative disorders, such as gliomas, sarcomas, chronic myelomonocytic leukemia (CML), and gastrointestinal, making them potential targets for anti-tumor therapy.

FLT3 plays an important role in the proliferation and differentiation of hematopoietic stem cells. More than a dozen FLT3 inhibitors are being developed, some of which have shown promising clinical effects against AML. FLT3 receptor is also expressed in dendritic cell progenitors and inhibition of FLT3 down-regulates DC-mediated inflammatory and autoimmune responses.

c-KIT (or SCFR) is another member of the PDGFR family, and c-KIT mutations are associated with gastrointestinal stromal tumors (GIST), mast cell/myeloid leukemia, seminomas/dysgerminomas, and melanomas. Gleevec gained FDA-approval for c-KIT-mediated GIST in 2002.

Although various tyrosine kinase inhibitors are shown to be useful therapeutics, there is still a need for type III kinase inhibitors.

SUMMARY OF INVENTION

The present invention relates to novel inhibitors that inhibit kinases, such as CSF-1R, c-KIT, and/or PDGFR kinases, for the treatments of diseases or disorders mediated by such kinases, e.g., cancers, autoimmune diseases, and bone resorptive diseases.

Embodiments of the invention are based on unexpected findings that certain quinoxaline compounds can inhibit activities of type III RTKs (e.g., PDGFRα, PDGFRβ, FLT3, c-KIT and CSF-1R). The compounds are useful in medical treatments, pharmaceutical compositions and methods for modulating the activity of CSF-1R, FLT3, c-KIT, and/or PDGFR kinases, including wildtype and/or mutated forms of CSF-1R, FLT3, c-KIT, and/or PDGFR kinases. These properties allow these quinoxaline compounds to be used in treating protein tyrosine kinase-related diseases and/or conditions.

According to embodiments of this invention, a compound may have the general Formula I:

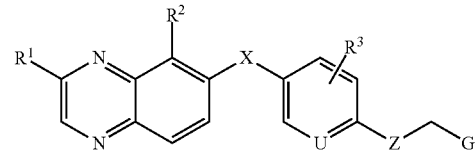

Formula (I)

a stereoisomer thereof, or a prodrug thereof, or a pharmaceutically acceptable salt thereof, wherein X, U, Z, G, $R^1$, $R^2$ and $R^3$ are as defined herein.

One aspect of the invention relates to pharmaceutical compositions comprising compounds of Formula I and a carrier, diluent or excipient.

Another aspect of the invention relates to a method of inhibiting type III receptor tyrosine kinases, such as PDGFR, CSF-1R, FLT-3 and/or c-KIT, in a mammal. A method in accordance with embodiments of the invention comprises: administering to said mammal in need thereof a therapeutically effective amount of a compound of Formula I or a pharmaceutically acceptable salt thereof.

Another aspect of the invention relates to a method for treating a disease or disorder selected from fibrosis, bone-related diseases, cancer, autoimmune disorders, inflammatory diseases, cardiovascular diseases, pain and burns in a mammal. A method in accordance with embodiments of the invention comprises administering to said mammal in need thereof a therapeutically effective amount of a compound of Formula I or a pharmaceutically acceptable salt thereof.

Another aspect of the invention relates to use of a compound of Formula I in the manufacture of a medicament for the treatment of a disease or disorder selected from fibrosis, bone-related diseases, cancer, autoimmune disorders, inflammatory diseases, cardiovascular diseases, pain and burns in a mammal.

Another aspect of the invention relates to a compound of Formula I, or a pharmaceutical composition thereof, for use in the treatment of a disease or disorder selected from fibrosis, bone-related diseases, cancer, autoimmune disorders, inflammatory diseases, cardiovascular diseases, pain and burns in a mammal.

Another aspect of the present invention relates to a pharmaceutical composition comprising a compound of this invention, a stereoisomer, tautomer, solvate, prodrug or a pharmaceutically acceptable salt thereof, and a pharmaceutically acceptable carrier or excipient.

Other aspects and advantages of the invention will be apparent from the following description and the appended claims.

DETAILED DESCRIPTION

While enumerated embodiments will be described, it will be understood that they are not intended to limit the invention to those embodiments. On the contrary, the invention is intended to cover all alternatives, modifications, and equivalents, which may be included within the scope of the present invention as defined by the claims.

The term "alkyl" refers to a straight or branched monovalent saturated hydrocarbon containing, unless otherwise stated, 1-20 carbon atoms. The numerical ranges in this description are intended to include any number(s) in the defined range, as if the individual numbers have been separately disclosed. For example, an alkyl group of 1-20 carbons would include $C_1$, $C_2$, ... $C_{20}$, as well as $C_1$-$C_{20}$, $C_1$-$C_{15}$, $C_1$-$C_{10}$, $C_1$-$C_6$, $C_1$-$C_4$, etc. Examples of alkyl include methyl, ethyl, n-propyl, i-propyl, n-butyl, i-butyl, and t-butyl.

The term "alkenyl" refers to a straight or branched monovalent hydrocarbon containing 2-20 carbon atoms (e.g., $C_2$-$C_{10}$) and one or more double bonds. Examples of alkenyl include ethenyl, propenyl, allyl, and 1,4-butadienyl.

The term "alkynyl" refers to a straight or branched monovalent hydrocarbon containing 2-20 carbon atoms (e.g., $C_2$-$C_{10}$) and one or more triple bonds. Examples of alkynyl include ethynyl, 1-propynyl, 1- and 2-butynyl, and 1-methyl-2-butynyl.

The term "alkoxy" refers to an —O-alkyl radical, wherein the alkyl portion is as defined above. Examples of alkoxy include methoxy, ethoxy, n-propoxy, i-propoxy, n-butoxy, i-butoxy, s-butoxy, and t-butoxy.

The term "acyloxy" refers to an —O—C(O)—R radical in which R can be H, alkyl, alkenyl, alkynyl, cycloalkyl, cycloalkenyl, heterocycloalkyl, heterocycloalkenyl, aryl, or heteroaryl as defined herein.

The term "amino" refers to $NH_2$. The term "alkylamino" refers to an —N(R)-alkyl radical, in which "alkyl" is as defined above and R can be H, alkyl, alkenyl, alkynyl, cycloalkyl, cycloalkenyl, heterocycloalkyl, heterocycloalkenyl, aryl, or heteroaryl.

The term "cycloalkyl" refers to a monovalent saturated hydrocarbon ring system having 3 to 30 carbon atoms (e.g., $C_3$-$C_6$ or $C_3$-$C_{12}$). Examples of cycloalkyl include cyclopropyl, cyclobutyl, cyclopentyl, cyclohexyl, cycloheptyl, cyclooctyl, and adamantanyl.

The term "cycloalkenyl" refers to a monovalent non-aromatic hydrocarbon ring system having 3 to 30 carbons (e.g., $C_3$-$C_6$ or $C_3$-$C_{12}$) and one or more double bonds. Examples include cyclopentenyl, cyclohexenyl, and cycloheptenyl.

The term "heterocycloalkyl" refers to a monovalent non-aromatic 5-8 membered monocyclic, 8-12 membered bicyclic, or 11-14 membered tricyclic ring system having one or more heteroatoms (such as O, N, S, or Se). Examples of heterocycloalkyl groups include piperazinyl, pyrrolidinyl, piperidinyl, dioxanyl, morpholinyl, and tetrahydrofuranyl.

The term "heterocycloalkenyl" refers to a monovalent nonaromatic 5-8 membered monocyclic, 8-12 membered bicyclic, or 11-14 membered tricyclic ring system having one or more heteroatoms (such as O, N, S, or Se) and one or more double bonds.

The term "aryl" refers to a monovalent 6-carbon monocyclic, 10-carbon bicyclic, or 14-carbon tricyclic aromatic ring system. Examples of aryl groups include phenyl, naphthyl, and anthracenyl.

The term "aryloxyl" refers to an —O-aryl, wherein "aryl" is as defined above. The term "arylamino" refers to an —N(R)-aryl, wherein "aryl" is as defined above and R can be H, alkyl, alkenyl, alkynyl, cycloalkyl, cycloalkenyl, heterocycloalkyl, heterocycloalkenyl, aryl, or heteroaryl. The term "heteroaryl" refers to a monovalent aromatic 5-8 membered monocyclic, 8-12 membered bicyclic, or 11-14 membered tricyclic ring system having one or more heteroatoms (such as O, N, S, or Se). Examples of heteroaryl groups include pyridyl, furyl, imidazolyl, benzimidazolyl, pyrimidinyl, thienyl, quinolinyl, indolyl, thiazolyl, pyrrolyl, isoquinolinyl, purinyl, oxazolyl, pyrazolyl, and carbazolyl. In all these terms, "aryl" portion is as defined above.

The above-described alkyl, alkenyl, alkynyl, cycloalkyl, heterocycloalkyl, cycloalkenyl, heterocycloalkenyl, amino, alkylamino, arylamino, alkoxy, aryloxy, aryl, and heteroaryl may be substituted or unsubstituted moieties. Possible substituents on amino, alkylamino, arylamino, alkoxy, aryloxy, cycloalkyl, heterocycloalkyl, cycloalkenyl, heterocycloalkenyl, aryl, and heteroaryl include $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, arylamino, hydroxy, halo, oxo (O=), thioxo (S=), thio, $C_1$-$C_{10}$ alkylthio, arylthio, $C_1$-$C_{10}$ alkylsulfonyl, arylsulfonyl, acylamino, aminoacyl, aminothioacyl, amidino, mercapto, amido, thioureido, thiocyanato, sulfonamido, guanidine, ureido, cyano, nitro, acyl, thioacyl, acyloxy, carbamido, carbamyl (—C(O)$NH_2$), carboxyl (—COOH), and carboxylic ester. Possible substituents on alkyl, alkenyl, or alkynyl include all of the above-recited substituents except $C_1$-$C_{10}$ alkyl. Cycloalkyl, cycloalkenyl, heterocycloalkyl, heterocycloalkenyl, aryl, and heteroaryl can also be fused with each other.

Provided herein are compounds, and pharmaceutical compositions thereof, that are useful in the treatment or prevention of diseases, conditions and/or disorders modulated/mediated by (or associated with) a protein tyrosine kinase, such as CSF-1R.

Embodiments of the invention relate to compounds of Formula I:

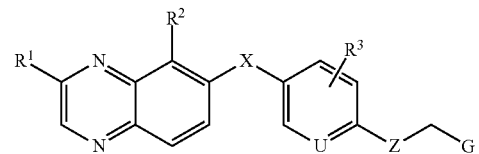

Formula (I)

or a stereoisomer, a tautomer, a pharmaceutically acceptable salt thereof,
wherein:
X is selected from the group consisting of $CR^4R^5$, $NR^6$, O and S;
Z is selected from the group consisting of —$NR^7$— and —O—;
U is N or $CR^8$;
G is selected from the group consisting of aryl, heteroaryl, cycloalkyl, heterocycle, alkene and alkyne, each of which is optionally substituted with hydrogen, deuterium, halogen, cyano, $C_1$-$C_6$ alkoxy, $C_1$-$C_6$ alkthiol, $C_1$-$C_6$ alkylamino, $C_1$-$C_6$ dialkylamino, and $C_3$-$C_6$ cycloalkyl.

$R^1$ is selected from the group consisting of hydrogen, deuterium, halogen, amino, hydroxyl, $C_1$-$C_6$ alkyl, $C_2$-$C_6$ alkenyl, $C_2$-$C_6$ alkynyl, $C_1$-$C_6$ alkylamino $C_1$-$C_6$ alkyl, $C_1$-$C_6$ dialkylamino $C_1$-$C_6$ alkyl, $C_1$-$C_6$ alkoxy $C_1$-$C_6$ alkyl, $C_3$-$C_6$ cycloalkyl, $C_3$-$C_6$ cycloalkenyl, $C_1$-$C_6$ alkylamino, $C_1$-$C_6$ dialkylamino, $C_3$-$C_6$ cycloalkylamino, $C_1$-$C_6$-alkoxy, $C_3$-$C_6$ cycloalkoxy, aryl, a 3-to-6 membered heterocyclyl, and a 5-to-6 membered heteroaryl, wherein the alkylamino, dialkylamino, alkoxy, alkyl, alkenyl, alkynyl, cycloakyl, cycloalkenyl, cycloalkylamino, cycloalkoxy, heterocyclyl, aryl and heteroaryl are optionally substituted with halogen, amino, hydroxyl, cyano, nitro, $C_1$-$C_6$ alkyl, $C_1$-$C_6$ alkoxy, and cyclopropyl;

$R^2$ is selected from the group consisting of hydrogen, deuterium, halogen, nitro, cyano, trifluoromethyl, $C_1$-$C_6$ alkylamino, $C_1$-$C_6$ dialkylamino, $C_1$-$C_6$ alkoxy, carboxylic acid, $C_1$-$C_6$ alkyl carbonyl, $C_2$-$C_6$ alkenyl carbonyl, $C_1$-$C_6$ alkoxy carbonyl, amino carbonyl, $C_1$-$C_6$ alkylamino carbonyl, and $C_1$-$C_6$ dialkylamino carbonyl;

$R^3$ is selected from the group consisting of hydrogen, deuterium, halogen, hydroxyl, amino, cyano, trifluoromethyl, $C_1$-$C_6$ alkyl, $C_1$-$C_6$ alkoxy, $C_1$-$C_6$ alkylamino, and $C_1$-$C_6$ dialkylamino;

$R^4$ is selected from the group consisting of hydrogen, deuterium, halogen, hydroxyl, amino, $C_1$-$C_6$ alkyl, $C_1$-$C_6$ haloalkyl, $C_1$-$C_6$ alkoxy, and aryl;

$R^5$ is selected from the group consisting of hydrogen, deuterium, $C_1$-$C_6$ alkyl, and $C_1$-$C_6$ haloalkyl;

$R^6$ is selected from the group consisting of hydrogen, $C_1$-$C_6$ alkyl, and $C_1$-$C_6$ haloalkyl;

$R^7$ is selected from the group consisting of hydrogen, $C_1$-$C_6$ alkyl, and $C_1$-$C_6$ haloalkyl; and $R^8$ is selected from the group consisting of hydrogen, deuterium, halogen, hydroxyl, amino, cyano, trifluoromethyl, $C_1$-$C_6$ alkyl, $C_1$-$C_6$ alkoxy, $C_1$-$C_6$ alkylamino, and $C_1$-$C_6$ dialkylamino.

In accordance with some embodiments of the invention, a compound of Formula 1 may comprise: G selected from:

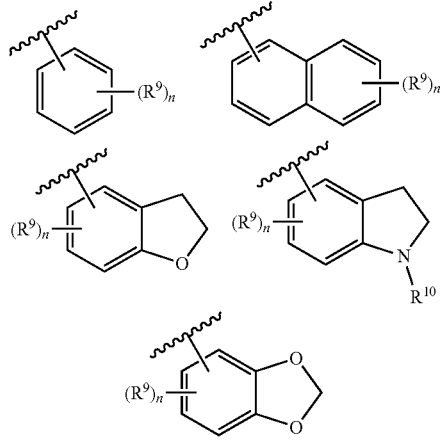

wherein $R^9$ is selected from the group consisting of hydrogen, deuterium, halogen, nitro, cyano, trifluoromethyl, trifluoromethoxy, $C_1$-$C_6$ alkyl, $C_1$-$C_6$ haloalkyl, $C_1$-$C_6$ alkylamino$C_1$-$C_6$ alkyl, $C_1$-$C_6$ dialkylamino$C_1$-$C_6$ alkyl, $C_1$-$C_6$ alkylamino, $C_1$-$C_6$-alkoxy$C_1$-$C_6$ alkyl, $C_1$-$C_6$ dialkylamino, $C_1$-$C_6$ alkoxy, carboxylic acid, carbonyl $C_1$-$C_6$ alkoxy, carbonyl $C_1$-$C_6$ alkylamino, and carbonyl $C_1$-$C_6$ dialkylamino; and $R^{10}$ is selected from the group consisting of hydrogen, $C_1$-$C_6$ alkyl, and $C_1$-$C_6$ haloalkyl.

In accordance with some embodiments of the invention, a compound of Formula 1 may comprise: G selected from:

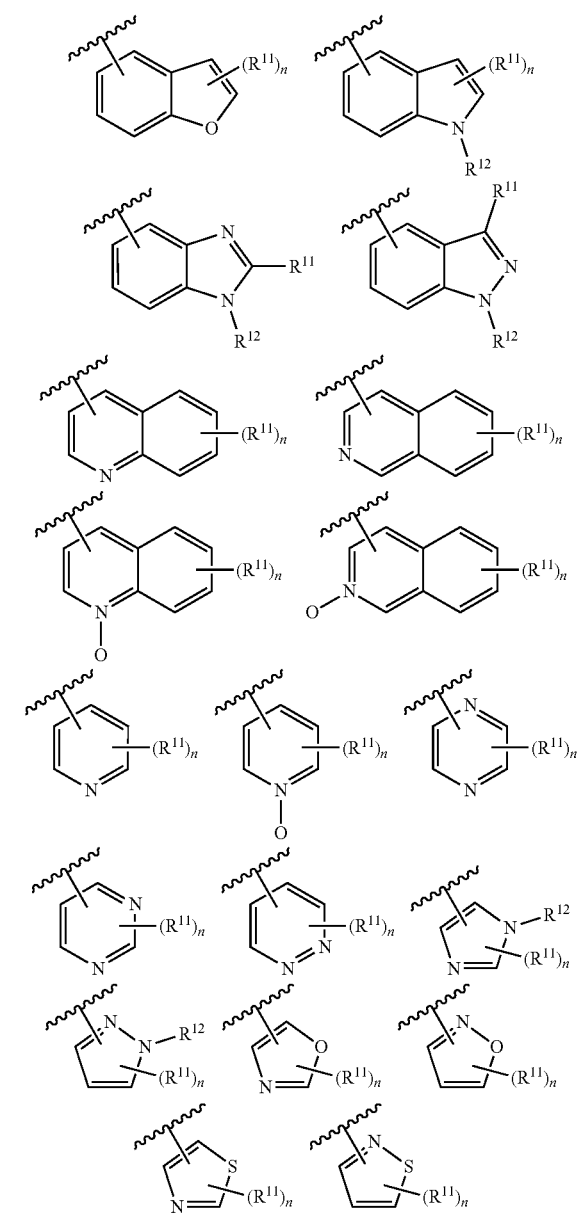

wherein $R^1$ is selected from the group consisting of hydrogen, deuterium, halogen, nitro, cyano, trifluoromethyl, $C_1$-$C_6$ alkyl, $C_1$-$C_6$ haloalkyl, $C_1$-$C_6$ alkylamino, $C_1$-$C_6$ dialkylamino, $C_1$-$C_6$ alkoxy, carboxylic acid, carbonyl $C_1$-$C_6$ alkoxy, carbonyl $C_1$-$C_6$ alkylamino, and carbonyl $C_1$-$C_6$ dialkylamino; and $R^{12}$ is selected from the group consisting of hydrogen, $C_1$-$C_6$ alkyl, and $C_1$-$C_6$ haloalkyl.

In accordance with some embodiments of the invention, a compound of Formula 1 may comprise: G selected from:

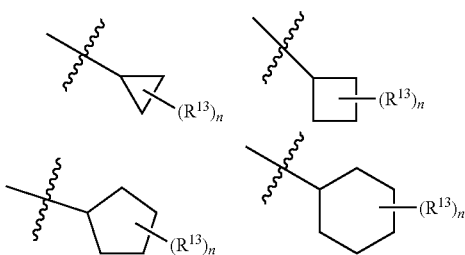

wherein
R$^{13}$ is selected from the group consisting of hydrogen, deuterium, halogen, nitro, cyano, trifluoromethyl, C$_1$-C$_6$ alkyl, C$_1$-C$_6$ haloalkyl, C$_1$-C$_6$ alkylamino, C$_1$-C$_6$ dialkylamino, C$_1$-C$_6$ alkoxy, carboxylic acid, C$_1$-C$_6$ alkoxycarbonyl, C$_1$-C$_6$ alkylaminocarbonyl, and C$_1$-C$_6$ dialkylaminocarbonyl.

In accordance with some embodiments of the invention, a compound of Formula 1 may comprise: G selected from:

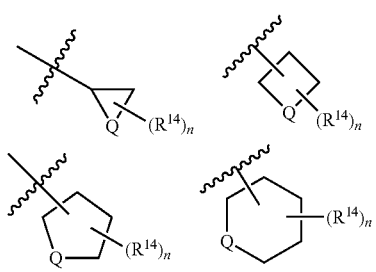

wherein
R$^{14}$ is selected from the group consisting of hydrogen, deuterium, halogen, nitro, cyano, trifluoromethyl, C$_1$-C$_6$ alkyl, C$_1$-C$_6$ haloalkyl, C$_1$-C$_6$ alkylamino, C$_1$-C$_6$ dialkylamino, C$_1$-C$_6$ alkoxy, carboxylic acid, C$_1$-C$_6$ alkoxycarbonyl, C$_1$-C$_6$ alkylaminocarbonyl, and C$_1$-C$_6$ dialkylaminocarbonyl; and Q is selected from NR$^{15}$, O, and S, wherein R$^{15}$ is selected from the group consisting of hydrogen, C$_1$-C$_6$ alkyl, and C$_1$-C$_6$ haloalkyl.

In accordance with some embodiments of the invention, a compound of Formula 1 may comprise: G selected from:

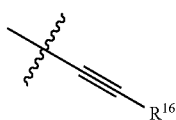

wherein
R$^{16}$ is selected from the group consisting of hydrogen, deuterium, C$_1$-C$_6$ alkyl, C$_1$-C$_6$ haloalkyl, 3-to-6 membered heterocyclyl, 5-to-6 membered heteroaryl, C$_1$-C$_6$-alkoxycarbonyl, C$_1$-C$_6$ alkylaminocarbonyl, and C$_1$-C$_6$ dialkylaminocarbonyl.

One skilled in the art would appreciate that in the above formula (I), all possible combinations or permutations of different substituents are within the scope of the invention. These compounds can be prepared using readily available materials/reagents and known chemical reactions. Based on common knowledge in the art and the teaching in this disclosure, one skilled in the art should be able to prepare and use these compounds without undue experimentation.

The following reaction schemes, Reaction Scheme 1 through Reaction Scheme 15, provide exemplary procedures that can be used to prepare the compounds of Formula (I). However, one skilled in the art would appreciate that these examples are for illustration only and that modifications or variations are possible without departing from the scope of the invention. A quinoxaline compound synthesized in accordance with embodiments of the invention may be purified with any known techniques, such as by flash column chromatography, high performance liquid chromatography, crystallization, or any other suitable methods.

Reaction Scheme 1.

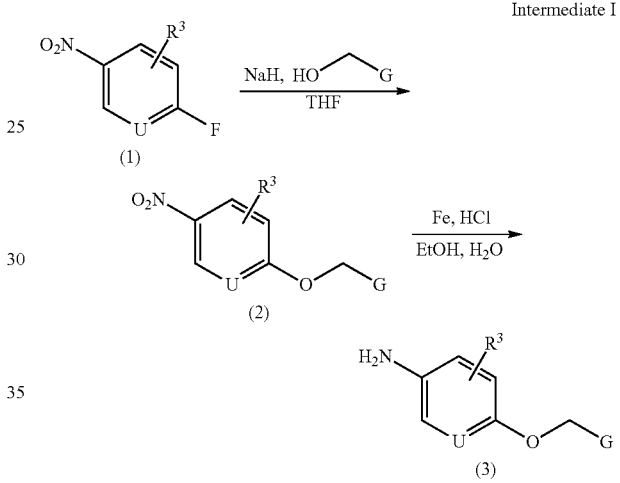

To a solution of compound 1 (1.0 eq) and alcohol (G-CH$_2$—OH, 1.0 eq) in tetrahydrofuran (0.2M) was added Sodium hydride (1.1 eq) and stirred at 0° C. After 3.0 hours, the reaction was followed by TLC and quenched with saturated ammonium chloride solution. The mixture was extracted with ethyl acetate three times. The combined organic layer was dried over sodium sulfate and concentrated.

To a solution of compound 2 (1.0 eq) in ethanol and water was added iron powder (3.0 eq) and one drop of concentrated hydrochloric acid. The mixture was refluxed for 6.0 hours and filtered. The filtrate was diluted with ethyl acetate, washed with saturated sodium bicarbonate solution, dried over sodium sulfate, concentrated and purified by column chromatography to afford compound 3.

Reaction Scheme 2.

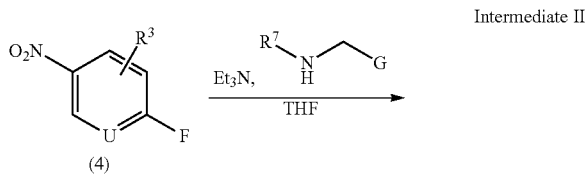

-continued

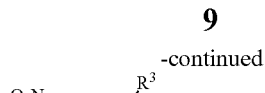

(5)

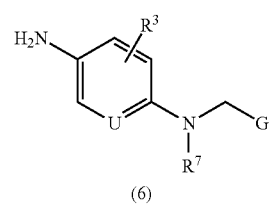

(6)

To a solution of 2-fluoro-5-nitropyridine 4 (1.0 eq) and amine (G-CH$_2$—HN—R$^7$, 1.0 eq) in tetrahydrofuran (0.2M) was added triethylamine (1.1 eq) and stirred at 25° C. After 3.0 hours, the reaction was followed by TLC and added brine solution. The mixture was extracted with ethyl acetate three times. The combined organic layer was dried over sodium sulfate and concentrated.

To a solution of compound 5 (1.0 eq) in ethanol and water was added iron powder (3.0 eq) and one drop of concentrated hydrochloric acid. The mixture was refluxed for 6.0 hours and filtrated. The filtrate was diluted with ethyl acetate, washed with saturated sodium bicarbonate solution, dried over sodium sulfate, concentrated and purified by column chromatography to afford compound 6.

Reaction Scheme 3.

Intermediate III

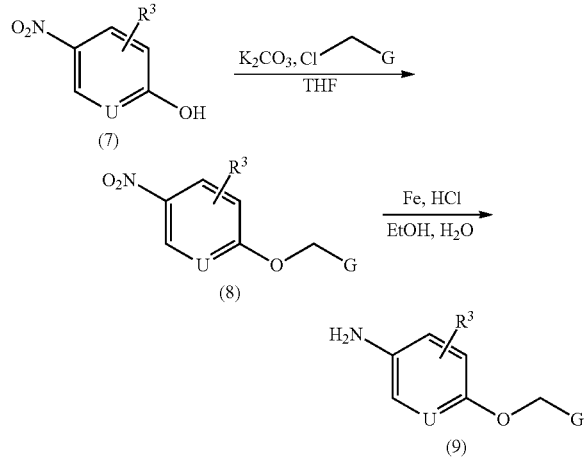

To a solution of compound 7 (1.0 eq) and alkylchloride (G-CH$_2$—Cl, 1.1 eq) in tetrahydrofuran was added potassium carbonate (1.5 eq) and stirred at 25° C. The reaction was followed by TLC and quenched with 1N hydrochloric acid after 6.0 hours. The mixture was extracted with ethyl acetate three times. The combined organic layer was dried over sodium sulfate and concentrated.

To a solution of compound 8 (1.0 eq) in ethanol and water was added iron powder (3.0 eq) and one drop of concentrated hydrochloric acid. The mixture was refluxed for 6.0 hours and filtrated. The filtrate was diluted with ethyl acetate, washed with saturated sodium bicarbonate solution, dried over sodium sulfate, concentrated and purified by column chromatography to afford compound 9.

Reaction Scheme 4.

Intermediate IV

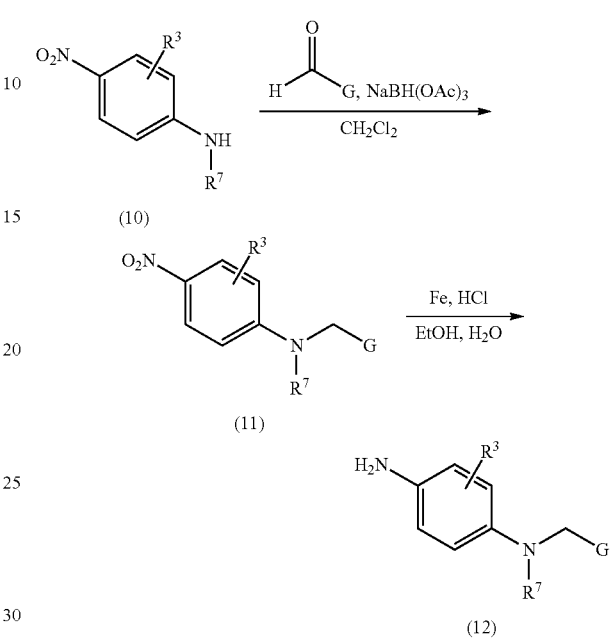

To a solution of 4-nitroaniline 10 (1.0 eq) and aldehyde (G-CHO, 1.0 eq) in dichloromethane (0.2M) was stirred at 25° C. under N$_2$ atmosphere. Sodium triacetoxyborohydride (1.5 eq) was added in small portions and the reaction mixture was stirred overnight at 25° C. A saturated aqueous sodium bicarbonate solution was added. The mixture was extracted with ethyl acetate three times. The combined organic layer was dried over sodium sulfate and concentrated.

To a solution of compound 11 (1.0 eq) in ethanol and water was added iron (3.0 eq) and one drop of concentrated hydrochloric acid. The mixture was refluxed for 6.0 hours and filtrated. The filtrate was diluted with ethyl acetate, washed with saturated sodium bicarbonate solution, dried over sodium sulfate, concentrated and purified to afford compound 12.

Reaction Scheme 5.

Intermediate V

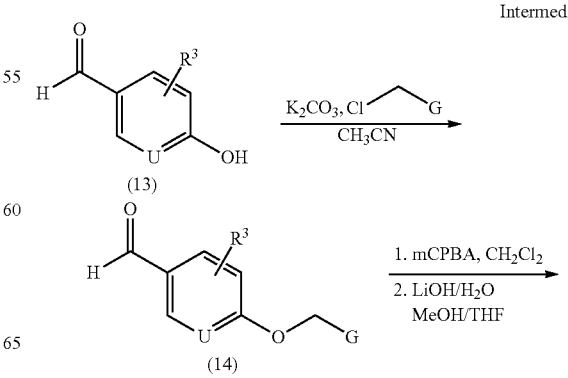

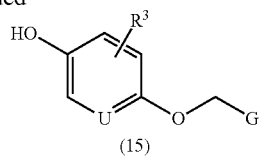

(15)

To a solution compound 13 (1.0 eq) in acetonitrile (0.2M) was added powdered potassium carbonate (1.2 eq) and dropwise alkyl chloride (G-CH$_2$—Cl, 1.1 eq). The mixture is vigorously stirred under nitrogen for 3 hours. Filtration and concentration yielded product as a solid.

To a solution of compound 14 (1.0 eq) in dichloromethane (2.0M) was added meta-chloroperoxybenzoic acid (mCPBA, 80-85%, 1.3 eq). The mixture is stirred at 25° C. for 3.0 hours and monitored by TLC. The solvent was concentrated to half its volume and filtered to remove the precipitated mCPBA. The filtrate was then washed with 5% aq. Sodium bicarbonate, water and brine. The solvent was subsequently removed under reduced pressure to afford an oily residue. This was re-dissolved in methanol and 2.5M aq. Sodium hydroxide was added to the solution at 0° C. After 1.5 hours, the reaction was acidified with 2M hydrochloric acid and the product was isolated by extraction with ethyl acetate. The combined organic layers were dried over sodium sulfate, concentrated and purified to afford compound 15.

Reaction Scheme 6.

Intermediate VI

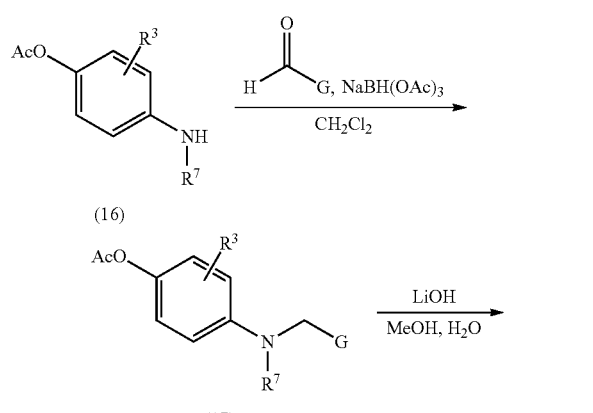

To a solution of 4-acetoxyaniline 16 (1.0 eq) and aldehyde (G-CHO, 1.0 eq) in dichloromethane (0.2M) was stirred at 25° C. under N$_2$ atmosphere. Sodium triacetoxyborohydride (1.5 eq) was added and the reaction mixture was stirred 16 hours. at 25° C. A saturated aqueous sodium bicarbonate solution was added. The mixture was extracted with ethyl acetate three times. The combined organic layer was dried over sodium sulfate and concentrated.

To a solution of compound 17 and lithium hydroxide in methanol and water was stirred at 25° C. for 2.0 hours. The reaction was acidified with 2M aq. hydrochloric acid and the product was isolated by extraction with ethyl acetate. The combined organic layers were dried over sodium sulfate, concentrated and purified to afford compound 18.

Reaction Scheme 7.

Intermediate VII

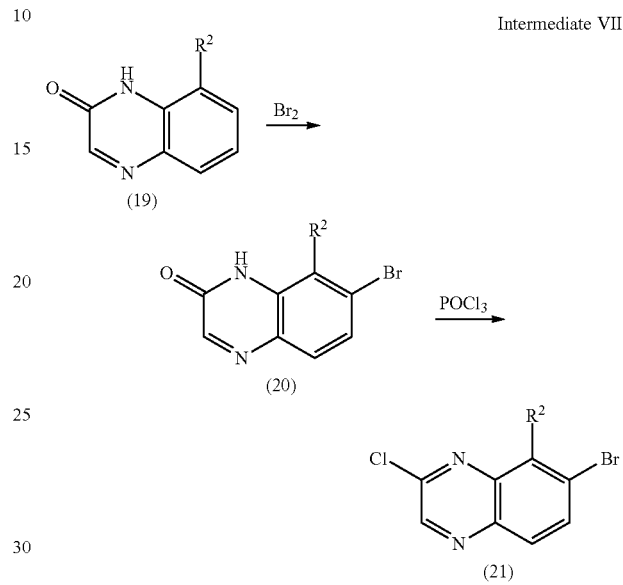

Bromine (1.0 eq) was slowly added to a solution of substituted-quinoxalinone (19) in acetic acid (0.1M). The reaction mixture was stirred at ambient temperature for 1.5 hours. The resulting solids were collected by filtration and washed with hexanes to afford 7-bromo-substituted-quinoxalinone 20.

A suspension of compound 20 (1.0 eq) in phosphoryl chloride (1.0M) was heated to reflux for 6 hours. The resulting clear solution was then cooled to room temperature and quenched by water. The resulting solids were collected by filtration to afford 7-bromo-2-chloro-substituted-quinoxaline 21, which was carried to the next step without further purification.

Reaction Scheme 8.

Intermediate VIII

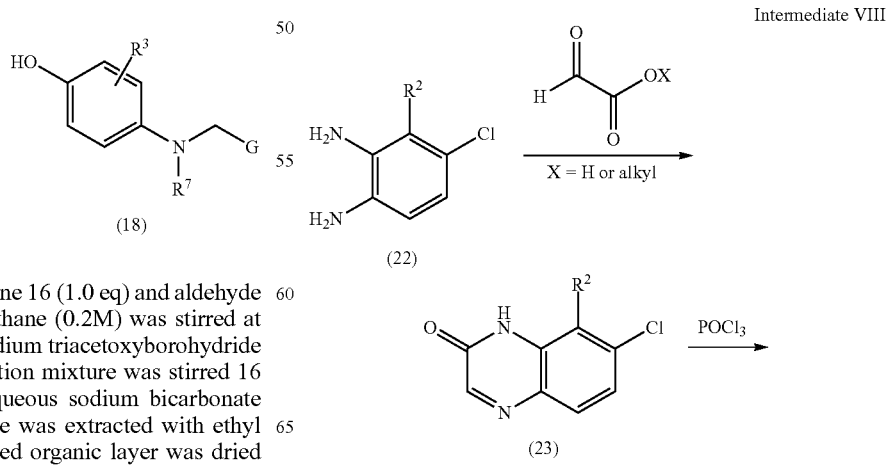

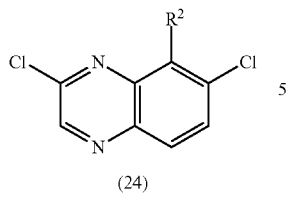

(24)

Glyoxylic acid or alkyl glyoxalate and 3-substituted-4-chlorobenzene-1,2-diamine 22 were stirred in organic solvent. The resulting products were purified to afford 7-chloro-substituted-quinoxalinone 23.

A suspension of 7-chloro-substituted-quinoxalinone 23 (1.0 eq) in phosphoryl chloride (1.0M) was heated to reflux for 6 hours. The resulting clear solution was then cooled to room temperature and quenched by water. The resulting solids were collected by filtration to afford 2, 7-dichloro-substituted-quinoxaline 24, which was carried to the next step without further purification.

Reaction Scheme 9.

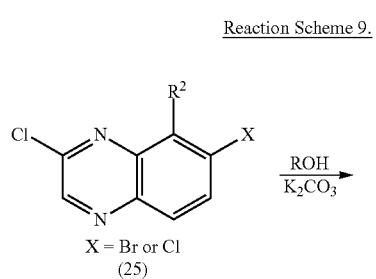

Intermediate IX

X = Br or Cl
(25)

↓ ROH / K₂CO₃

X = Br or Cl
(26)

To a solution of 2-chloro-substituted-quinoxaline 25 (1.0 eq) in alcohol (ROH, 0.5M) was added potassium carbonate (1.1 eq) at room temperature, and the reaction was heated at 40° C. for 2 hours. After cooling, the reaction mixture was filtered and concentrated in vacuo. The resulting residue was diluted with ethyl acetate, washed with brine, dried over magnesium sulfate and concentrated in vacuo to afford compound 26.

Reaction Scheme 10.

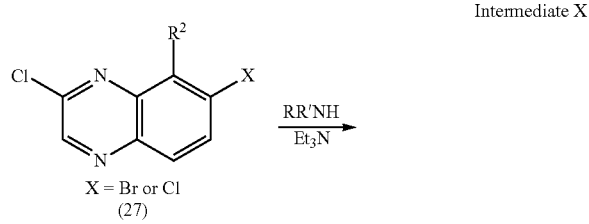

Intermediate X

X = Br or Cl
(27)

↓ RR'NH / Et₃N

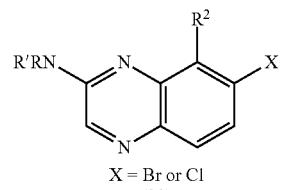

X = Br or Cl
(28)

To a solution of 2-chloro-substituted-quinoxaline 27 (1.0 eq) in amine (R'RNH, 0.5M) was added triethylamine (1.1 eq) at room temperature and the reaction was heated at 60° C. for 2 hours. After cooling, the reaction mixture was filtered and concentrated in vacuo. The resulting residue was diluted with ethyl acetate, washed with brine, dried over magnesium sulfate and concentrated in vacuo to afford compound 28.

Reaction Scheme 11.

Intermediate XI

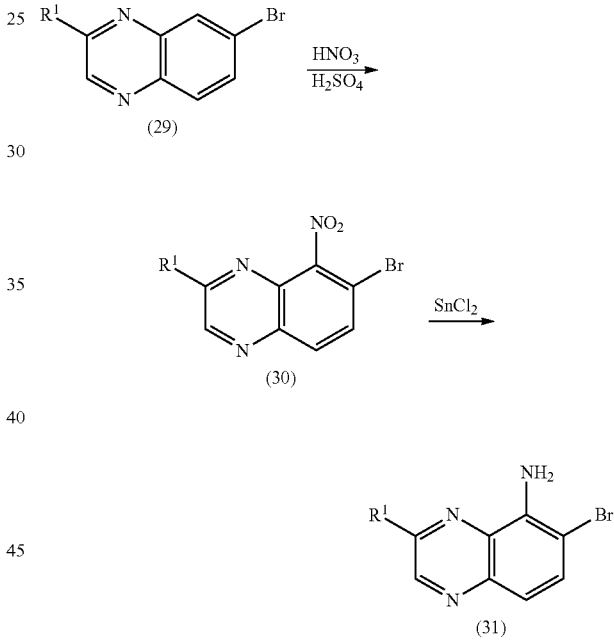

To a solution of 7-bromo-substituted-quinoxaline 29 (1.0 eq) in sulfuric acid was added nitric acid. The reaction mixture was stirred at room temperature for 8 hours. The mixture was poured onto an ice-water mixture, and filtered. The solid was washed with ethyl acetate to afford the 7-bromo-8-nitro-substituted-quinoxaline 30.

To a solution of 7-bromo-8-nitro-substituted-quinoxaline 30 (1.0 equiv) in ethyl acetate/dimethylformamide (6:1) was added tin (II) chloride (SnCl₂; 10.0 equiv). The reaction mixture was stirred at 100° C. for 16 hours. After cooling, the reaction mixture was concentrated in vacuo. The resulting residue was diluted with ethyl acetate, washed with saturated aq. sodium bicarbonate solution and brine, dried over magnesium sulfate, filtered and concentrated in vacuo to afford 6-bromo-substituted-quinoxalin-5-amine 31.

Reaction Scheme 12.

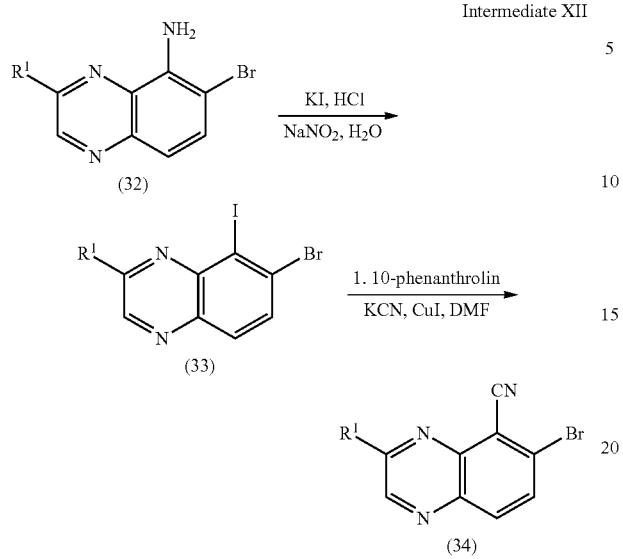

7-Bromo-substituted-quinoxalin-5-amine 32 (1.0 equiv), hydrogen chloride (1.5 equiv) and sodium nitrite (1.1 equiv) in water were added potassium iodide (1.2 equiv) at −10° C. The reaction was stirred at room temperature for 16 hours. The crude reaction mixture was diluted with ethyl acetate, and the organic layer was washed with brine, dried over magnesium sulfate and filtered. The solvent was removed under reduced pressure and the residual purified via silica gel column chromatography to give 7-bromo-8-iodo-substituted-quinoxaline 33.

7-Bromo-8-iodo-substituted-quinoxaline 33 (1.0 equiv), potassium cyanide (2.0 equiv), copper iodide (1.1 equiv) and 1,10-phenanthroline monohydrate (0.2 equiv) in dimethylformamide were heated at 110° C. for 24 hours in sealed tube. The reaction mixture was filtered and washed with methanol, and the solvent was removed under vacuo. The crude reaction mixture was diluted with ethyl acetate, and the organic layer was washed with saturated aq. sodium bicarbonate solution and brine, dried over magnesium sulfate and filtered. Ethyl acetate was removed under reduced pressure and the residual purified via silica gel column chromatography to give 7-bromo-8-cyano-substituted-quinoxaline 34.

Reaction Scheme 13.

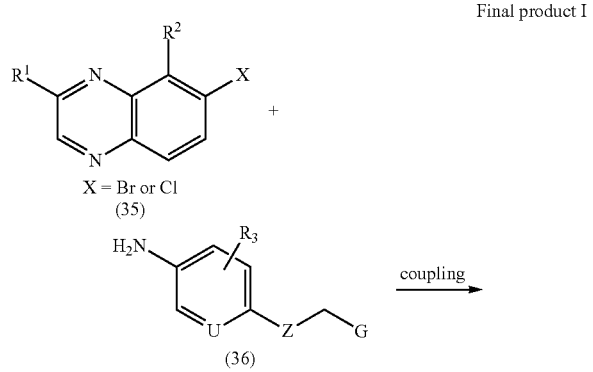

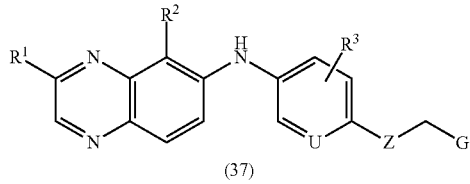

Substituted-quinoxaline 35 (1.0 eq), cesium carbonate (3.0 eq), palladium(II) acetate (0.1 eq) compound 36 (1.0 eq) and xantphos (4,5-Bis(diphenylphosphino)-9,9-dimethylxanthene) (0.02 eq) in 1,4-dioxane (0.3M) were heated at 110° C. for 2 hours. The solution was filtered, washed with methanol and concentrated in vacuo. The residual was purified via silica gel column chromatography to give final compound 37.

Reaction Scheme 14.

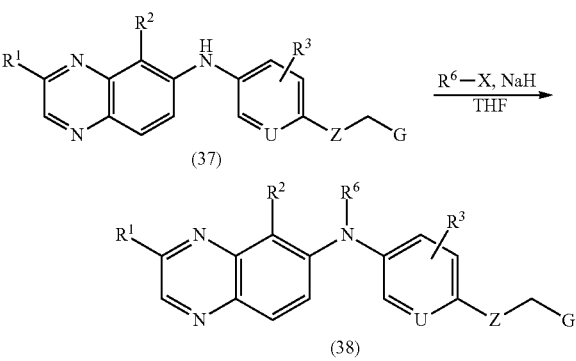

To a solution of compound 37 (1.0 eq) and alkyl halide ($R^6$—X, 1.0 eq) in tetrahydrofuran (0.2M) was added sodium hydride (1.1 eq) and stirred at 0° C. After 3.0 hours, the reaction was followed by TLC and quenched with saturated ammonium chloride solution. The mixture was extracted with ethyl acetate three times. The combined organic layer was dried over sodium sulfate and concentrated. The residual was purified via silica gel column chromatography to give final compound 38.

Reaction Scheme 15.

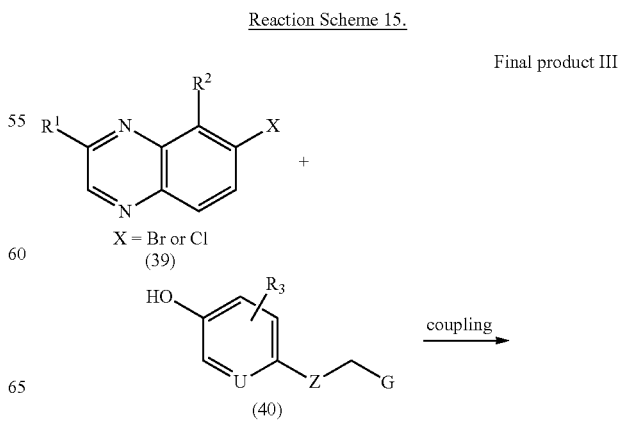

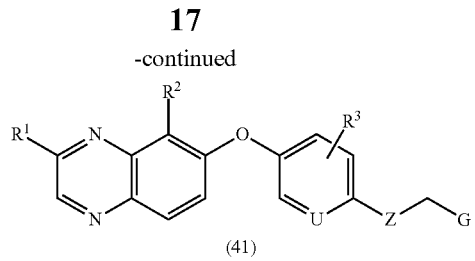

(41)

Substituted-quinoxaline 39 (1.0 eq), cesium carbonate (3.0 eq), CuI (0.1 eq) and compound 40 (1.0 eq) in dimethylformamide (0.3M) were heated at 110° C. for 2 hours. The solution was filtered, washed with methanol and concentrated in vacuo. The residual was purified via silica gel column chromatography to give final compound 41.

Reaction Scheme 16

Final product IV

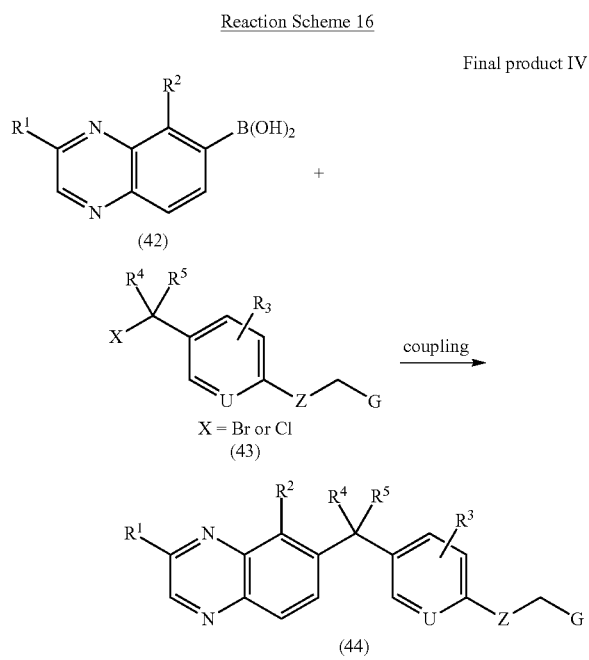

To a solution of halide 43 (1.2 eq) in toluene/ethanol (0.2M) were added a quinaxoline compound 42 (1.0 eq), tetrakis(triphenylphosphine) palladium(0) (0.05 eq) and cesium carbonate (1.2 eq) and the mixture was stirred at 100° C. for 18 hours. The reaction mixture was cooled to room temperature and filtered off through celite. The filtrate was concentrated in vacuo. The residue was purified by chromatography to give final compound 44.

Reaction Scheme 17

Final product V

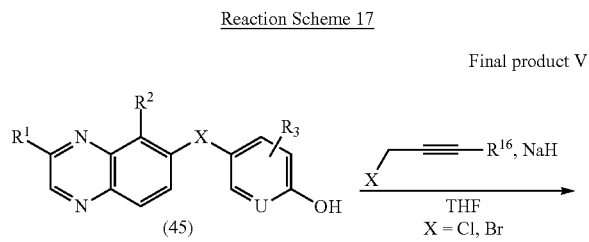

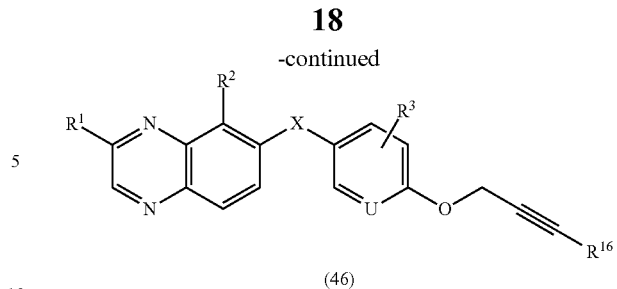

(46)

To a solution of compound 45 (1.0 eq) and alkyne halide (1.0 eq) in tetrahydrofuran (0.2M) was added Sodium hydride (1.1 eq) and stirred at 0° C. After 3.0 hours, the reaction was followed by TLC and quenched with saturated ammonium chloride solution. The mixture was extracted with ethyl acetate three times. The combined organic layer was dried over sodium sulfate and concentrated. The residual was purified via silica gel column chromatography to give final compound 46.

The above reaction schemes illustrate how quinoxaline compounds of the invention may be prepared. One skilled in the art would appreciate that the reactions involved and the reagents used in these reactions are known in the art. Therefore, based on the above teachings and the common knowledge in the art, quinoxaline compounds with various substituents, as defined herein, can be prepared by one skilled in the art without inventive efforts.

The compounds of Formula I represent novel potent inhibitors of protein tyrosine kinases, such as PDGFR, CSF-1R, FLT3 and c-KIT and may be useful in the prevention and treatment of disorders resulting from actions of these kinases.

Compounds of Formula I may be of therapeutic value in the treatment of diseases or disorders selected from fibrosis, bone-related diseases, cancer, autoimmune disorders, inflammatory diseases, cardiovascular diseases, pain and burns.

In accordance with some embodiments of the invention, compounds of Formula I are useful for the treatment of fibrotic diseases. Examples of fibrosis include idiopathic pulmonary fibrosis (IPF), nephrogenic genic systemic fibrosis (NSF), cirrhosis of the liver, diabetes-induced nephropathy, cardiac fibrosis (for example, endomyocardial fibrosis), mediastinal fibrosis, myelofibrosis, retroperitoneal fibrosis, Crohn's disease, keloid formation, scleroderma and systemic sclerosis. Additional examples of fibrotic diseases include focal segmental glomerular sclerosis (FSGS), interstitial lung disease in systemic sclerosis (SSc-ILD), primary biliary cirrhosis, ethanol cirrhosis, interstitial fibrosis and tubular atrophy (CAD), proliferative vitreoretinopathy, and scarring (hypertrophic and keloid).

In accordance with some embodiments of the invention, compounds of Formula I are useful for the treatment of bone-related diseases include metastatic bone disease, treatment-induced bone loss, osteoporosis, rheumatoid arthritis, ankylosing spondylitis, Paget's disease, and periodontal disease. The osteoporosis may be attributed to (1) menopause in women, (2) aging in men or women, (3) suboptimal bone growth during childhood and adolescence that resulted in failure to reach peak bone mass, and/or (4) bone loss secondary to other disease conditions, eating disorders, medications and/or medical treatments (for example, as a result of treatment with glucocorticoids, aromatase inhibition therapy, or anti-androgen therapy).

Other osteolytic diseases that can be treated according to the present invention are more localized. A particular example is metastatic tumor-induced osteolysis. In this condition, bone cancers or bone metastases induce localized osteolysis that causes pain, bone weakness and fractures. Such localized osteolysis also permits tumors to grow larger by creating more space for them in the bone and releasing growth factors from the bone matrix. Cancers presently known to cause tumor-induced osteolysis include hematological malignancies (e.g., myeloma and lymphoma) and solid tumors (e.g., breast, prostate, lung, renal and thyroid), all of which the present invention contemplates treating.

In accordance with some embodiments of the invention, compounds of Formula I are useful for the treatment of cancers and proliferative disorders. Examples include multiple myeloma, acute myeloid leukemia (AML), chronic myeloid leukemia (CML), prostate cancer, breast cancer, ovarian cancer, melanoma, glioblastoma multiforme, giant cell tumor of bone (also known as osteoclastome), giant cell tumor of the tendon sheath (also known as tenosynovial giant cell tumor or TGCT), metastasis of tumors to other tissues, other chronic myeloproliferative diseases such as myelofibrosis, and pigmented villonodular synovitis (PVNS).

In accordance with some embodiments of the invention, compounds of Formula I are useful for the treatment of autoimmune disorders and inflammatory diseases include, but are not limited to, rheumatoid arthritis, osteoarthritis, psoriatic arthritis, ankylosing spondylitis, Adult Still's, glomerulonephritis, osteoporosis, Sjogren's syndrome, inflammatory bowel disease, ulcerative colitis, Crohn's disease, Langerhans cell histiocytosis, hemophagocytic syndrome, multicentric reticulohistiocytosis, Paget's disease, primary sclerosing cholangitis and transplant rejection (including hepatic, renal and heart/lung transplants).

In accordance with some embodiments of the invention, compounds of Formula I are useful for the treatment of cardiovascular diseases. Examples of cardiovascular diseases include atherosclerosis, peripheral vascular disease, coronary artery disease, ischemia/reperfusion, hypertension, restenosis, pulmonary arterial hypertension and arterial inflammation. Additional examples of cardiovascular diseases include acute respiratory distress syndrome (ARDA), arteriovenous (AV) fistula patency and veno-occlusive disease (post-HSC/BMT).

In accordance with some embodiments of the invention, compounds of Formula I are useful for the treatment of pain. In one embodiment, the compounds of Formula I are useful for the treatment of pain as a result of nerve injury. In one embodiment, the compounds of Formula I are useful for the treatment of neuropathic pain associated with nerve inflammation (neuritis) in the absence of nerve injury. Such pain syndromes include back pain, temporomandibular joint (TMJ) disorder, and rheumatoid arthritis.

The quinoxaline compounds mentioned herein may contain a non-aromatic double bond and one or more asymmetric centers, e.g., in the substituents attached to the core aromatic rings. Therefore, these compounds may occur as racemates and racemic mixtures, single enantiomers, individual diastereomers, diastereomeric mixtures, and cis- or trans-isomeric forms. All such isomeric forms are within the scope of the invention. The quinoxaline compounds of the invention may have acidic or basic functional groups (e.g., on the substitution groups) that may form salts, particularly pharmaceutically acceptable salts. Formation of such salts is a routine practice in the pharmaceutical industry. Examples of salts that may be used with quinoxaline compounds of the invention, for example, include hydrochloride, sulfate, formate, acetate, malate, succinate, etc. for the basic functional groups, and hydroxide, ammonium, alkylammonium, etc. for acidic functional groups. Such quinoxaline salts are within the scope of the invention. Similarly, the acidic or basic groups may be functionalized, for example into esters. Such functionalized derivatives will be hydrolyzed in vivo. Therefore, such derivatives may function as pro-drugs of the quinoxaline compounds of the invention. Formation of pro-drugs involves only routine skills and one skilled in the art would know how to prepare and use such pro-drugs without undue experimentation.

Also within the scope of this invention are (1) a pharmaceutical composition that contains an effective amount of at least one of the quinoxaline compounds of this invention and a pharmaceutically acceptable carrier, (2) a method for treating a protein kinase-related disease (e.g., cancer) by administering to a subject in need of such treatment an effective amount of such a quinoxaline compound, and (3) a method of decreasing the activity of at least one protein kinase by contacting the at least one protein kinase with at least one of the quinoxaline compounds of this invention.

As used herein, the term a "protein kinase-related disease/disorder," or "protein kinase-associated disease/disorder," or "disease/disorder modulated by a protein kinase" refers to a disease or condition that is characterized by an abnormal protein kinase (PK) activity or a disease or condition that can be treated with changes to the activity of at least one PK. Abnormal PK activity can arise from elevated PK expression level, or presence of PK expression that does not happen in normal conditions. PK-related disease/disorder described herein include, but not limited to, cancer, diabetes, a hyper-proliferation disorder, hyperproliferative disorders of the kidney, renal disease, von Hippel-Lindau disease, restenosis, fibrosis, psoriasis, osteoarthritis, rheumatoid arthritis, an inflammatory disorder, immunological disorders such as autoimmune diseases (e.g., AIDS, lupus, etc.), cardiovascular disorders (e.g. atherosclerosis), and blood vessel proliferative disorders such as abnormal vasculogenesis.

The term "treating" refers to administering a quinoxaline compound to a subject that has a protein kinase-related disease/disorder, or has a symptom of or a predisposition toward it, with the purpose to cure, heal, alleviate, relieve, alter, remedy, ameliorate, improve, affect or reduce the risk of the disorder, the symptoms of or the predisposition toward the disorder. For example, treating cancer refers to the treatment results in inhibition of cancer growth or cancer cell growth, regression in cancer growth (i.e. it reduces the size of a detectable cancer), or the disappearance of a cancer.

The term "an effective amount" refers to the amount of the active agent that is required to confer the intended therapeutic effect in the subject. Effective amounts may vary, as recognized by those skilled in the art, depending on routes of administration, excipient usages, and the possibility of co-usage with other agents. Determination of an effective amount requires only routine skills, and one skilled in the art would be able to determine such effective amounts for the intended use without undue experimentation. The subject in need of the treatment can be a mammal. The term "mammal" refers to human or nonhuman mammal, for example, dogs, cats, pigs, cows, sheep, goats, horses, rats, or mice.

To practice a method of this invention, the above-described pharmaceutical composition can be administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In accordance with some embodiments of the invention, a quinoxaline compound of this invention may be administered intravenously, suitable carriers may include, but are not limited to, physiological saline or phosphate buffered saline (PBS), and solutions containing thickening and solubilizing agents, such as glucose, polyethylene glycol, and polypropylene glycol and mixtures thereof.

A sterile injectable composition, e.g., a sterile injectable aqueous or oleaginous suspension, can be formulated according to techniques known in the art using suitable dispersing or wetting agents (such as TWEEN 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectable, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

A composition for oral administration can be any orally acceptable dosage form including, but not limited to, capsules, tablets, emulsions and aqueous suspensions, dispersions and solutions. In the case of tablets for oral use, carriers that are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. A nasal aerosol or inhalation composition can be prepared according to techniques well known in the art of pharmaceutical formulation. A quinoxaline compound-containing composition can also be administered in the form of suppositories for rectal administration.

A carrier in the pharmaceutical composition should be "acceptable" in the sense of being compatible with the active ingredient of the formulation (and preferably, capable of stabilizing it) and not deleterious to the subject to be treated. One or more solubilizing agents (e.g., cyclodextrin) which form more soluble complexes with the active quinoxaline compounds can be utilized as pharmaceutical carriers for delivery of the active compounds. Examples of other carriers include colloidal silicon dioxide, magnesium stearate and sodium lauryl sulfate.

Without further elaboration, it is believed that the above description has adequately enabled the present invention. The following examples are, therefore, to be construed as merely illustrative, and not limitative of the remainder of the disclosure in any way whatsoever.

EXAMPLES

Exemplary quinoxaline compounds are listed in Table 1. Their calculated mass and observed ESI-MS data are provided in Table 2.

TABLE 1

Quinoxaline compounds

| Compound No. | Structure |
|---|---|
| 1 | 3-methoxy-6-((6-(((6-(trifluoromethyl)pyridin-3-yl)methyl)amino)pyridin-3-yl)amino)quinoxaline-5-carbonitrile |
| 2 | $N^5$-(3-methoxyquinoxalin-6-yl)-$N^2$-((6-(trifluoromethyl)pyridin-3-yl)methyl)pyridine-2,5-diamine |

TABLE 1-continued

Quinoxaline compounds

| Compound No. | Structure |
|---|---|
| 3 | 3-methoxy-6-((3-methoxy-4-((4-methoxybenzyl)oxy)phenyl)amino)quinoxaline-5-carbonitrile |
| 4 | 3-methoxy-6-((6-((4-(trifluoromethyl)benzyl)amino)pyridin-3-yl)amino)quinoxaline-5-carbonitrile |
| 5 | 3-methoxy-N-(3-methoxy-4-((4-methoxybenzyl)oxy)phenyl)quinoxalin-6-amine |
| 6 | 3-methoxy-6-((6-(pyridin-3-ylmethoxy)pyridin-3-yl)amino)quinoxaline-5-carbonitrile |
| 7 | 3-(dimethylamino)-6-((3-methoxy-4-((4-methoxybenzyl)oxy)phenyl)amino)quinoxaline-5-carbonitrile |

TABLE 1-continued

Quinoxaline compounds

| Compound No. | Structure |
|---|---|
| 8 | 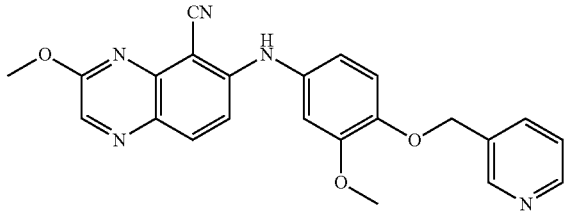 [SMILES: COc1cnc2ccc(Nc3ccc(OCc4cccnc4)c(OC)c3)c(C#N)c2n1]<br>3-methoxy-6-((3-methoxy-4-(pyridin-3-ylmethoxy)phenyl)amino)quinoxaline-5-carbonitrile |
| 9 | 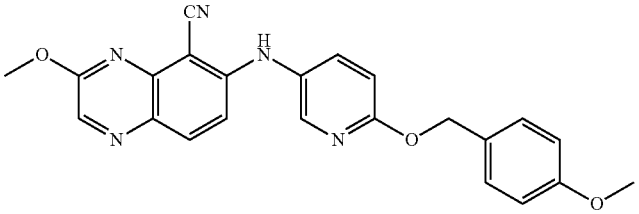<br>3-methoxy-6-((6-((4-methoxybenzyl)oxy)pyridin-3-yl)amino)quinoxaline-5-carbonitrile |
| 10 | 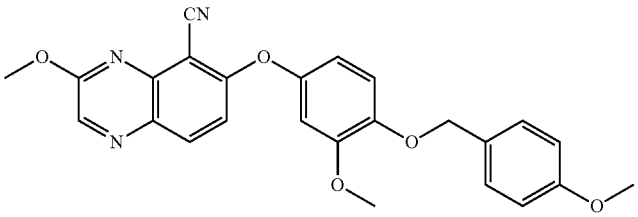<br>3-methoxy-6-(3-methoxy-4-((4-methoxpenzyl)oxy)phenoxy)quinoxaline-5-carbonitrile |
| 11 | 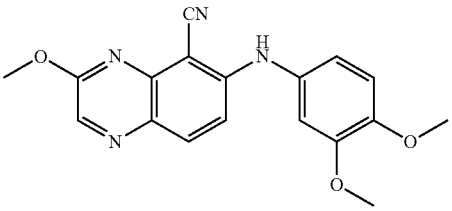<br>6-((3,4-dimethoxyphenyl)amino)-3-methoxyquinoxaline-5-carbonitrile |
| 12 | 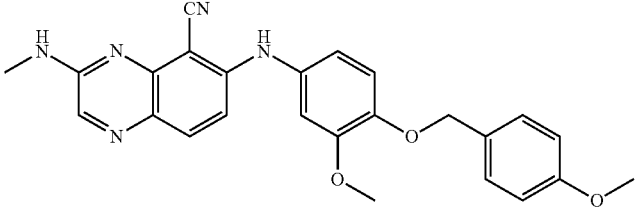<br>6-((3-methoxy-4-((4-methoxybenzyl)oxy)phenyl)amino)-3-(methylamino)quinoxaline-5-carbonitrile |

TABLE 1-continued

Quinoxaline compounds

| Compound No. | Structure |
|---|---|
| 13 | 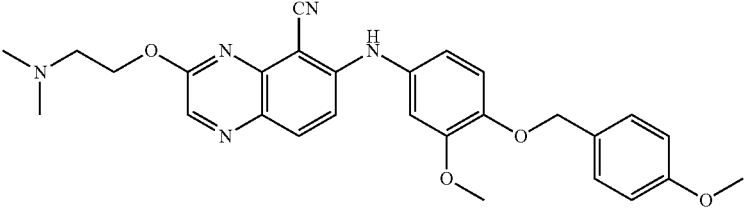<br>3-(2-(dimethylamino)ethoxy)-6-((3-methoxy-4-((4-methoxybenzyl)oxy)phenyl)amino)quinoxaline-5-carbonitrile |
| 14 | 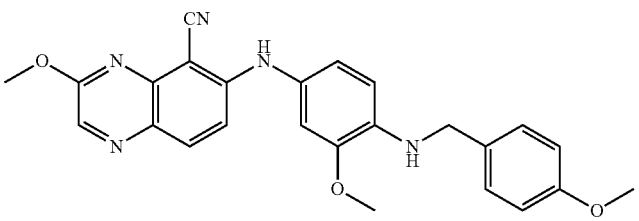<br>3-methoxy-6-((3-methoxy-4-((4-methoxybenzyl)amino)phenyl)amino)quinoxaline-5-carbonitrile |
| 15 | 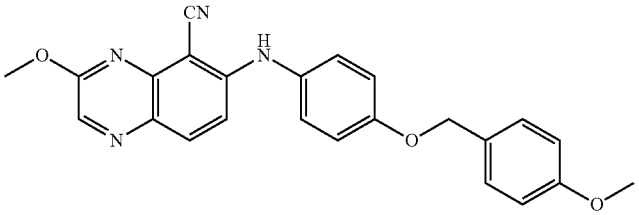<br>3-methoxy-6-((4-((4-methoxybenzyl)oxy)phenyl)amino)quinoxaline-5-carbonitrile |
| 16 | 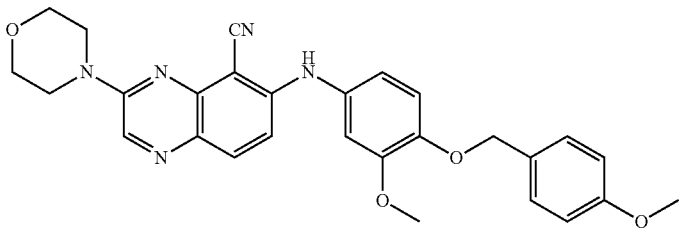<br>6-((3-methoxy-4-((4-methoxybenzyl)oxy)phenyl)amino)-3-morpholinoquinoxaline-5-carbonitrile |
| 17 | 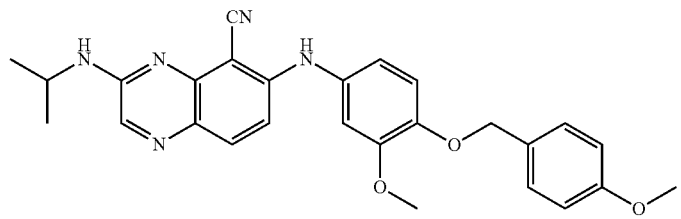 [SMILES: COc1ccc(COc2ccc(Nc3ccc4ncc(NC(C)C)nc4c3C#N)cc2OC)cc1]<br>3-(isopropylamino)-6-((3-methoxy-4-((4-methoxybenzyl)oxy)phenyl)amino)quinoxaline-5-carbonitrile |

TABLE 1-continued

Quinoxaline compounds

| Compound No. | Structure |
|---|---|
| 18 | 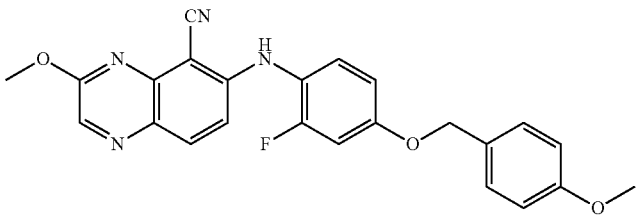<br>6-((2-fluoro-4-((4-methoxybenzyl)oxy)phenyl)amino)-3-methoxyquinoxaline-5-carbonitrile |
| 19 | 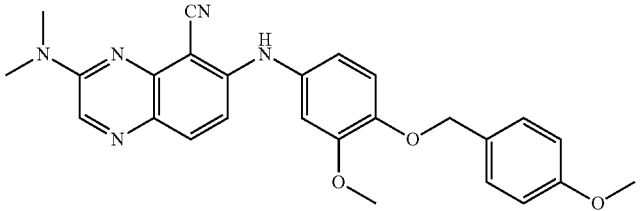<br>3-(dimethylamino)-6-(3-methoxy-4-((4-methoxybenzyl)oxy)phenoxy)quinoxaline-5-carbonitrile |
| 20 | 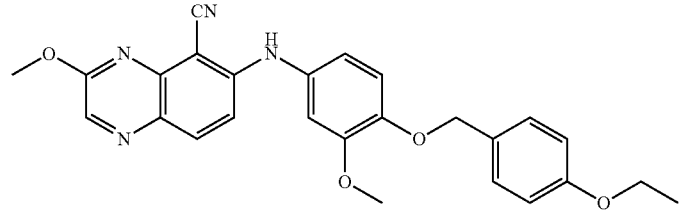 [SMILES: CCOc1ccc(COc2ccc(Nc3ccc4ncc(OC)nc4c3C#N)cc2OC)cc1]<br>6-((4-((4-ethoxybenzyl)oxy)-3-methoxyphenyl)amino)-3-methoxyquinoxaline-5-carbonitrile |
| 21 | 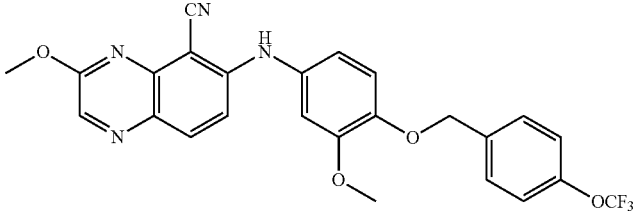 [SMILES: COc1cnc2ccc(Nc3ccc(OCc4ccc(OC(F)(F)F)cc4)c(OC)c3)c(C#N)c2n1]<br>3-methoxy-6-((3-methoxy-4-((4-(trifluoromethoxy)benzyl)oxy)phenyl)amino)quinoxaline-5-carbonitrile |
| 22 | 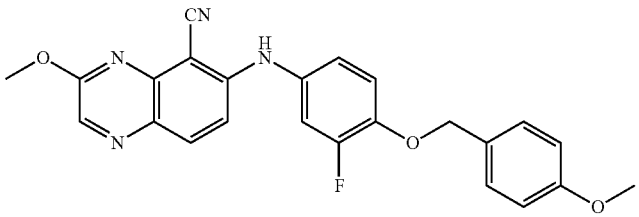<br>6-((3-fluoro-4-((4-methoxybenzyl)oxy)phenyl)amino)-3-methoxyquinoxaline-5-carbonitrile |

TABLE 1-continued

Quinoxaline compounds

| Compound No. | Structure |
|---|---|
| 23 | 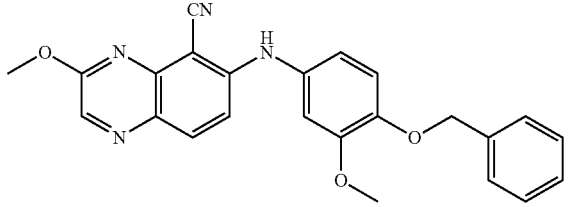 [SMILES: COc1cnc2ccc(Nc3ccc(OCc4ccccc4)c(OC)c3)c(C#N)c2n1]
6-((4-(benzyloxy)-3-methoxyphenyl)amino)-3-methoxyquinoxaline-5-carbonitrile |
| 24 | 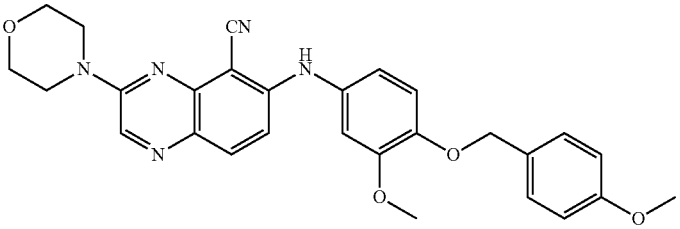 [SMILES: COc1ccc(COc2ccc(Nc3ccc4ncc(N5CCOCC5)nc4c3C#N)cc2OC)cc1]
N-(3-methoxy-4-((4-methoxybenzyl)oxy)phenyl)-3-morpholinoquinoxalin-6-amine |
| 25 | 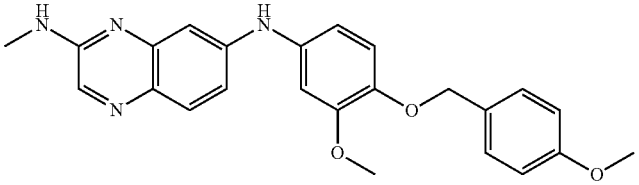
$N^7$-(3-methoxy-4-((4-methoxybenzyl)oxy)phenyl)-$N^2$-methylquinoxaline-2,7-diamine |
| 26 | 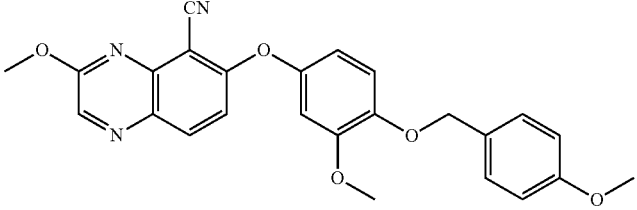
3-methoxy-6-(3-methoxy-4-((4-methoxybenzyl)oxy)phenoxy)quinoxaline-5-carbonitrile |
| 27 | 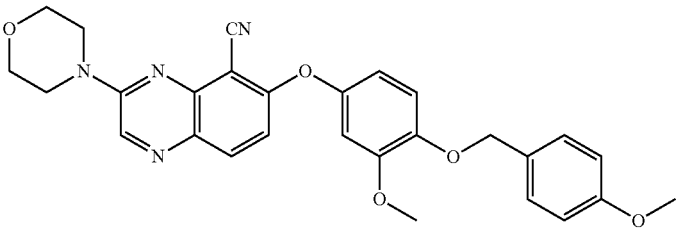 [SMILES: COc1ccc(COc2ccc(Oc3ccc4ncc(N5CCOCC5)nc4c3C#N)cc2OC)cc1]
6-(3-methoxy-4-((4-methoxybenzyl)oxy)phenoxy)-3-morpholinoquinoxaline-5-carbonitrile |

TABLE 1-continued

Quinoxaline compounds

| Compound No. | Structure |
|---|---|
| 28 | 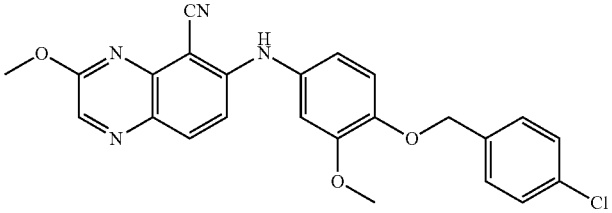 [SMILES: COc1cnc2ccc(Nc3ccc(OCc4ccc(Cl)cc4)c(OC)c3)c(C#N)c2n1]<br>6-(4-((4-chlorobenzyl)oxy)-3-methoxphenoxy)-3-methoxyquinoxaline-5-carbonitrile |
| 29 | 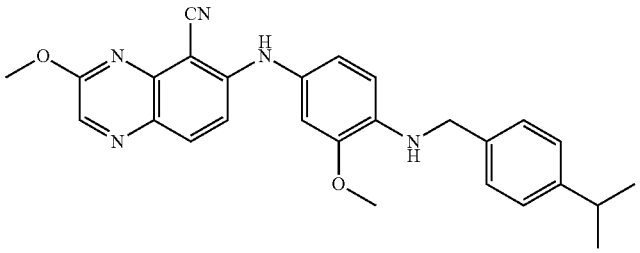 [SMILES: COc1cnc2ccc(Nc3ccc(NCc4ccc(C(C)C)cc4)c(OC)c3)c(C#N)c2n1]<br>6-((4-((4-isopropylbenzyl)amino)-3-methoxyphenyl)amino)-3-methoxyquinoxaline-5-carbonitrile |
| 30 | 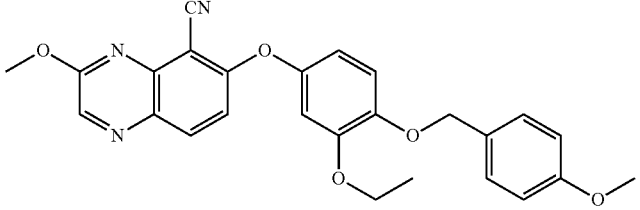<br>6-(3-ethoxy-4-((4-methoxybenzyl)oxy)phenoxy)-3-methoxyquinoxaline-5-carbonitrile |
| 31 | 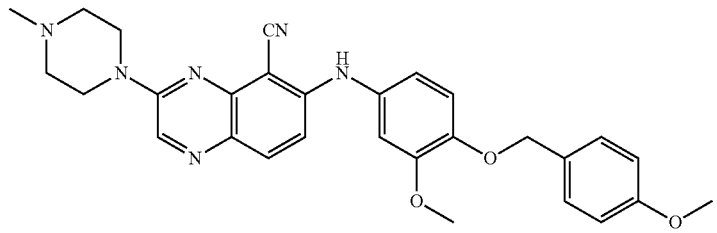<br>6-((3-methoxy-4-((4-methoxybenzyl)oxy)phenyl)amino)-3-(4-methylpiperazin-1-yl)quinoxaline-5-carbonitrile |
| 32 | 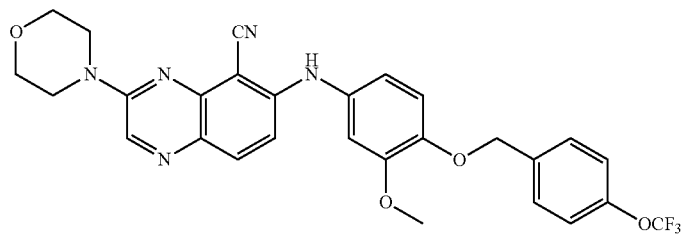 [SMILES: COc1cc(Nc2ccc3ncc(N4CCOCC4)nc3c2C#N)ccc1OCc1ccc(OC(F)(F)F)cc1]<br>6-((3-methoxy-4-((4-(trifluoromethoxy)benzyl)oxy)phenyl)amino)-3-morpholinoquinoxaline-5-carbonitrile |

TABLE 1-continued

Quinoxaline compounds

| Compound No. | Structure |
|---|---|
| 33 | 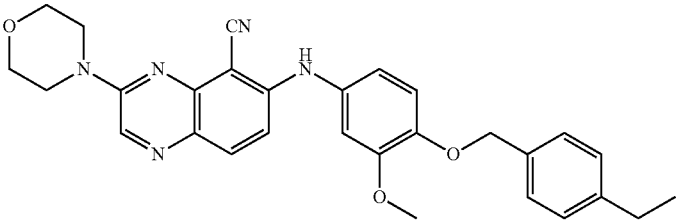 [SMILES: CCc1ccc(COc2ccc(Nc3ccc4ncc(N5CCOCC5)nc4c3C#N)cc2OC)cc1]<br>6-((4-((4-ethylbenzyl)oxy)-3-methoxyphenyl)amino)-3-morpholinoquinoxaline-5-carbonitrile |
| 34 | 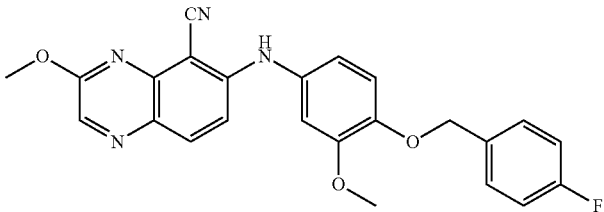 [SMILES: COc1cnc2ccc(Nc3ccc(OCc4ccc(F)cc4)c(OC)c3)c(C#N)c2n1]<br>6-((4-((4-fluorobenzyl)oxy)-3-methoxphenyl)amino)-3-methoxyquinoxaline-5-carbonitrile |
| 35 | 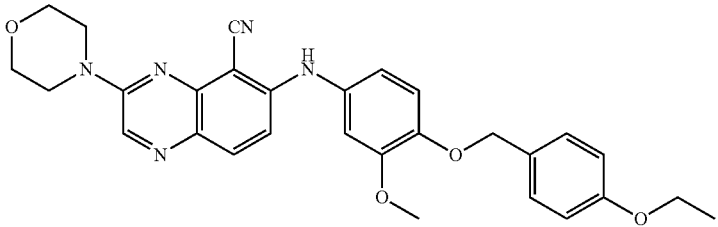 [SMILES: CCOc1ccc(COc2ccc(Nc3ccc4ncc(N5CCOCC5)nc4c3C#N)cc2OC)cc1]<br>6-((4-((4-ethoxybenzyl)oxy)-3-methoxyphenyl)amino)-3-morpholinoquinoxaline-5-carbonitrile |
| 36 | 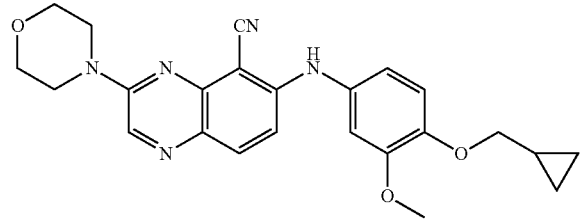 [SMILES: COc1cc(Nc2ccc3ncc(N4CCOCC4)nc3c2C#N)ccc1OCC1CC1]<br>6-((4-(cyclopropylmethoxy)-3-methoxyphenyl)amino)-3-morpholinoquinoxaline-5-carbonitrile |
| 37 | 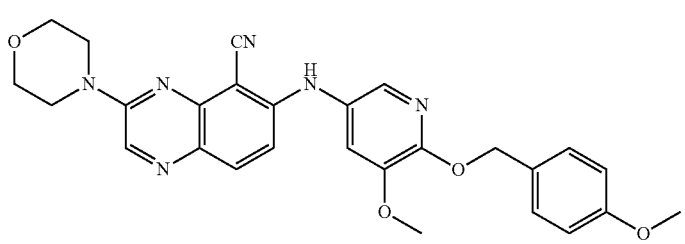<br>6-((5-methoxy-6-((4-methoxybenzyl)oxy)pyridin-3-yl)amino)-3-morpholinoquinoxaline-5-carbonitrile |

TABLE 1-continued

Quinoxaline compounds

| Compound No. | Structure |
|---|---|
| 38 | 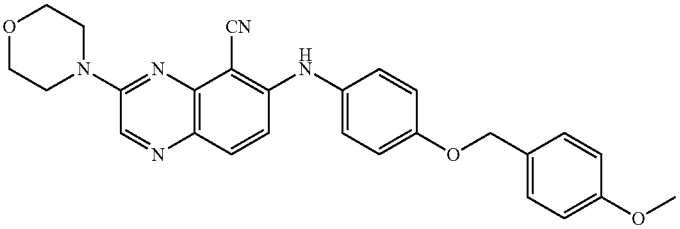 [SMILES: COc1ccc(COc2ccc(Nc3ccc4ncc(N5CCOCC5)nc4c3C#N)cc2)cc1]<br>6-((4-((4-methoxybenzyl)oxy)phenyl)amino)-3-morpholinoquinoxaline-5-carbonitrile |
| 39 | 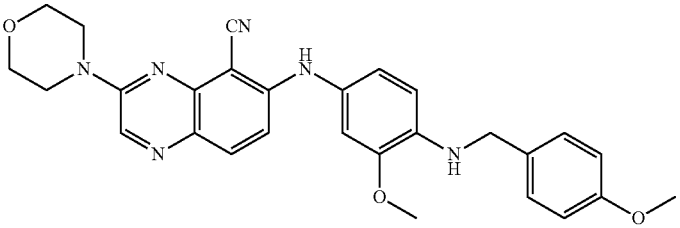 [SMILES: COc1ccc(CNc2ccc(Nc3ccc4ncc(N5CCOCC5)nc4c3C#N)cc2OC)cc1]<br>6-((3-methoxy-4-((4-methoxybenzyl)amino)phenyl)amino)-3-morpholinoquinoxaline-5-carbonitrile |
| 40 | 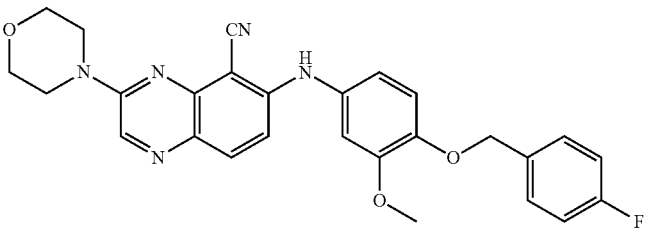 [SMILES: COc1cc(Nc2ccc3ncc(N4CCOCC4)nc3c2C#N)ccc1OCc1ccc(F)cc1]<br>6-((4-((4-fluorobenzyl)oxy)-3-methoxyphenyl)amino)-3-morpholinoquinoxaline-5-carbonitrile |
| 41 | 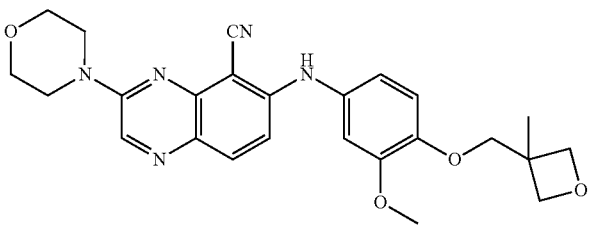 [SMILES: COc1cc(Nc2ccc3ncc(N4CCOCC4)nc3c2C#N)ccc1OCC1(C)COC1]<br>6-((3-methoxy-4-((3-methyloxetan-3-yl)methoxy)phenyl)amino)-3-morpholinoquinoxaline-5-carbonitrile |
| 42 | 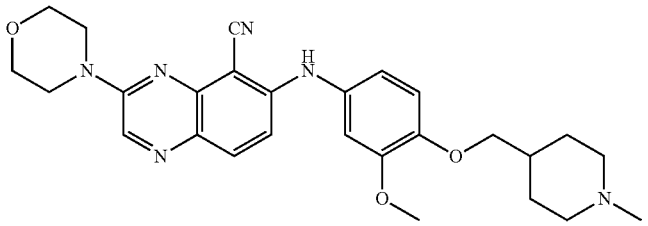 [SMILES: COc1cc(Nc2ccc3ncc(N4CCOCC4)nc3c2C#N)ccc1OCC1CCN(C)CC1]<br>6-((3-methoxy-4-((1-methylpiperidin-4-yl)methoxy)phenyl)amino)-3-morpholinoquinoxaline-5-carbonitrile |

TABLE 1-continued

Quinoxaline compounds

| Compound No. | Structure |
|---|---|
| 43 | 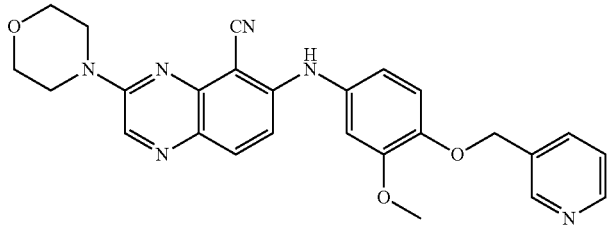 [SMILES: COc1cc(Nc2ccc3ncc(N4CCOCC4)nc3c2C#N)ccc1OCc1cccnc1]<br>6-((3-methoxy-4-(pyridin-3-ylmethoxy)phenyl)amino)-3-morpholinoquinoxaline-5-carbonitrile |
| 44 | 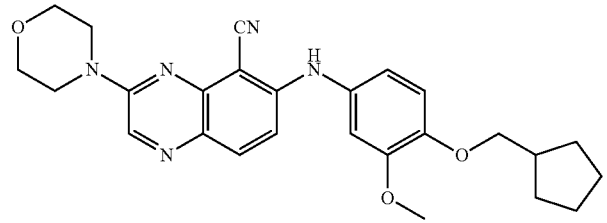 [SMILES: COc1cc(Nc2ccc3ncc(N4CCOCC4)nc3c2C#N)ccc1OCC1CCCC1]<br>6-((4-(cyclopentylmethoxy)-3-methoxyphenyl)amino)-3-morpholinoquinoxaline-5-carbonitrile |
| 45 | 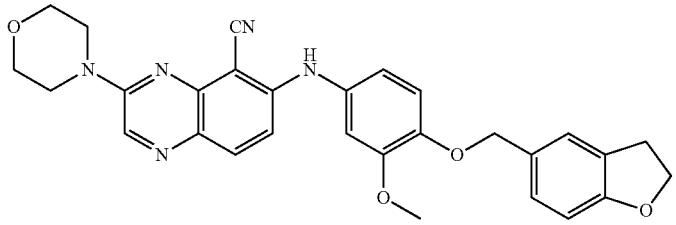 [SMILES: COc1cc(Nc2ccc3ncc(N4CCOCC4)nc3c2C#N)ccc1OCc1ccc2c(c1)CCO2]<br>6-((4-((2,3-dihydrobenzofuran-5-yl)methoxy)-3-methoxyphenyl)amino)-3-morpholinoquinoxaline-5-carbonitrile |
| 46 | 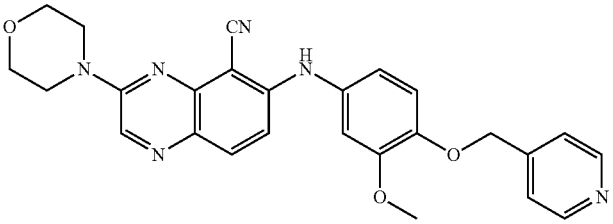 [SMILES: COc1cc(Nc2ccc3ncc(N4CCOCC4)nc3c2C#N)ccc1OCc1ccncc1]<br>6-((3-methoxy-4-(pyridin-4-ylmethoxy)phenyl)amino)-3-morpholinoquinoxaline-5-carbonitrile |
| 47 | 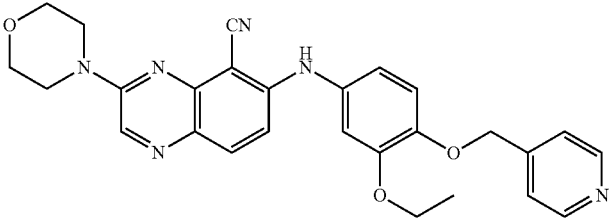 [SMILES: CCOc1cc(Nc2ccc3ncc(N4CCOCC4)nc3c2C#N)ccc1OCc1ccncc1]<br>6-((3-ethoxy-4-(pyridin-4-ylmethoxy)phenyl)amino)-3-morpholinoquinoxaline-5-carbonitrile |

TABLE 1-continued

Quinoxaline compounds

| Compound No. | Structure |
|---|---|
| 48 | 6-((3-methoxy-4-((1-methyl-1H-imidazol-2-yl)methoxy) phenyl)amino)-3-morpholinoquinoxaline-5-carbonitrile |
| 49 | 6-((4-((4-chlorobenzyl)oxy)-3-methoxyphenyl)amino)-3-morpholinoquinoxaline-5-carbonitrile |
| 50 | 6-((3-methoxy-4-((6-methoxypyridin-3-yl)methoxy)phenyl) amino)-3-morpholinoquinoxaline-5-carbonitrile |
| 51 | 6-((3-methoxy-4-(pyrazin-2-ylmethoxy)phenyl)amino)-3-morpholinoquinoxaline-5-carbonitrile |
| 52 | 6-((6-((4-methoxybenzyl)oxy)pyridin-3-yl)amino)-3-morpholinoquinoxaline-5-carbonitrile |

TABLE 1-continued

Quinoxaline compounds

| Compound No. | Structure |
|---|---|
| 53 | 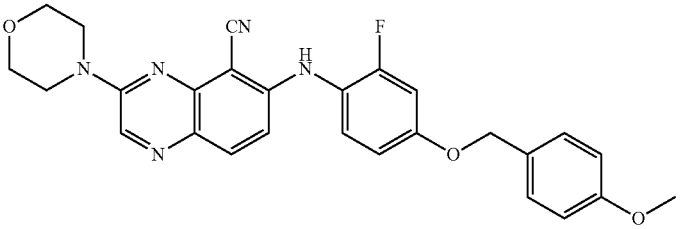 [SMILES: COc1ccc(COc2ccc(Nc3ccc4ncc(N5CCOCC5)nc4c3C#N)c(F)c2)cc1]<br>6-((2-fluoro-4-((4-methoxybenzyl)oxy)phenyl)amino)-3-morpholinoquinoxaline-5-carbonitrile |
| 54 | 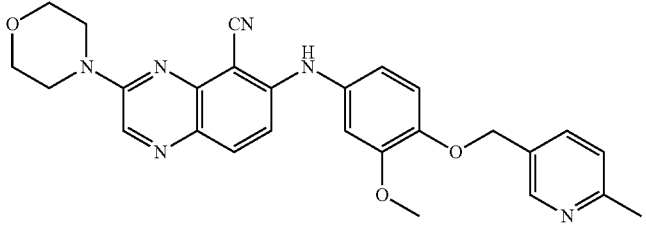 [SMILES: COc1cc(Nc2ccc3ncc(N4CCOCC4)nc3c2C#N)ccc1OCc1ccc(C)nc1]<br>6-((3-methoxy-4-((6-methylpyridin-3-yl)methoxy)phenyl)amino)-3-morpholinoquinoxaline-5-carbonitrile |
| 55 | 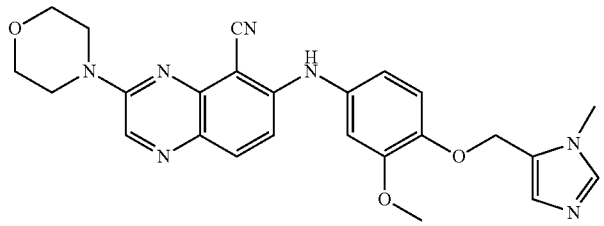 [SMILES: COc1cc(Nc2ccc3ncc(N4CCOCC4)nc3c2C#N)ccc1OCc1cncn1C]<br>6-((3-methoxy-4-((1-methyl-1H-imidazol-5-yl)methoxy)phenyl)amino)-3-morpholinoquinoxaline-5-carbonitrile |
| 56 | 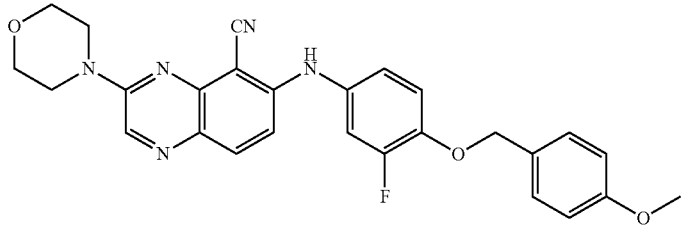<br>6-((3-fluoro-4-((4-methoxybenzyl)oxy)phenyl)amino)-3-morpholinoquinoxaline-5-carbonitrile |
| 57 | 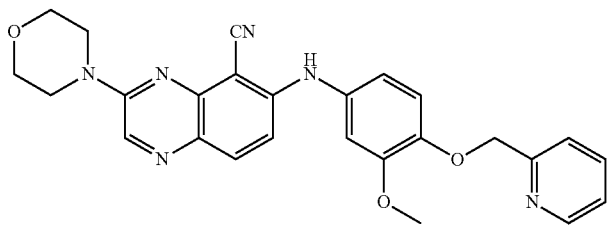<br>6-((3-methoxy-4-(pyridin-2-ylmethoxy)phenyl)amino)-3-morpholinoquinoxaline-5-carbonitrile |

TABLE 1-continued

Quinoxaline compounds

| Compound No. | Structure |
|---|---|
| 58 | 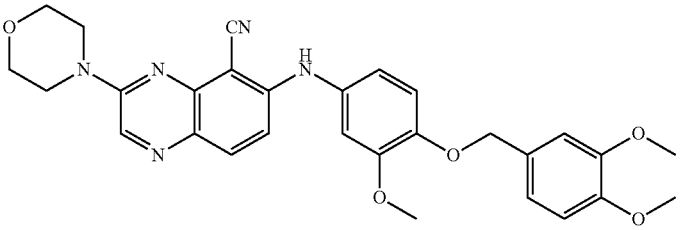 [SMILES: COc1ccc(COc2ccc(Nc3ccc4ncc(N5CCOCC5)nc4c3C#N)cc2OC)cc1OC]<br>6-((4-((3,4-dimethoxybenzyl)oxy)-3-methoxyphenyl)amino)-3-morpholinoquinoxaline-5-carbonitrile |
| 59 | 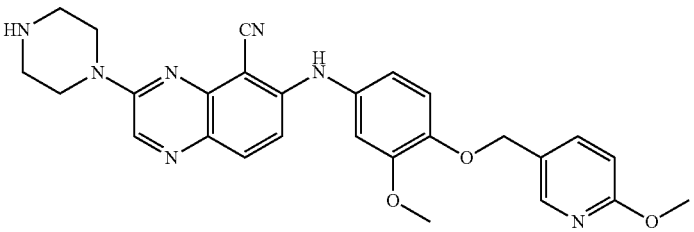 [SMILES: COc1ccc(COc2ccc(Nc3ccc4ncc(N5CCNCC5)nc4c3C#N)cc2OC)cn1]<br>6-((3-methoxy-4-((6-methoxypyridin-3-yl)methoxy)phenyl)amino)-3-(piperazin-1-yl)quinoxaline-5-carbonitrile |
| 60 | 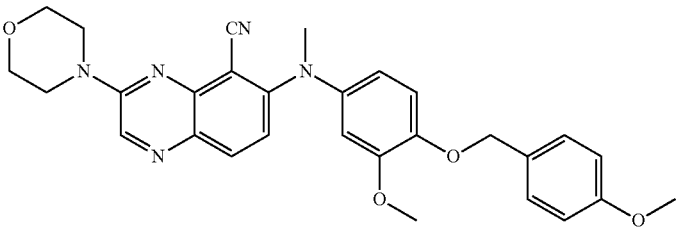 [SMILES: COc1ccc(COc2ccc(N(C)c3ccc4ncc(N5CCOCC5)nc4c3C#N)cc2OC)cc1]<br>6-((3-methoxy-4-((4-methoxybenzyl)oxy)phenyl)(methyl)amino)-3-morpholinoquinoxaline-5-carbonitrile |
| 61 | 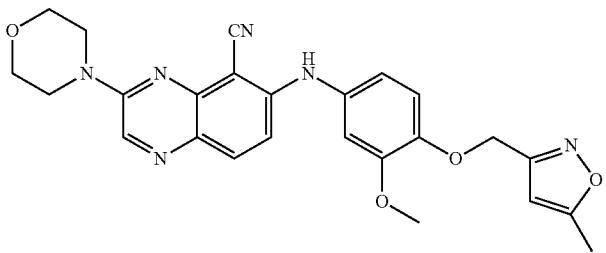 [SMILES: COc1cc(Nc2ccc3ncc(N4CCOCC4)nc3c2C#N)ccc1OCc1cc(C)on1]<br>6-((3-methoxy-4-((5-methylisoxazol-3-yl)methoxy)phenyl)amino)-3-morpholinoquinoxaline-5-carbonitrile |
| 62 | 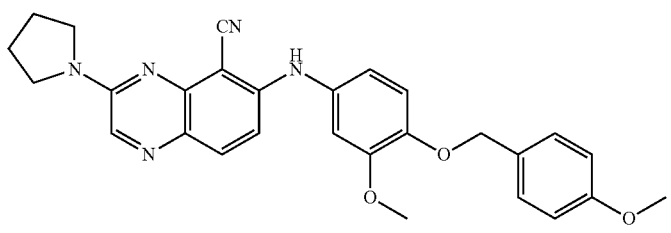 [SMILES: COc1ccc(COc2ccc(Nc3ccc4ncc(N5CCCC5)nc4c3C#N)cc2OC)cc1]<br>6-((3-methoxy-4-((4-methoxybenzyl)oxy)phenyl)amino)-3-(pyrrolidin-1-yl)quinoxaline-5-carbonitrile |

TABLE 1-continued

Quinoxaline compounds

| Compound No. | Structure |
|---|---|
| 63 | 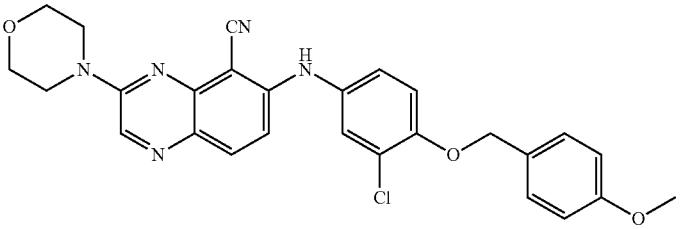 [SMILES: COc1ccc(COc2ccc(Nc3ccc4ncc(N5CCOCC5)nc4c3C#N)cc2Cl)cc1]<br>6-((3-chloro-4-((4-methoxybenzyl)oxy)phenyl)amino)-3-morpholinoquinoxaline-5-carbonitrile |
| 64 | 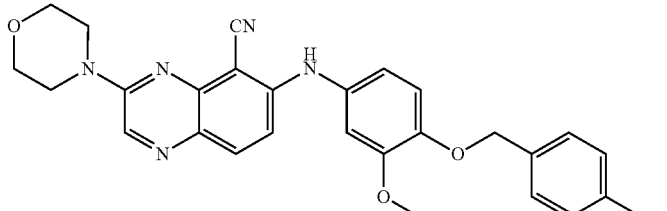<br>6-((4-((4-cyanobenzyl)oxy)-3-methoxyphenyl)amino)-3-morpholinoquinoxaline-5-carbonitrile |
| 65 | 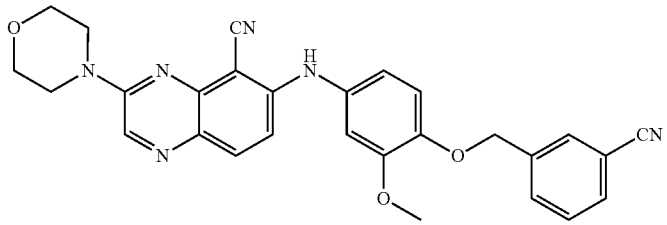 [SMILES: COc1cc(Nc2ccc3ncc(N4CCOCC4)nc3c2C#N)ccc1OCc1cccc(C#N)c1]<br>6-((4-((3-cyanobenzyl)oxy)-3-methoxyphenyl)amino)-3-morpholinoquinoxaline-5-carbonitrile |
| 66 | 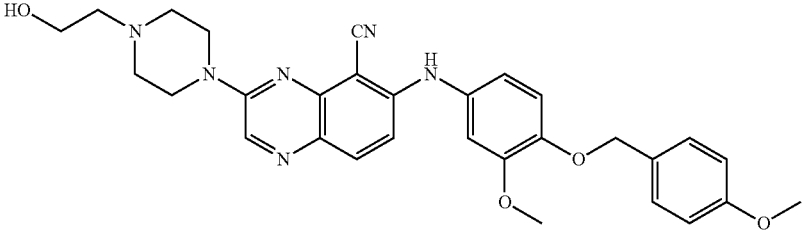 [SMILES: COc1ccc(COc2ccc(Nc3ccc4ncc(N5CCN(CCO)CC5)nc4c3C#N)cc2OC)cc1]<br>3-(4-(2-hydroxyethyl)piperazin-1-yl)-6-((3-methoxy-4-((4-methoxybenzyl)oxy)phenyl)amino)quinoxaline-5-carbonitrile |
| 67 | 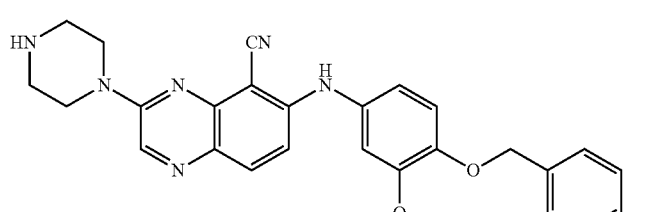<br>6-((3-methoxy-4-((6-methylpyridin-3-yl)methoxy)phenyl)amino)-3-(piperazin-1-yl)quinoxaline-5-carbonitrile |

TABLE 1-continued

Quinoxaline compounds

| Compound No. | Structure |
|---|---|
| 68 | 1-(8-cyano-7-((3-methoxy-4-((4-methoxybenzyl)oxy)phenyl)amino)quinoxalin-2-yl)piperidin-4-yl acetate |
| 69 | 6-((3-methoxy-4-((6-methoxypyridin-3-yl)methoxy)phenyl)amino)-3-(4-methylpiperidin-1-yl)quinoxaline-5-carbonitrile |
| 70 | 3-(1H-imidazol-1-yl)-6-((3-methoxy-4-((6-methoxypyridin-3-yl)methoxy)phenyl)amino)quinoxaline-5-carbonitrile |
| 71 | (1-(8-cyano-7-((3-methoxy-4-((4-methoxybenzyl)oxy)phenyl)amino)quinoxalin-2-yl)piperidin-4-yl)methyl acetate |

TABLE 1-continued

Quinoxaline compounds

| Compound No. | Structure |
|---|---|
| 72 | 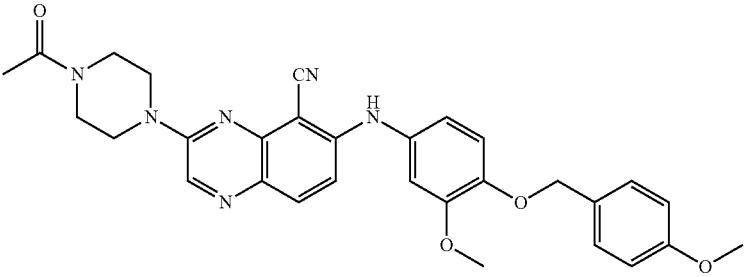 [SMILES: COc1ccc(COc2ccc(Nc3ccc4ncc(N5CCN(C(C)=O)CC5)nc4c3C#N)cc2OC)cc1]<br>3-(4-acetylpiperazin-1-yl)-6-((3-methoxy-4-((4-methoxybenzyl)oxy)phenyl)amino)quinoxaline-5-carbonitrile |
| 73 | 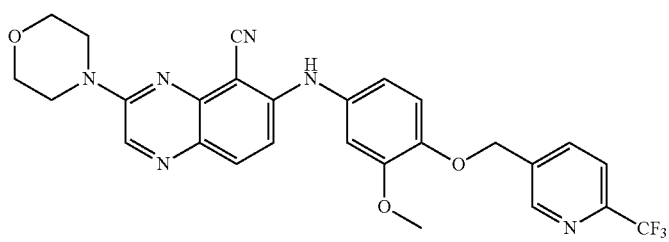 [SMILES: COc1cc(Nc2ccc3ncc(N4CCOCC4)nc3c2C#N)ccc1OCc1ccc(C(F)(F)F)nc1]<br>6-((3-methoxy-4-((6-(trifluoromethyl)pyridin-3-yl)methoxy)phenyl)amino)-3-morpholinoquinoxaline-5-carbonitrile |
| 74 | 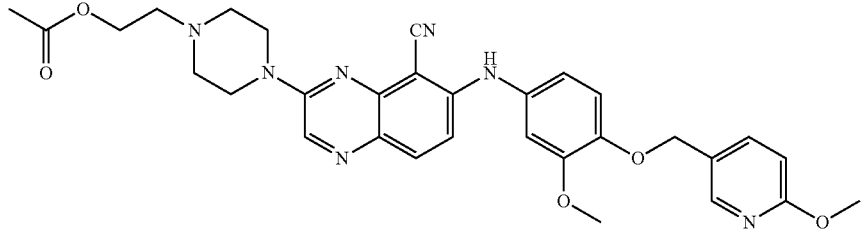 [SMILES: COc1ccc(COc2ccc(Nc3ccc4ncc(N5CCN(CCOC(C)=O)CC5)nc4c3C#N)cc2OC)cn1]<br>2-(4-(8-cyano-7-((3-methoxy-4-((6-methoxypyridin-3-yl)methoxy)phenyl)amino)quinoxalin-2-yl)piperazin-1-yl)ethyl acetate |
| 75 | 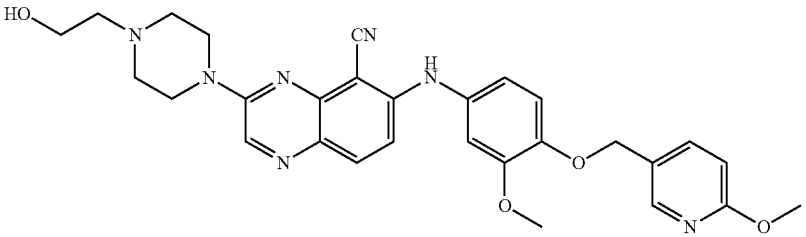 [SMILES: COc1ccc(COc2ccc(Nc3ccc4ncc(N5CCN(CCO)CC5)nc4c3C#N)cc2OC)cn1]<br>3-(4-(2-hydroxyethyl)piperazin-1-yl)-6-((3-methoxy-4-((6-methoxypyridin-3-yl)methoxy)phenyl)amino)quinoxaline-5-carbonitrile |
| 76 | 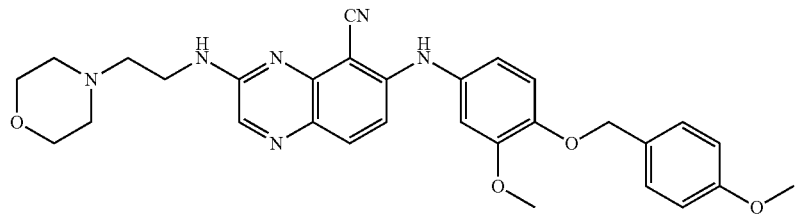 [SMILES: COc1ccc(COc2ccc(Nc3ccc4ncc(NCCN5CCOCC5)nc4c3C#N)cc2OC)cc1]<br>6-((3-methoxy-4-((4-methoxybenzyl)oxy)phenyl)amino)-3-((2-morpholinoethyl)amino)quinoxaline-5-carbonitrile |

TABLE 1-continued

Quinoxaline compounds

| Compound No. | Structure |
|---|---|
| 77 | 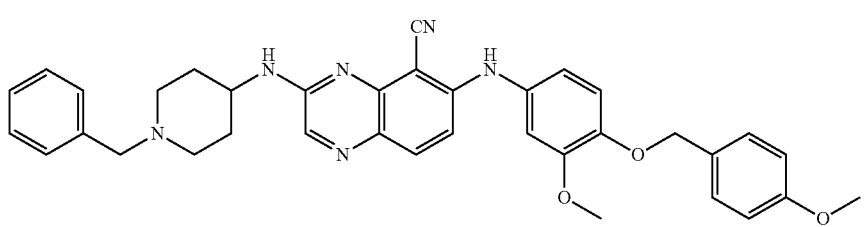 [SMILES: COc1ccc(COc2ccc(Nc3ccc4ncc(NC5CCN(Cc6ccccc6)CC5)nc4c3C#N)cc2OC)cc1]<br>3-((1-benzylpiperidin-4-yl)amino)-6-((3-methoxy-4-((4-methoxybenzyl)oxy)phenyl)amino)quinoxaline-5-carbonitrile |
| 78 | 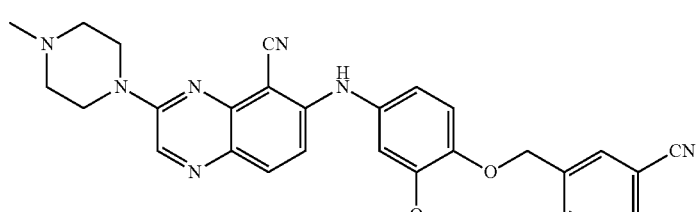<br>6-((4-((3-cyanobenzyl)oxy)-3-methoxyphenyl)amino)-3-(4-methylpiperazin-1-yl)quinoxaline-5-carbonitrile |
| 79 | 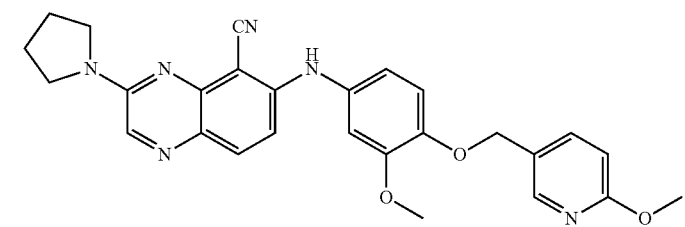 [SMILES: COc1ccc(COc2ccc(Nc3ccc4ncc(N5CCCC5)nc4c3C#N)cc2OC)cn1]<br>6-((3-methoxy-4-((6-methoxypyridin-3-yl)methoxy)phenyl)amino)-3-(pyrrolidin-1-yl)quinoxaline-5-carbonitrile |
| 80 | 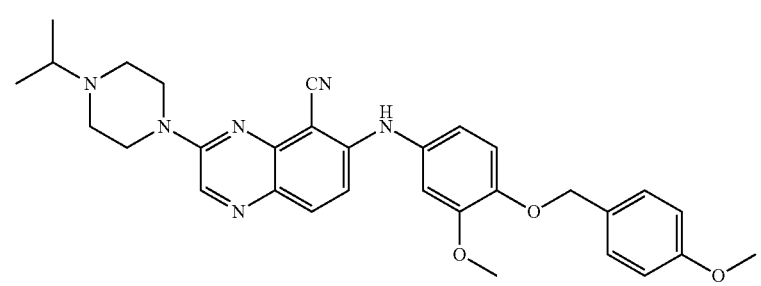 [SMILES: COc1ccc(COc2ccc(Nc3ccc4ncc(N5CCN(C(C)C)CC5)nc4c3C#N)cc2OC)cc1]<br>3-(4-isopropylpiperazin-1-yl)-6-((3-methoxy-4-((4-methoxybenzyl)oxy)phenyl)amino)quinoxaline-5-carbonitrile |
| 81 | 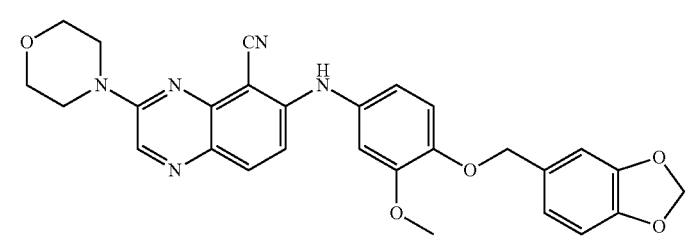 [SMILES: COc1cc(Nc2ccc3ncc(N4CCOCC4)nc3c2C#N)ccc1OCc1ccc2c(c1)OCO2]<br>6-((4-(benzo[d][1,3]dioxol-5-ylmethoxy)-3-methoxyphenyl)amino)-3-morpholinoquinoxaline-5-carbonitrile |

TABLE 1-continued

Quinoxaline compounds

| Compound No. | Structure |
|---|---|
| 82 | 3-(4-(dimethylamino)piperidin-1-yl)-6-((3-methoxy-4-((6-methoxy-pyridin-3-yl)methoxy)phenyl)amino)quinoxaline-5-carbonitrile |
| 83 | 3-(azetidin-1-yl)-6-((3-methoxy-4-((4-methoxybenzyl)oxy)phenyl)amino)quinoxaline-5-carbonitrile |
| 84 | 6-((4-((3-cyanobenzyl)oxy)-3-methoxyphenyl)amino)-3-(4-(dimethylamino)piperidin-1-yl)quinoxaline-5-carbonitrile |
| 85 | 3-(4-(dimethylamino)piperidin-1-yl)-6-((4-((3-fluoro-4-methoxybenzyl)oxy)-3-methoxyphenyl)amino)quinoxaline-5-carbonitrile |

TABLE 1-continued

Quinoxaline compounds

| Compound No. | Structure |
|---|---|
| 86 | 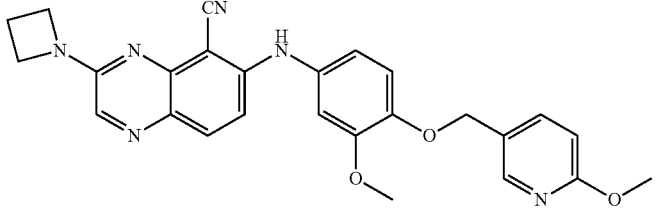 [SMILES: COc1ccc(COc2ccc(Nc3ccc4ncc(N5CCC5)nc4c3C#N)cc2OC)cn1]<br>3-(azetidin-1-yl)-6-((3-methoxy-4-((6-methoxpyridin-3-yl)methoxy)phenyl)amino)quinoxaline-5-carbonitrile |
| 87 | 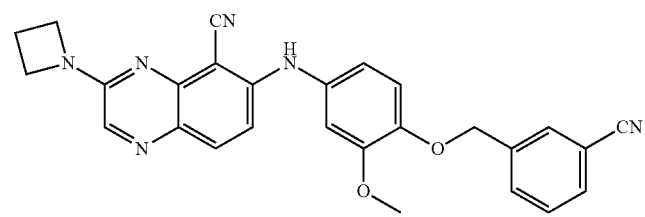 [SMILES: COc1cc(Nc2ccc3ncc(N4CCC4)nc3c2C#N)ccc1OCc1cccc(C#N)c1]<br>3-(azetidin-1-yl)-6-((4-((3-cyanobenzyl)oxy)-3-methoxyphenyl)amino)quinoxaline-5-carbonitrile |
| 88 | 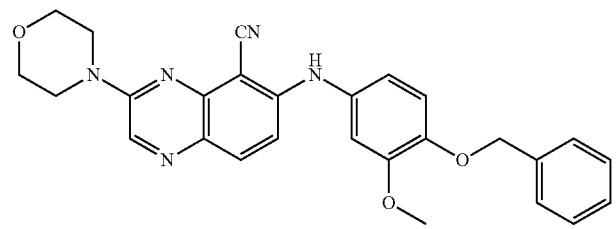<br>6-((4-(benzyloxy)-3-methoxyphenyl)amino)-3-morpholinoquinoxaline-5-carbonitrile |
| 89 | 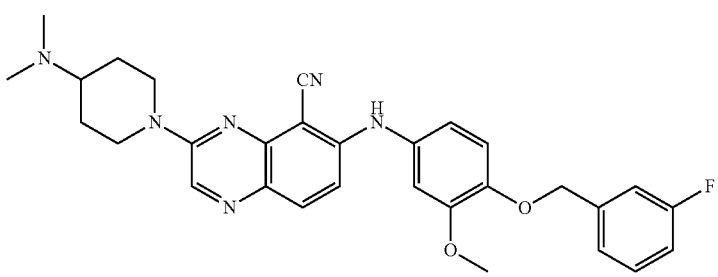 [SMILES: COc1cc(Nc2ccc3ncc(N4CCC(N(C)C)CC4)nc3c2C#N)ccc1OCc1cccc(F)c1]<br>3-(4-(dimethylamino)piperidin-1-yl)-6-((4-((3-fluorobenzyl)oxy)-3-methoxyphenyl)amino)quinoxaline-5-carbonitrile |
| 90 | 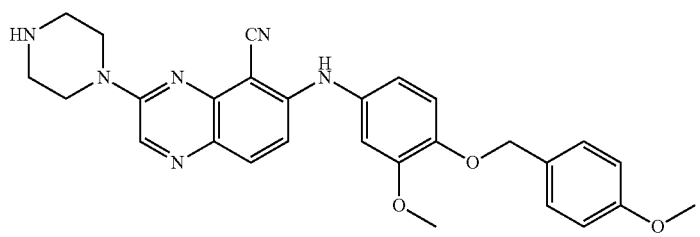 [SMILES: COc1ccc(COc2ccc(Nc3ccc4ncc(N5CCNCC5)nc4c3C#N)cc2OC)cc1]<br>6-((3-methoxy-4-((4-methoxybenzyl)oxy)phenyl)amino)-3-(piperazin-1-yl)quinoxaline-5-carbonitrile |

TABLE 1-continued

Quinoxaline compounds

| Compound No. | Structure |
|---|---|
| 91 | 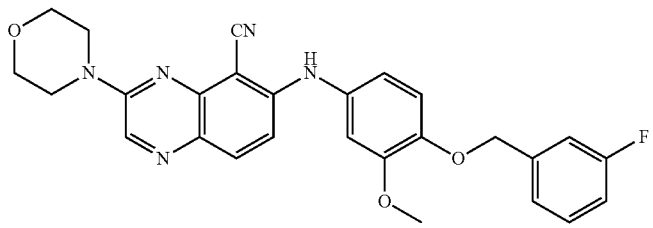 [SMILES: COc1cc(Nc2ccc3ncc(N4CCOCC4)nc3c2C#N)ccc1OCc1cccc(F)c1]<br>6-((4-((3-fluorobenzyl)oxy)-3-methoxyphenyl)amino)-3-morpholinoquinoxaline-5-carbonitrile |
| 92 | 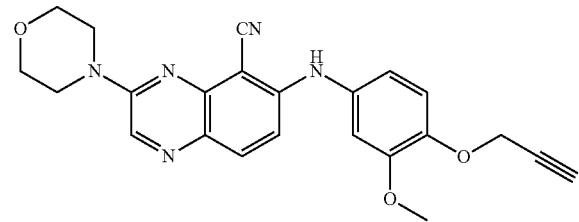 [SMILES: C#CCOc1ccc(Nc2ccc3ncc(N4CCOCC4)nc3c2C#N)cc1OC]<br>6-((3-methoxy-4-(prop-2-yn-1-yloxy)phenyl)amino)-3-morpholinoquinoxaline-5-carbonitrile |
| 93 | 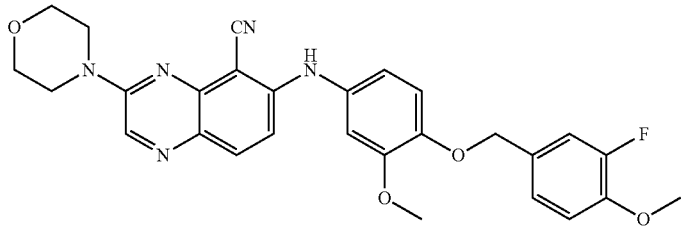 [SMILES: COc1ccc(COc2ccc(Nc3ccc4ncc(N5CCOCC5)nc4c3C#N)cc2OC)cc1F]<br>6-((4-((3-fluoro-4-methoxybenzyl)oxy)-3-methoxyphenyl)amino)-3-morpholinoquinoxaline-5-carbonitrile |
| 94 | 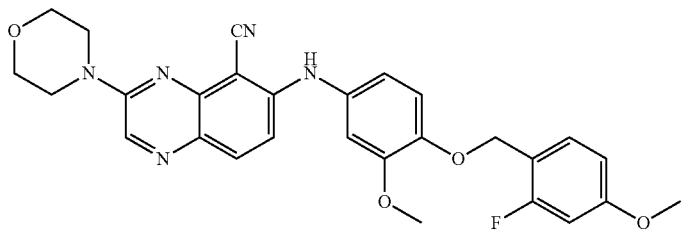 [SMILES: COc1ccc(COc2ccc(Nc3ccc4ncc(N5CCOCC5)nc4c3C#N)cc2OC)c(F)c1]<br>6-((4-((2-fluoro-4-methoxybenzyl)oxy)-3-methoxyphenyl)amino)-3-morpholinoquinoxaline-5-carbonitrile |
| 95 | 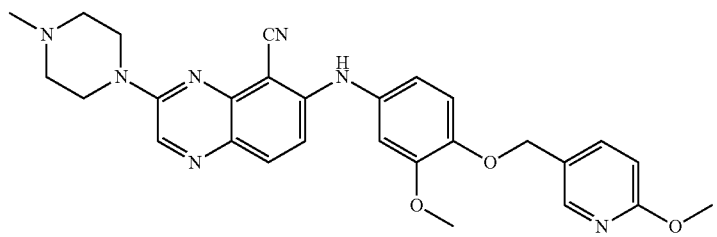<br>6-((3-methoxy-4-((6-methoxypyridin-3-yl)methoxy)phenyl)amino)-3-(4-methylpiperazin-1-yl)quinoxaline-5-carbonitrile |

TABLE 1-continued

Quinoxaline compounds

| Compound No. | Structure |
|---|---|
| 96 | 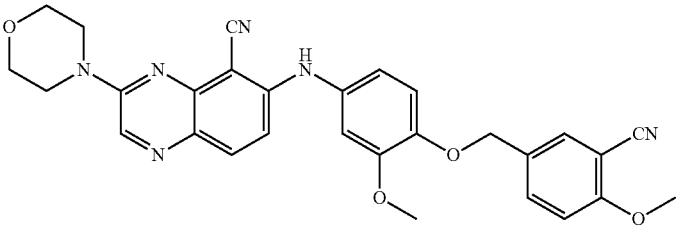 [SMILES: COc1ccc(COc2ccc(Nc3ccc4ncc(N5CCOCC5)nc4c3C#N)cc2OC)cc1C#N]<br>6-((4-((3-cyano-4-methoxybenzyl)oxy)-3-methoxyphenyl)amino)-3-morpholinoquinoxaline-5-carbonitrile |
| 97 | 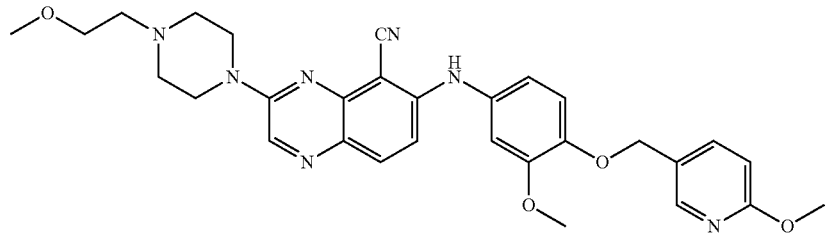<br>6-((3-methoxy-4-((6-methoxypyridin-3-yl)methoxy)phenyl)amino)-3-(4-(2-methoxyethyl)piperazin-1-yl)quinoxaline-5-carbonitrile |
| 98 | 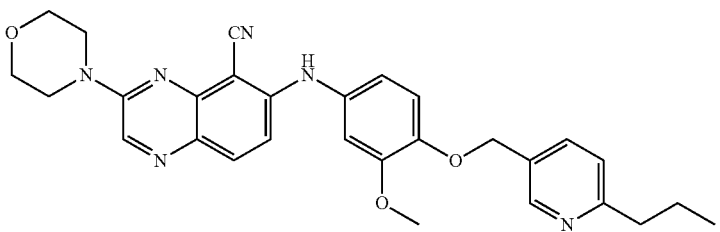 [SMILES: CCCc1ccc(COc2ccc(Nc3ccc4ncc(N5CCOCC5)nc4c3C#N)cc2OC)cn1]<br>6-((3-methoxy-4-((6-propylpyridin-3-yl)methoxy)phenyl)amino)-3-morpholinoquinoxaline-5-carbonitrile |
| 99 | 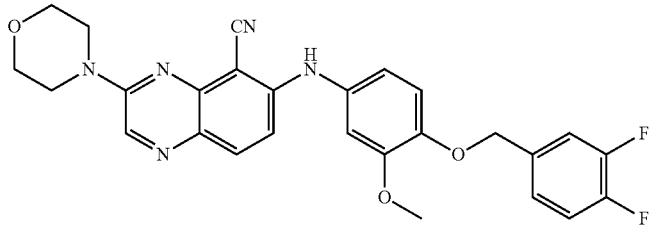 [SMILES: COc1cc(Nc2ccc3ncc(N4CCOCC4)nc3c2C#N)ccc1OCc1ccc(F)c(F)c1]<br>6-((4-((3,4-difluorobenzyl)oxy)-3-methoxyphenyl)amino)-3-morpholinoquinoxaline-5-carbonitrile |
| 100 | 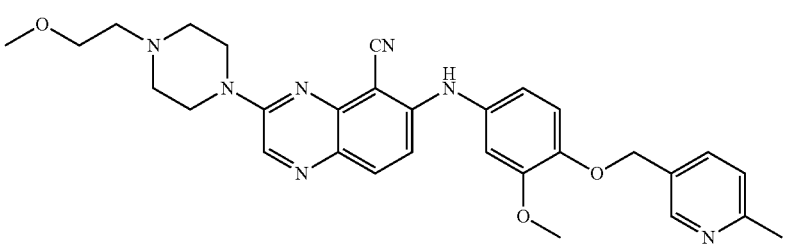<br>6-((3-methoxy-4-((6-methylpyridin-3-yl)methoxy)phenyl)amino)-3-(4-(2-methoxyethyl)piperazin-1-yl)quinoxaline-5-carbonitrile |

TABLE 1-continued

Quinoxaline compounds

| Compound No. | Structure |
| --- | --- |
| 101 | 6-((4-((6-ethylpyridin-3-yl)methoxy)-3-methoxyphenyl)amino)-3-morpholinoquinoxaline-5-carbonitrile |
| 102 | 6-((3-methoxy-4-((6-methoxypyridin-3-yl)methoxy)phenyl)amino)-3-(4-morpholinopiperidin-1-yl)quinoxaline-5-carbonitrile |
| 103 | 6-((4-((6-isopropylpyridin-3-yl)methoxy)-3-methoxyphenyl)amino)-3-morpholinoquinoxaline-5-carbonitrile |
| 104 | 6-((4-((6-(dimethylamino)pyridin-3-yl)methoxy)-3-methoxyphenyl)amino)-3-morpholinoquinoxaline-5-carbonitrile |

TABLE 1-continued

Quinoxaline compounds

| Compound No. | Structure |
|---|---|
| 105 | 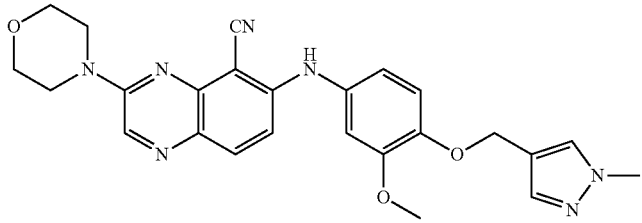 [SMILES: COc1cc(Nc2ccc3ncc(N4CCOCC4)nc3c2C#N)ccc1OCc1cnn(C)c1]<br>6-((3-methoxy-4-((1-methyl-1H-pyrazol-4-yl)methoxy)phenyl)amino)-3-morpholinoquinoxaline-5-carbonitrile |
| 106 | 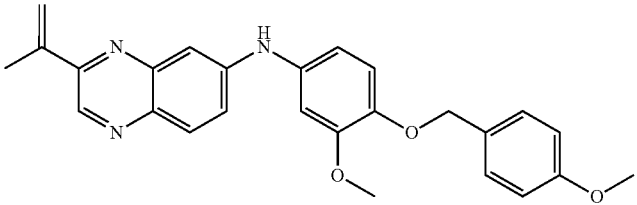 [SMILES: C=C(C)c1cnc2ccc(Nc3ccc(OCc4ccc(OC)cc4)c(OC)c3)cc2n1]<br>N-(3-methoxy-4-((4-methoxybenzyl)oxy)phenyl)-3-(prop-1-en-2-yl)quinoxalin-6-amine |
| 107 | 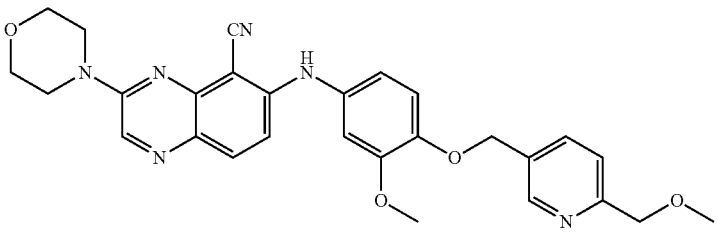 [SMILES: COCc1ccc(COc2ccc(Nc3ccc4ncc(N5CCOCC5)nc4c3C#N)cc2OC)cn1]<br>6-((3-methoxy-4-((6-(methoxymethyl)pyridin-3-yl)methoxy)phenyl)amino)-3-morpholinoquinoxaline-5-carbonitrile |
| 108 | 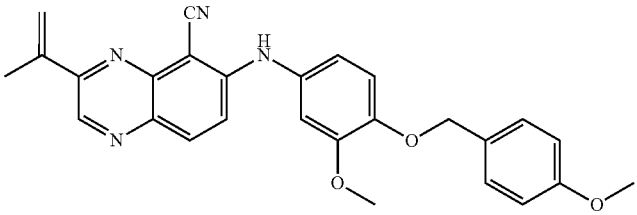 [SMILES: C=C(C)c1cnc2ccc(Nc3ccc(OCc4ccc(OC)cc4)c(OC)c3)c(C#N)c2n1]<br>6-((3-methoxy-4-((4-methoxybenzyl)oxy)phenyl)amino)-3-(prop-1-en-2-yl)quinoxaline-5-carbonitrile |
| 109 | 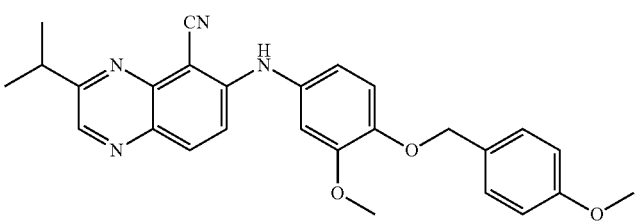<br>3-isopropyl-6-((3-methoxy-4-((4-methoxybenzyl)oxy)phenyl)amino)quinoxaline-5-carbonitrile |

TABLE 1-continued

Quinoxaline compounds

| Compound No. | Structure |
|---|---|
| 110 | 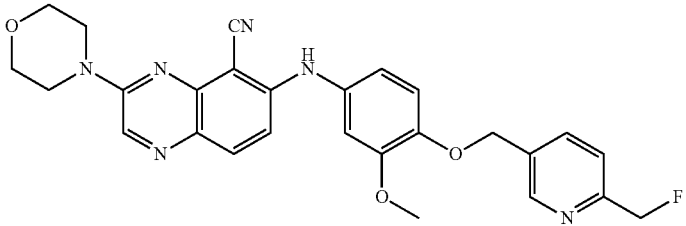 [SMILES: COc1cc(Nc2ccc3ncc(N4CCOCC4)nc3c2C#N)ccc1OCc1ccc(CF)nc1]<br>6-((4-((6-(fluoromethyl)pyridin-3-yl)methoxy)-3-methoxyphenyl)amino)-3-morpholinoquinoxaline-5-carbonitrile |
| 111 | 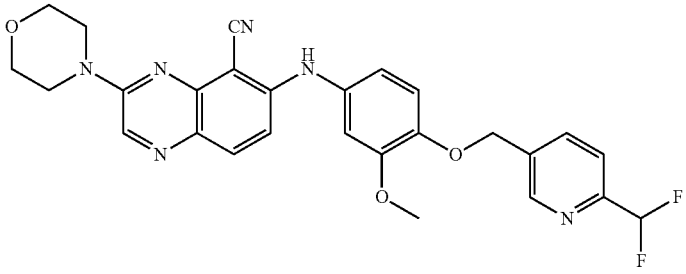 [SMILES: COc1cc(Nc2ccc3ncc(N4CCOCC4)nc3c2C#N)ccc1OCc1ccc(C(F)F)nc1]<br>6-((4-((6-(difluoromethyl)pyridin-3-yl)methoxy)-3-methoxyphenyl)amino)-3-morpholinoquinoxaline-5-carbonitrile |
| 112 | 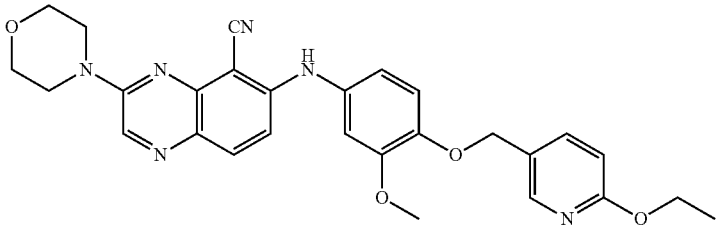 [SMILES: CCOc1ccc(COc2ccc(Nc3ccc4ncc(N5CCOCC5)nc4c3C#N)cc2OC)cn1]<br>6-((4-((6-ethoxypyridin-3-yl)methoxy)-3-methoxyphenyl)amino)-3-morpholinoquinoxaline-5-carbonitrile |
| 113 | 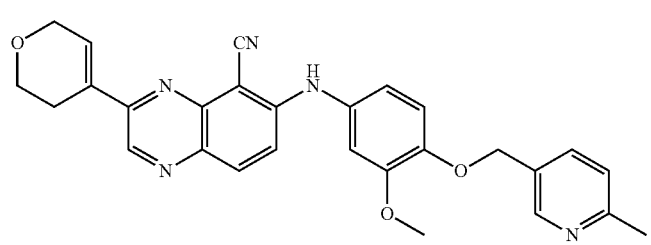 [SMILES: COc1cc(Nc2ccc3ncc(C4=CCOCC4)nc3c2C#N)ccc1OCc1ccc(C)nc1]<br>3-(3,6-dihydro-2H-pyran-4-yl)-6-((3-methoxy-4-((6-methylpyridin-3-yl)methoxy)phenyl)amino)quinoxaline-5-carbonitrile |
| 114 | 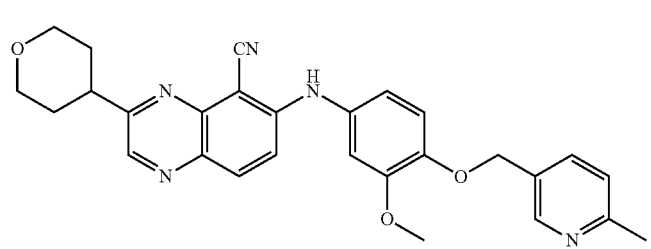 [SMILES: COc1cc(Nc2ccc3ncc(C4CCOCC4)nc3c2C#N)ccc1OCc1ccc(C)nc1]<br>6-((3-methoxy-4-((6-methylpyridin-3-yl)methoxy)phenyl)amino)-3-(tetrahydro-2H-pyran-4-yl)quinoxaline-5-carbonitrile |

TABLE 1-continued

Quinoxaline compounds

| Compound No. | Structure |
|---|---|
| 115 | 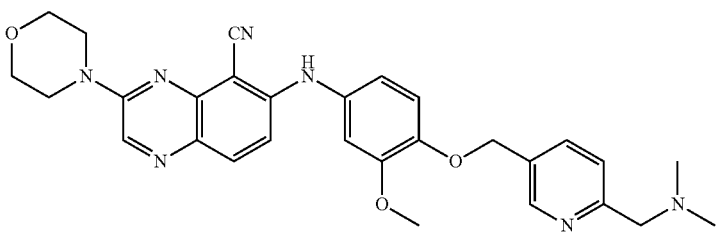 [SMILES: COc1cc(Nc2ccc3ncc(N4CCOCC4)nc3c2C#N)ccc1OCc1ccc(CN(C)C)nc1]<br>6-((4-((6-((dimethylamino)methyl)pyridin-3-yl)methoxy)-3-methoxyphenyl)amino)-3-morpholinoquinoxaline-5-carbonitrile |
| 116 | 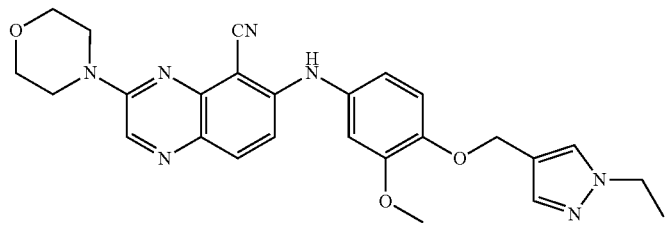 [SMILES: CCn1cc(COc2ccc(Nc3ccc4ncc(N5CCOCC5)nc4c3C#N)cc2OC)cn1]<br>6-((3-methoxy-4-((1-ethyl-1H-pyrazol-4-yl)methoxy)phenyl)amino)-3-morpholinoquinoxaline-5-carbonitrile |
| 117 | 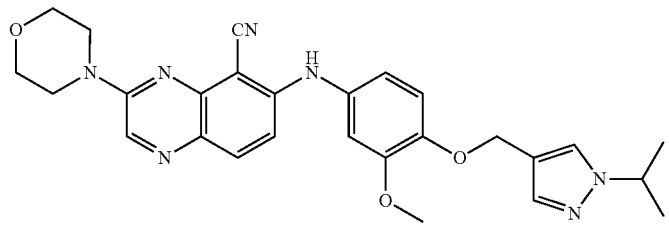 [SMILES: COc1cc(Nc2ccc3ncc(N4CCOCC4)nc3c2C#N)ccc1OCc1cnn(C(C)C)c1]<br>6-((3-methoxy-4-((1-propyl-1H-pyrazol-4-yl)methoxy)phenyl)amino)-3-morpholinoquinoxaline-5-carbonitrile |
| 118 | 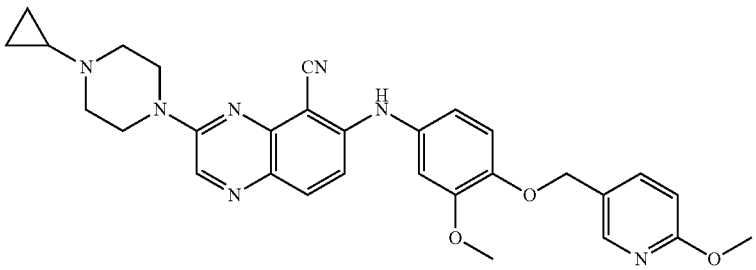 [SMILES: COc1ccc(COc2ccc(Nc3ccc4ncc(N5CCN(C6CC6)CC5)nc4c3C#N)cc2OC)cn1]<br>3-(4-cyclopropylpiperazin-1-yl)-6-((3-methoxy-4-((6-methoxypyridin-3-yl)methoxy)phenyl)amino)quinoxaline-5-carbonitrile |
| 119 | 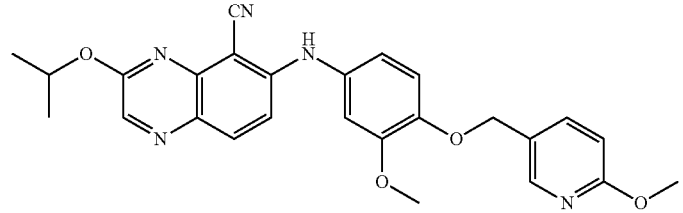 [SMILES: COc1ccc(COc2ccc(Nc3ccc4ncc(OC(C)C)nc4c3C#N)cc2OC)cn1]<br>3-isopropoxy-6-((3-methoxy-4-((6-methoxypyridin-3-yl)methoxy)phenyl)amino)quinoxaline-5-carbonitrile |

TABLE 1-continued

Quinoxaline compounds

| Compound No. | Structure |
|---|---|
| 120 | 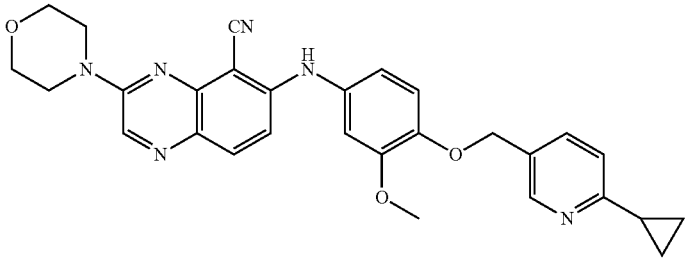 [SMILES: COc1cc(Nc2ccc3ncc(N4CCOCC4)nc3c2C#N)ccc1OCc1ccc(C2CC2)nc1]<br>6-((4-((6-cyclopropylpyridin-3-yl)methoxy)-3-methoxyphenyl)amino)-3-morpholinoquinoxaline-5-carbonitrile |
| 121 | 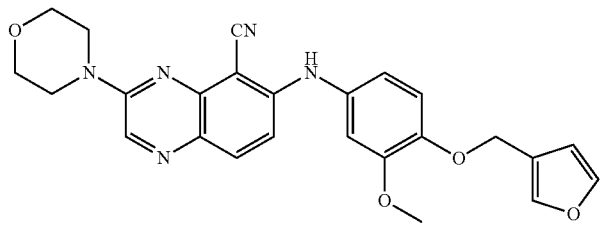 [SMILES: COc1cc(Nc2ccc3ncc(N4CCOCC4)nc3c2C#N)ccc1OCc1ccoc1]<br>6-((4-(furan-3-ylmethoxy)-3-methoxyphenyl)amino)-3-morpholinoquinoxaline-5-carbonitrile |
| 122 | 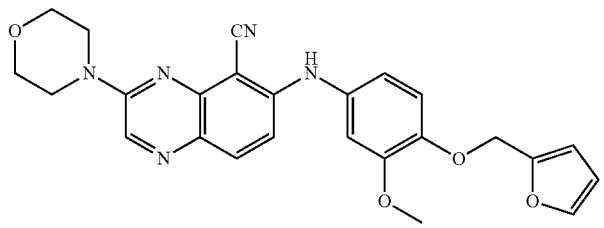 [SMILES: COc1cc(Nc2ccc3ncc(N4CCOCC4)nc3c2C#N)ccc1OCc1ccco1]<br>6-((4-(furan-2-ylmethoxy)-3-methoxyphenyl)amino)-3-morpholinoquinoxaline-5-carbonitrile |
| 123 | 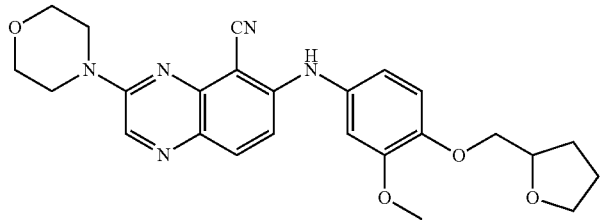<br>6-((3-methoxy-4-((tetrahydrofuran-2-yl)methoxy)phenyl)amino)-3-morpholinoquinoxaline-5-carbonitrile |
| 124 | 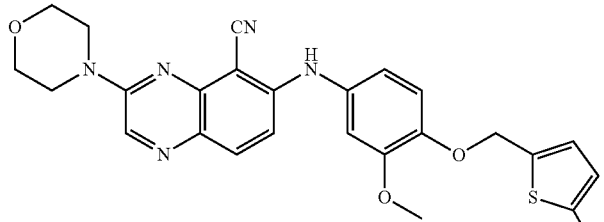<br>6-((3-methoxy-4-((5-methylthiophen-2-yl)methoxy)phenyl)amino)-3-morpholinoquinoxaline-5-carbonitrile |

TABLE 1-continued

Quinoxaline compounds

| Compound No. | Structure |
|---|---|
| 125 | 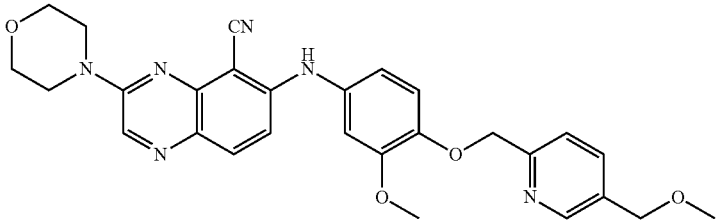 [SMILES: COCc1ccc(COc2ccc(Nc3ccc4ncc(N5CCOCC5)nc4c3C#N)cc2OC)nc1]<br>6-((3-methoxy-4-((5-(methoxymethyl)pyridin-2-yl)methoxy)phenyl)amino)-3-morpholinoquinoxaline-5-carbonitrile |
| 126 | 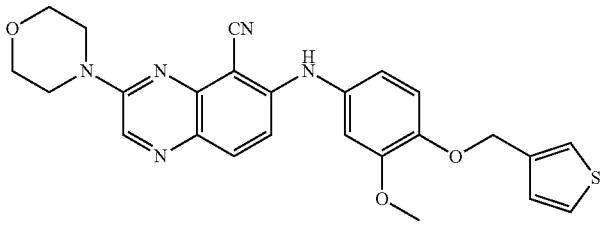 [SMILES: COc1cc(Nc2ccc3ncc(N4CCOCC4)nc3c2C#N)ccc1OCc1ccsc1]<br>6-((3-methoxy-4-(thiophen-3-ylmethoxy)phenyl)amino)-3-morpholinoquinoxaline-5-carbonitrile |
| 127 | 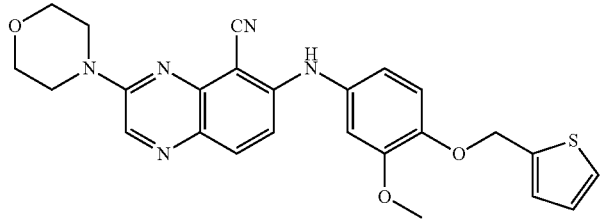<br>6-((3-methoxy-4-(thiophen-2-ylmethoxy)phenyl)amino)-3-morpholinoquinoxaline-5-carbonitrile |
| 128 | 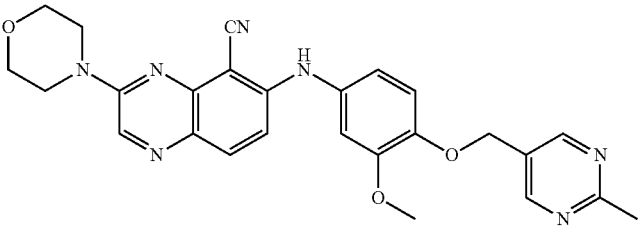 [SMILES: COc1cc(Nc2ccc3ncc(N4CCOCC4)nc3c2C#N)ccc1OCc1cnc(C)nc1]<br>6-((3-methoxy-4-((2-methylpyrimidin-5-yl)methoxy)phenyl)amino)-3-morpholinoquinoxaline-5-carbonitrile |
| 129 | 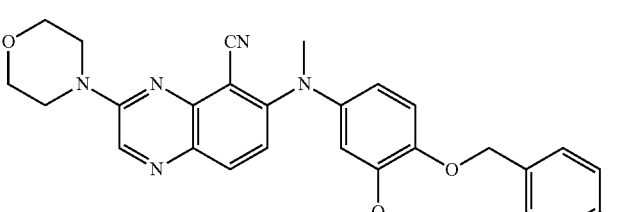<br>6-((3-methoxy-4-((6-methylpyridin-3-yl)methoxy)phenyl)(methyl)amino)-3-morpholinoquinoxaline-5-carbonitrile |

TABLE 1-continued

Quinoxaline compounds

| Compound No. | Structure |
|---|---|
| 130 | 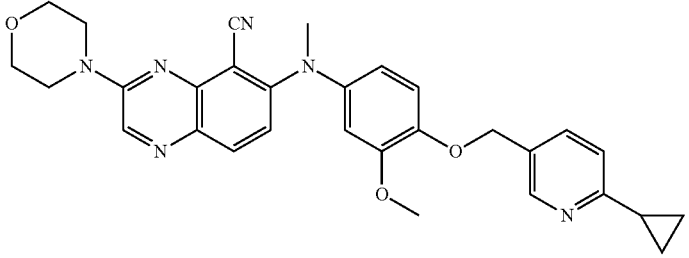 [SMILES: COc1cc(N(C)c2ccc3ncc(N4CCOCC4)nc3c2C#N)ccc1OCc1ccc(C2CC2)nc1]<br>6-((4-((6-cyclopropylpyridin-3-yl)methoxy)-3-methoxyphenyl)(methyl)amino)-3-morpholinoquinoxaline-5-carbonitrile |
| 131 | 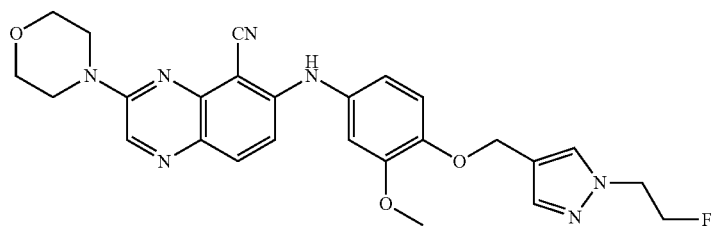 [SMILES: COc1cc(Nc2ccc3ncc(N4CCOCC4)nc3c2C#N)ccc1OCc1cnn(CCF)c1]<br>6-((4-((1-(2-fluoroethyl)-1H-pyrazol-4-yl)methoxy)-3-methoxyphenyl)amino)-3-morpholinoquinoxaline-5-carbonitrile |
| 132 | 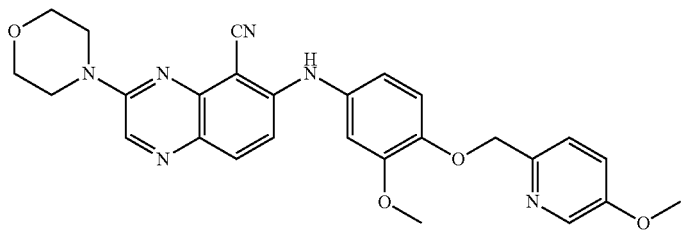 [SMILES: COc1ccc(COc2ccc(Nc3ccc4ncc(N5CCOCC5)nc4c3C#N)cc2OC)nc1]<br>6-((3-methoxy-4-((5-methoxypyridin-2-yl)methoxy)phenyl)amino)-3-morpholinoquinoxaline-5-carbonitrile |
| 133 | 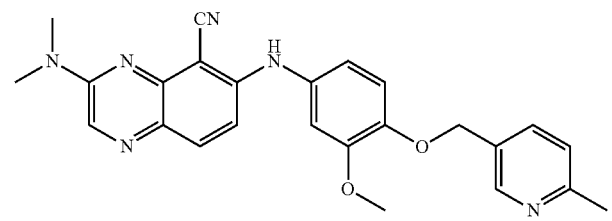<br>3-(dimethylamino)-6-((3-methoxy-4-((6-methylpyridin-3-yl)methoxy)phenyl)amino)quinoxaline-5-carbonitrile |
| 134 | 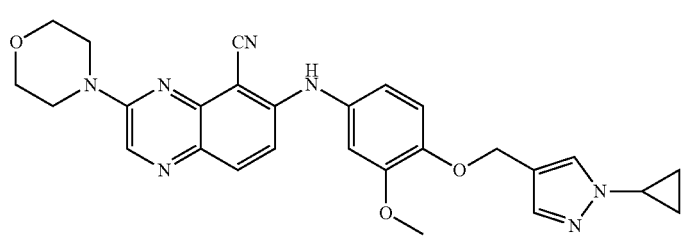 [SMILES: COc1cc(Nc2ccc3ncc(N4CCOCC4)nc3c2C#N)ccc1OCc1cnn(C2CC2)c1]<br>6-((4-((1-cyclopropyl-1H-pyrazol-4-yl)methoxy)-3-methoxyphenyl)amino)-3-morpholinoquinoxaline-5-carbonitrile |

TABLE 1-continued

Quinoxaline compounds

| Compound No. | Structure |
|---|---|
| 135 | 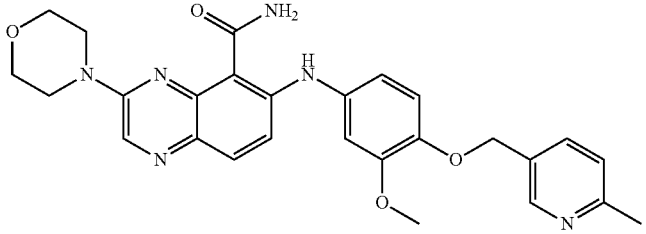 [SMILES: COc1cc(Nc2ccc3ncc(N4CCOCC4)nc3c2C(N)=O)ccc1OCc1ccc(C)nc1]<br>6-((3-methoxy-4-((6-methylpyridin-3-yl)methoxy)phenyl)amino)-3-morpholinoquinoxaline-5-carboxamide |
| 136 | 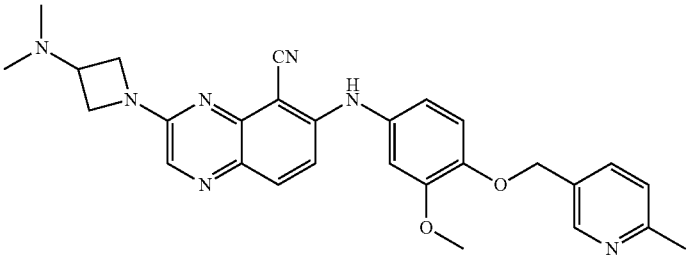<br>3-(3-(dimethylamino)azetidin-1-yl)-6-((3-methoxy-4-((6-methylpyridin-3-yl)methoxy)phenyl)amino)quinoxaline-5-carbonitrile |
| 137 | 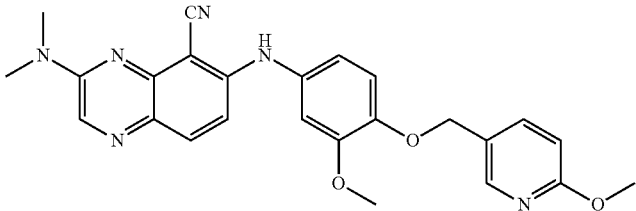<br>3-(dimethylamino)-6-((3-methoxy-4-((6-methoxypyridin-3-yl)methoxy)phenyl)amino)quinoxaline-5-carbonitrile |
| 138 | 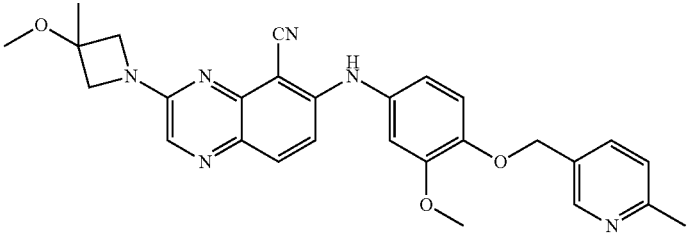<br>3-(3-methoxy-3-methylazetidin-1-yl)-6-((3-methoxy-4-((6-methyl-pyridin-3-yl)methoxy)phenyl)amino)quinoxaline-5-carbonitrile |
| 139 | 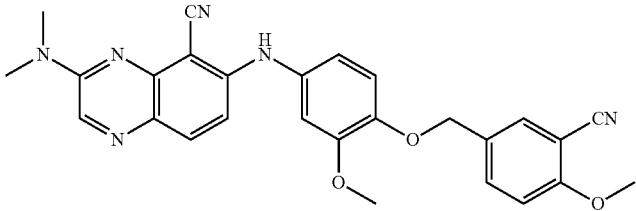<br>6-((4-((3-cyano-4-methoxybenzyl)oxy)-3-methoxyphenyl)amino)-3-(dimethylamino)quinoxaline-5-carbonitrile |

TABLE 1-continued

Quinoxaline compounds

| Compound No. | Structure |
|---|---|
| 140 | 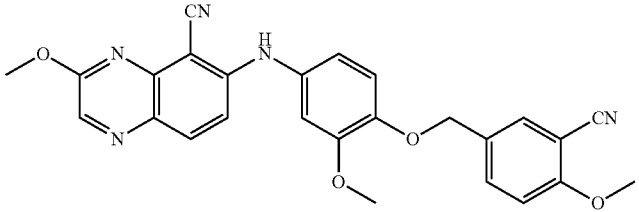<br>6-((4-((3-cyano-4-methoxybenzyl)oxy)-3-methoxyphenyl)amino)-3-methoxyquinoxaline-5-carbonitrile |
| 141 | 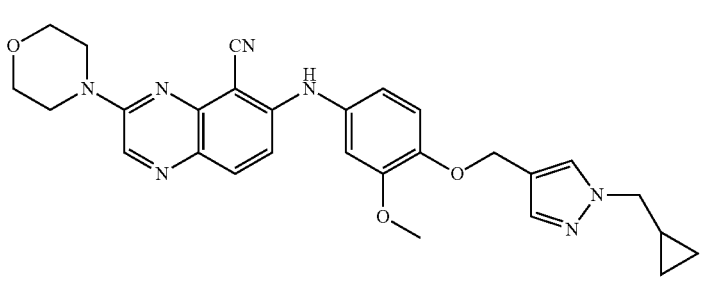 [SMILES: COc1cc(Nc2ccc3ncc(N4CCOCC4)nc3c2C#N)ccc1OCc1cnn(CC2CC2)c1]<br>6-((4-((1-(cyclopropylmethyl)-1H-pyrazol-4-yl)methoxy)-3-methoxyphenyl)amino)-3-morpholinoquinoxaline-5-carbonitrile |
| 142 | 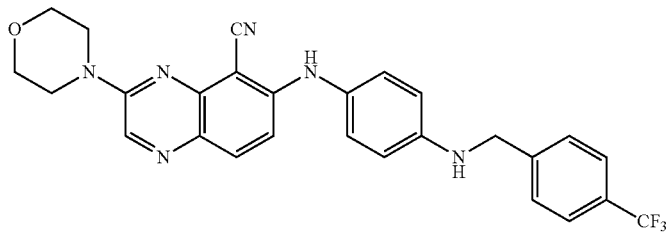 [SMILES: N#Cc1c(Nc2ccc(NCc3ccc(C(F)(F)F)cc3)cc2)ccc2ncc(N3CCOCC3)nc12]<br>3-morpholino-6-((6-((4-(trifluoromethyl)benzyl)amino)pyridin-3-yl)amino)quinoxaline-5-carbonitrile |
| 143 | 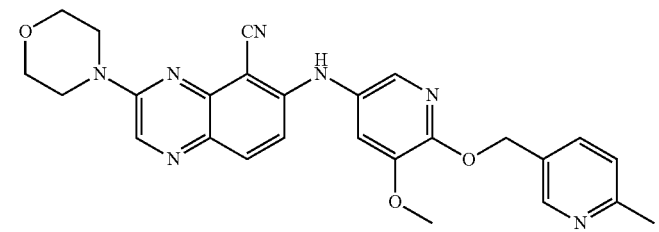 [SMILES: COc1cc(Nc2ccc3ncc(N4CCOCC4)nc3c2C#N)cnc1OCc1ccc(C)nc1]<br>6-((5-methoxy-6-((6-methylpyridin-3-yl)methoxy)pyridin-3-yl)amino)-3-morpholinoquinoxaline-5-carbonitrile |
| 144 | 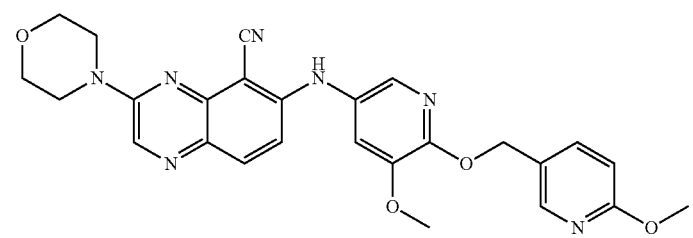 [SMILES: COc1ccc(COc2ncc(Nc3ccc4ncc(N5CCOCC5)nc4c3C#N)cc2OC)cn1]<br>6-((5-methoxy-6-((6-methoxypyridin-3-yl)methoxy)pyridin-3-yl)amino)-3-morpholinoquinoxaline-5-carbonitrile |

TABLE 1-continued

Quinoxaline compounds

| Compound No. | Structure |
|---|---|
| 145 | 3-((2S,6R)-2,6-dimethylmorpholino)-6-((3-methoxy-4-((6-methyl-pyridin-3-yl)methoxy)phenyl)amino)quinoxaline-5-carbonitrile |
| 146 | 6-((3-methoxy-4-((6-methyl-1-($\lambda^1$-oxidaneyl)-1$\lambda^4$-pyridin-3-yl)methoxy)phenyl)amino)-3-morpholinoquinoxaline-5-carbonitrile |

TABLE 2

Calculated mass and observed ESI-MS data

| Compound No. | Calculated Mass | Observed ESI-MS |
|---|---|---|
| 1 | 451.14 | 452.02 |
| 2 | 426.14 | 427.30 |
| 3 | 442.16 | 443.17 |
| 4 | 450.14 | 451.16 |
| 5 | 417.17 | 418.39 |
| 6 | 384.13 | 385.19 |
| 7 | 455.20 | 456.26 |
| 8 | 413.15 | 413.99 |
| 9 | 413.15 | 414.23 |
| 10 | 443.15 | 444.37 |
| 11 | 336.12 | 337.36 |
| 12 | 441.18 | 442.38 |
| 13 | 499.22 | 500.48 |
| 14 | 441.18 | 441.29 |
| 15 | 412.15 | 413.46 |
| 16 | 497.21 | 498.49 |
| 17 | 469.21 | 470.38 |
| 18 | 430.14 | 431.21 |
| 19 | 456.18 | 457.16 |
| 20 | 456.18 | 457.22 |
| 21 | 496.14 | 497.26 |
| 22 | 430.14 | 431.01 |
| 23 | 412.15 | 413.28 |
| 24 | 472.21 | 473.41 |
| 25 | 416.18 | 417.32 |
| 26 | 443.15 | 444.32 |
| 27 | 498.19 | 499.00 |
| 28 | 447.10 | 447.90, 449.78 |
| 29 | 453.22 | 454.52 |
| 30 | 457.16 | 458.11 |
| 31 | 510.24 | 511.55 |
| 32 | 551.18 | 552.49 |
| 33 | 495.23 | 496.38 |
| 34 | 430.14 | 431.09 |
| 35 | 511.22 | 512.40 |
| 36 | 431.20 | 432.24 |
| 37 | 498.20 | 499.61 |
| 38 | 467.20 | 468.35 |
| 39 | 496.22 | 497.32 |
| 40 | 485.19 | 486.05 |
| 41 | 461.21 | 462.42 |
| 42 | 488.25 | 489.50 |
| 43 | 468.19 | 469.26 |
| 44 | 459.23 | 460.32 |
| 45 | 509.21 | 510.46 |
| 46 | 468.19 | 469.24 |
| 47 | 482.21 | 483.44 |
| 48 | 471.20 | 472.55 |
| 49 | 501.16 | 502.49, 503.87 |
| 50 | 498.20 | 499.65 |
| 51 | 469.19 | 470.61 |
| 52 | 468.19 | 469.21 |
| 53 | 485.19 | 486.13 |
| 54 | 482.21 | 483.34 |
| 55 | 471.20 | 472.51 |
| 56 | 485.19 | 486.06 |
| 57 | 468.19 | 469.21 |
| 58 | 527.22 | 528.27 |
| 59 | 497.22 | 498.24 |
| 60 | 511.22 | 512.26 |
| 61 | 472.19 | 473.27 |
| 62 | 481.21 | 482.26 |
| 63 | 501.16 | 502.50 |
| 64 | 492.19 | 493.34 |
| 65 | 492.19 | 493.47 |
| 66 | 540.25 | 541.21 |

TABLE 2-continued

Calculated mass and observed ESI-MS data

| Compound No. | Calculated Mass | Observed ESI-MS |
| --- | --- | --- |
| 67 | 481.22 | 482.06 |
| 68 | 553.23 | 554.43 |
| 69 | 510.24 | 511.37 |
| 70 | 479.17 | 480.39 |
| 71 | 567.25 | 568.30 |
| 72 | 538.23 | 539.37 |
| 73 | 536.18 | 537.13 |
| 74 | 583.25 | 594.74 |
| 75 | 541.24 | 542.19 |
| 76 | 540.25 | 541.17 |
| 77 | 600.28 | 601.47 |
| 78 | 505.22 | 506.08 |
| 79 | 482.21 | 483.24 |
| 80 | 538.27 | 539.37 |
| 81 | 511.19 | 512.16 |
| 82 | 539.26 | 540.29 |
| 83 | 467.20 | 468.17 |
| 84 | 533.25 | 534.26 |
| 85 | 556.26 | 557.60 |
| 86 | 468.19 | 469.10 |
| 87 | 462.18 | 462.18 |
| 88 | 467.20 | 468.22 |
| 89 | 526.25 | 527.43 |
| 90 | 496.22 | 497.16 |
| 91 | 485.19 | 485.91 |
| 92 | 415.16 | 416.24 |
| 93 | 515.20 | 516.33 |
| 94 | 515.20 | 516.31 |
| 95 | 511.23 | 512.13 |
| 96 | 522.20 | 523.37 |
| 97 | 555.26 | 556.60 |
| 98 | 510.24 | 511.29 |
| 99 | 503.18 | 504.60 |
| 100 | 539.26 | 540.28 |
| 101 | 496.22 | 497.06 |
| 102 | 581.28 | 582.43 |
| 103 | 510.24 | 511.27 |
| 104 | 511.23 | 512.15 |
| 105 | 471.20 | 471.61 |
| 106 | 427.19 | 428.12 |
| 107 | 512.22 | 513.09 |
| 108 | 452.18 | 453.24 |
| 109 | 454.20 | 455.13 |
| 110 | 500.20 | 501.21 |
| 111 | 518.19 | 519.29 |
| 112 | 512.22 | 513.03 |
| 113 | 479.20 | 480.16 |
| 114 | 481.21 | 482.16 |
| 115 | 525.25 | 526.50 |
| 116 | 485.22 | 485.95 |
| 117 | 499.23 | 500.36 |
| 118 | 537.25 | 538.38 |
| 119 | 471.19 | 471.69 |
| 120 | 508.22 | 508.86 |
| 121 | 457.18 | 458.45 |
| 122 | 457.18 | 458.46 |
| 123 | 461.21 | 462.45 |
| 124 | 487.17 | 488.70 |
| 125 | 512.22 | 513.20 |
| 126 | 473.15 | 474.45 |
| 127 | 473.15 | 474.45 |
| 128 | 483.20 | 484.30 |
| 129 | 496.22 | 497.27 |
| 130 | 522.24 | 523.30 |
| 131 | 503.21 | 504.50 |
| 132 | 498.20 | 499.33 |
| 133 | 440.20 | 441.30 |
| 134 | 497.22 | 498.34 |
| 135 | 500.22 | 501.37 |
| 136 | 495.24 | 496.41 |
| 137 | 456.19 | 457.35 |
| 138 | 496.22 | 497.30 |
| 139 | 480.19 | 481.12 |
| 140 | 467.16 | 468.01 |
| 141 | 511.23 | 511.23 |
| 142 | 505.18 | 506.15 |
| 143 | 483.20 | 484.10 |
| 144 | 449.20 | 500.30 |
| 145 | 510.24 | 511.10 |
| 146 | 498.20 | 499.30 |

Biological Activity

Various compounds of Formula I were tested for their abilities to inhibit a variety of protein kinases. Brief descriptions of different assays are described below.

1. Biochemical Activity

CSF-1R Kinase Assay

Inhibition of CSF-1R kinase activity by a test compound disclosed herein was estimated by AlphaScreen (PerkinElmer). Standard assay conditions were 1.25 ng of recombinant CSF-1R kinase (SignalChem) with 10 ng Biotin-conjugated Poly-(Glu 4:Tyr 1) (Cisbio) in the assay buffer (10 μM ATP, 10 mM MOPs, pH7.0, 0.21 mM EDTA, 0.5% glycerol, 1 mg/ml BSA, 0.01% 2-mercaptoethanol, 0.001% Brij35) in a final volume of 25 μL. Reactions were incubated at 30° C. for 45 min and stopped by adding 5 μL of 50 mM EDTA. Analysis of resulting product using an AlphaScreen kit, and counted with Enspire Alpha (PerkinElmer). The readout from control reaction (complete reaction mixture) was designated as 0% inhibition and the readout for the reaction without enzyme as 100% inhibition. The $IC_{50}$ values of quinoxaline compounds of this invention against CSF-1R kinase were determined using the GraphPad Prism 5 software.

c-KIT Kinase Assay

Inhibition of c-KIT kinase activity by a test compound disclosed herein was estimated by radiometric assay. Standard assay conditions were 20 ng of recombinant c-Kit (SignalChem) with 2 μg of substrate Poly-(Glu 4:Tyr 1) (sigma) in the assay buffer in kinase reaction buffer (10 mM MOPS pH 7.0, 0.21 mM EDTA, 0.5% glycerol, 0.001% Brij-35, 0.01 2-mercaptoehtanol, 1 mg/ml BSA, 10 mM $MgCl_2$, 10 mM $MnCl_2$, 10 μM ATP, 0.1 μCi per well [$^{33}$P]-ATP, in the presence of test compound (diluted in final concentration of 4% DMSO) or DMSO control, with a final volume of 25 μl for 60 minutes at 30° C. The reaction was stopped by adding 5 μl of 3% phosphoric acid solution. Total reaction solution was then harvested onto a filter plate (UniFilter-96 GF/B, PerkinElmer), and washed 20 times for 5 min with $dH_2O$. 30 μl of MicroScint™-20 Cocktail (PerkinElmer) was added to dried plate. The plate was sealed and counted using a TopCount scintillation detector (PerkinElmer). The readout from control reaction (complete reaction mixture) was designated as 0% inhibition and the readout for the reaction without enzyme as 100% inhibition. The $IC_{50}$ values of quinoxaline compounds of this invention against c-KIT kinase were determined using the GraphPad Prism 5 software.

FLT3 Kinase Assay

Inhibition of FLT3 kinase activity by a test compound disclosed herein was estimated by radiometric assay. Standard assay conditions were 5 ng of recombinant FLT3 (Thermo Fisher) with 2 µg of substrate Poly-(Glu 4:Tyr 1) (sigma) in the assay buffer in kinase reaction buffer (10 mM MOPS pH 7.0, 0.21 mM EDTA, 0.5% glycerol, 0.001% Brij-35, 0.01 2-mercaptoehtanol, 1 mg/ml BSA, $MgCl_2$ 10 mM, 10 µM ATP, 0.1 µCi per well [$^{33}$P]-ATP, in the presence of test compound (diluted in final concentration of 4% DMSO) or DMSO control, with a final volume of 25 µl for 60 minutes at 30° C. The reaction was stopped by adding 5 µl of 3% phosphoric acid solution. Total reaction solution was then harvested onto a filter plate (UniFilter-96 GF/B, PerkinElmer), and washed 20 times for 5 min with $dH_2O$. 30 µl of MicroScint™-20 Cocktail (PerkinElmer) was added to dried plate. The plate was sealed and counted using a TopCount scintillation detector (PerkinElmer). The readout from control reaction (complete reaction mixture) was designated as 0% inhibition and the readout for the reaction without enzyme as 100% inhibition. The $IC_{50}$ values of quinoxaline compounds of this invention against FLT3 kinase were determined using the GraphPad Prism 5 software.

PDGFRβ Kinase Assay

Inhibition of PDGFRβ kinase activity by a test compound disclosed herein was estimated by radiometric assay. Standard assay conditions were 10 ng of recombinant PDGFRβ (SignalChem) with 2 µg of substrate Poly-(Glu 4:Tyr 1) (sigma) in the assay buffer in kinase reaction buffer (10 mM MOPS pH 7.0, 0.21 mM EDTA, 0.5% glycerol, 0.001% Brij-35, 0.01 2-mercaptoehtanol, 1 mg/ml BSA, 10 mM $MgCl_2$, 10 mM $MnCl_2$, 10 µM ATP, 0.1 µCi per well [$^{33}$P]-ATP), in the presence of test compound (diluted in final concentration of 4% DMSO) or DMSO control, with a final volume of 25 µl for 60 minutes at 30° C. The reaction was stopped by adding 5 µl of 3% phosphoric acid solution. Total reaction solution was then harvested onto a filter plate (UniFilter-96 GF/B, PerkinElmer), and washed 20 times for 5 min with $dH_2O$. 30 µl of MicroScint™-20 Cocktail (PerkinElmer) was added to dried plate. The plate was sealed and counted using a TopCount scintillation detector (PerkinElmer). The readout from control reaction (complete reaction mixture) was designated as 0% inhibition and the readout for the reaction without enzyme as 100% inhibition. The $IC_{50}$ values of quinoxaline compounds of this invention against PDGFRβ kinase were determined using the GraphPad Prism 5 software.

The $IC_{50}$ values for selected quinoxaline compounds of this invention against CSF-1R, c-KIT, FLT3, and PDGFRβ are summarized in Table 3. In the table, the symbol "+++" means $IC_{50}$ less than 100 nM, the symbol "++" means $IC_{50}$ is between 100 to 300 nM, and the symbol "+" means $IC_{50}$ is between 300 to 1000 nM.

TABLE 3

| | $IC_{50}$ value for class III RTKs | | | |
|---|---|---|---|---|
| Example No. | CSF-1R $IC_{50}$ | c-KIT $IC_{50}$ | FLT3 $IC_{50}$ | PDGFRβ $IC_{50}$ |
| 3 | + | ++ | >1 µM | >1 µM |
| 4 | >1 µM | + | >1 µM | >1 µM |
| 5 | ++ | >1 µM | >1 µM | >1 µM |
| 7 | +++ | ++ | >1 µM | >1 µM |
| 10 | +++ | >1 µM | >1 µM | >1 µM |
| 12 | +++ | +++ | >1 µM | >1 µM |
| 13 | ++ | + | >1 µM | >1 µM |
| 16 | +++ | +++ | >1 µM | >1 µM |
| 17 | +++ | +++ | >1 µM | >1 µM |
| 19 | +++ | +++ | >1 µM | >1 µM |
| 20 | + | +++ | >1 µM | >1 µM |
| 24 | +++ | +++ | >1 µM | >1 µM |
| 25 | +++ | +++ | >1 µM | >1 µM |
| 26 | +++ | >1 µM | >1 µM | >1 µM |
| 27 | +++ | ++ | >1 µM | >1 µM |
| 28 | +++ | >1 µM | >1 µM | >1 µM |
| 30 | ++ | >1 µM | >1 µM | >1 µM |
| 31 | +++ | +++ | >1 µM | + |
| 32 | +++ | +++ | >1 µM | ++ |
| 33 | +++ | +++ | >1 µM | ++ |
| 35 | +++ | +++ | >1 µM | + |
| 36 | + | ++ | >1 µM | >1 µM |
| 37 | +++ | >1 µM | >1 µM | >1 µM |
| 38 | +++ | +++ | ++ | ++ |
| 39 | >1 µM | ++ | >1 µM | >1 µM |
| 40 | +++ | >1 µM | >1 µM | >1 µM |
| 43 | ++ | +++ | >1 µM | >1 µM |
| 45 | +++ | +++ | >1 µM | >1 µM |
| 46 | + | ++ | >1 µM | >1 µM |
| 48 | >1 µM | + | >1 µM | >1 µM |
| 49 | +++ | +++ | >1 µM | >1 µM |
| 50 | +++ | ++ | >1 µM | >1 µM |
| 51 | >1 µM | +++ | >1 µM | >1 µM |
| 52 | +++ | ++ | + | >1 µM |
| 53 | +++ | + | + | >1 µM |
| 54 | +++ | +++ | >1 µM | >1 µM |
| 55 | >1 µM | + | >1 µM | >1 µM |
| 56 | +++ | ++ | >1 µM | >1 µM |
| 57 | >1 µM | + | >1 µM | >1 µM |
| 58 | +++ | +++ | >1 µM | + |
| 59 | +++ | ++ | >1 µM | >1 µM |
| 60 | +++ | + | >1 µM | >1 µM |
| 61 | +++ | +++ | >1 µM | >1 µM |
| 62 | +++ | +++ | >1 µM | + |
| 63 | +++ | >1 µM | >1 µM | >1 µM |
| 64 | +++ | +++ | >1 µM | >1 µM |
| 65 | +++ | ++ | >1 µM | >1 µM |
| 66 | +++ | +++ | >1 µM | + |
| 67 | +++ | +++ | >1 µM | >1 µM |
| 68 | +++ | +++ | >1 µM | >1 µM |
| 69 | +++ | >1 µM | >1 µM | >1 µM |
| 70 | +++ | >1 µM | >1 µM | >1 µM |
| 71 | +++ | +++ | >1 µM | >1 µM |
| 72 | +++ | +++ | >1 µM | + |
| 73 | +++ | +++ | >1 µM | >1 µM |
| 74 | +++ | +++ | >1 µM | >1 µM |
| 75 | +++ | ++ | >1 µM | >1 µM |
| 76 | +++ | + | >1 µM | >1 µM |
| 77 | +++ | + | >1 µM | >1 µM |
| 78 | +++ | ++ | >1 µM | >1 µM |
| 79 | +++ | +++ | >1 µM | >1 µM |
| 80 | +++ | +++ | >1 µM | >1 µM |
| 81 | +++ | + | >1 µM | >1 µM |
| 82 | +++ | ++ | >1 µM | >1 µM |
| 83 | +++ | +++ | >1 µM | >1 µM |
| 84 | +++ | +++ | >1 µM | >1 µM |
| 85 | +++ | +++ | >1 µM | >1 µM |
| 86 | +++ | ++ | >1 µM | >1 µM |
| 87 | +++ | ++ | >1 µM | >1 µM |
| 88 | +++ | +++ | >1 µM | >1 µM |
| 89 | +++ | +++ | >1 µM | >1 µM |
| 90 | +++ | +++ | >1 µM | >1 µM |
| 91 | +++ | ++ | >1 µM | >1 µM |
| 92 | + | ++ | >1 µM | >1 µM |
| 93 | +++ | +++ | >1 µM | >1 µM |
| 94 | +++ | +++ | >1 µM | >1 µM |
| 95 | +++ | ++ | >1 µM | >1 µM |
| 96 | +++ | ++ | >1 µM | >1 µM |
| 97 | +++ | ++ | >1 µM | >1 µM |
| 98 | +++ | +++ | >1 µM | >1 µM |
| 99 | +++ | >1 µM | >1 µM | >1 µM |
| 100 | +++ | ++ | >1 µM | >1 µM |
| 101 | +++ | +++ | >1 µM | >1 µM |
| 102 | +++ | ++ | >1 µM | >1 µM |

TABLE 3-continued

$IC_{50}$ value for class III RTKs

| Example No. | CSF-1R $IC_{50}$ | c-KIT $IC_{50}$ | FLT3 $IC_{50}$ | PDGFRβ $IC_{50}$ |
|---|---|---|---|---|
| 103 | +++ | +++ | >1 μM | >1 μM |
| 104 | +++ | +++ | >1 μM | >1 μM |
| 105 | +++ | +++ | >1 μM | >1 μM |
| 106 | +++ | + | >1 μM | >1 μM |
| 107 | +++ | ++ | >1 μM | >1 μM |
| 108 | +++ | >1 μM | >1 μM | >1 μM |
| 109 | +++ | >1 μM | >1 μM | >1 μM |
| 110 | +++ | ++ | >1 μM | >1 μM |
| 111 | +++ | ++ | >1 μM | >1 μM |
| 112 | +++ | +++ | >1 μM | >1 μM |
| 113 | +++ | +++ | >1 μM | >1 μM |
| 114 | +++ | + | >1 μM | >1 μM |
| 115 | +++ | + | >1 μM | >1 μM |
| 116 | +++ | ++ | >1 μM | >1 μM |
| 117 | +++ | + | >1 μM | >1 μM |
| 118 | +++ | ++ | >1 μM | >1 μM |
| 119 | ++ | >1 μM | ++ | >1 μM |
| 120 | +++ | +++ | >1 μM | >1 μM |
| 121 | ++ | ++ | >1 μM | >1 μM |
| 122 | ++ | +++ | >1 μM | >1 μM |
| 123 | >1 μM | + | >1 μM | >1 μM |
| 124 | +++ | +++ | >1 μM | >1 μM |
| 125 | +++ | +++ | >1 μM | >1 μM |
| 126 | +++ | +++ | >1 μM | >1 μM |
| 127 | +++ | +++ | >1 μM | >1 μM |
| 128 | ++ | + | >1 μM | >1 μM |
| 129 | +++ | + | >1 μM | >1 μM |
| 130 | +++ | +++ | >1 μM | >1 μM |
| 131 | +++ | + | >1 μM | >1 μM |
| 132 | +++ | + | >1 μM | >1 μM |
| 133 | +++ | +++ | >1 μM | >1 μM |
| 134 | +++ | +++ | >1 μM | >1 μM |
| 135 | +++ | +++ | >1 μM | >1 μM |
| 136 | +++ | +++ | >1 μM | >1 μM |
| 137 | +++ | +++ | >1 μM | >1 μM |
| 138 | +++ | +++ | >1 μM | >1 μM |
| 139 | +++ | ++ | >1 μM | >1 μM |
| 140 | ++ | >1 μM | >1 μM | >1 μM |
| 141 | +++ | +++ | >1 μM | + |
| 143 | +++ | + | >1 μM | >1 μM |
| 144 | +++ | >1 μM | >1 μM | >1 μM |
| 145 | +++ | ++ | >1 μM | >1 μM |
| 146 | ++ | ++ | ++ | >1 μM |

2. Anti-Proliferation Activity

As noted above, compounds of the invention may be used to treat protein kinase-related diseases or disorders. The protein kinase-related disease may be cancer, an autoimmune disease, or a blood vessel proliferative disorder. The cancer may be lung cancer, colon cancer, colorectal cancer, breast cancer, prostate cancer, liver cancer, pancreatic cancer, bladder cancer, gastric cancer, renal cancer, salivary gland cancer, ovarian cancer, uterine body cancer, cervical cancer, oral cancer, skin cancer, brain cancer, lymphoma, or leukemia.

Inhibition of cell growth by compounds was measured using CellTiter™-96 assay. The cytotoxicity of compounds was evaluated in CSF-1-dependent M-NFS-60 mouse myeloid leukemia cell, FLT3 signal addicted MV4-11 human acute myeloid leukemia cell with FLT3-ITD mutation, c-KIT signal addicted Kasumi-1 human acute myeloid leukemia cell with c-KIT N822K activating mutation, and THP-1 human acute monocytic leukemia cell harboring NRAS G12D mutation.

M-NFS-60 Cell Culture

The compounds disclosed herein were tested in M-NFS-60 cell proliferation assay to determine their cellular potency against CSF-1R. The proliferation and viability of M-NFS-60 cells, a murine myeloblastic cell line, depend on the binding of the ligand M-CSF to its receptor, CSF-1R, to proliferate. Inhibition of CSF-1R kinase activity will cause reduced growth and/or cell death. M-NFS-60 cells (catalog # CRL-1838) were obtained from the American Type Culture Collection (ATCC, Manassas, Va.). Briefly, cells were grown in suspension in RPMI 1640 medium supplemented with 10% characterized fetal bovine serum (Invitrogen, Carlsbad, Calif.), 0.05 mM 2-mercaptoethanol, and 20 ng/mL mouse recombinant macrophage colony stimulating factor (M-CSF) at 37° C., 5% $CO_2$, and 95% humidity. Cells were allowed to expand until reaching saturation at which point they were subcultured or harvested for assay use.

MV4-11 Cell Culture

The compounds disclosed herein were tested in MV4-11 cell proliferation assay to determine their cellular potency against FLT3 kinase. MV4-11 human acute myeloid leukemia cells harbor ligand-independent FLT3-ITD activating mutation, which render its proliferation FLT3-ITD dependent. Inhibition of FLT3 kinase activity will cause reduced growth and/or cell death. MV4-11 cells (catalog # CRL-9591) were obtained from the American Type Culture Collection (ATCC, Manassas, Va.). Briefly, cells were grown in suspension in IMDM medium supplemented with 10% characterized heat inactive fetal bovine serum (Invitrogen, Carlsbad, Calif.), at 37° C., 5% $CO_2$, and 95% humidity. Cells were allowed to expand until reaching saturation at which point they were subcultured or harvested for assay use.

Kasumi-1 Cell Culture

The compounds disclosed herein were tested in Kasumi cell proliferation assay to determine their cellular potency against c-KIT kinase. Kasumi human acute myeloid leukemia cells harbor ligand-independent N822K c-KIT activating mutation, thus the cell proliferation relied on c-KIT signal. Inhibition of c-KIT kinase activity will cause reduced growth and/or cell death. Kasumi-1 cells (catalog # CRL-2724) were obtained from the American Type Culture Collection (ATCC, Manassas, Va.). Briefly, cells were grown in suspension in RPMI 1640 medium supplemented with 10% characterized fetal bovine serum (Invitrogen, Carlsbad, Calif.) at 37° C., 5% $CO_2$, and 95% humidity. Cells were allowed to expand until reaching saturation at which point they were subcultured or harvested for assay use.

THP-1 Cell Culture

The compounds disclosed herein were tested in THP-1 cell proliferation assay as counter screen to demonstrate their selectively anti-proliferative activity for cell growth relied on each class III RTKs signaling. THP-1 human acute monocytic leukemia cells harbor NRAS G12D mutation, which renders cell proliferate independently of class III RTKs signal. THP-1 cells (catalog # TIB-202) were obtained from the ATCC. Briefly, cells were grown in RPMI 1640 supplemented with 10% characterized fetal bovine serum, and 0.05 mM 2-mercaptoethanol at 37° C., 5% $CO_2$, 95% humidity. Cells were allowed to expand until reaching saturation at which point they were subcultured or harvested for assay use.

M-NFS-60, Kasumi-1, MV4-11 and THP-1 cells were seeded into 96-well plates at 2000, 64000, 6500, and 5000 cells/well, respectively, and incubated at 37° C., 5% CO$_2$ overnight. Then, these seeded cells were treated with increasing concentrations of the test compounds and incubated for another 72 hours. At the end of the incubation, CellTiter96® AQueous One Solution Reagent (Promega) was added and incubated for 4 hours. Cell viability was determined by measuring absorbance at 490 nm using EMax® microplate reader (Molecular Devices).

The 50% inhibitory concentration (IC$_{50}$) value was calculated by plotting the percentage of growth inhibition against the concentration of compound, using GraphPad Prism 5 software for curve fitting. The anti-proliferative activities of the selected quinoxaline compounds of this invention are listed in Table 4. In the table, the symbol "+++" represents that IC$_{50}$ less than 0.3 μM, "++" represents that IC$_{50}$ is between 0.3 to 1 μM, and "+" represents that IC$_{50}$ is between 1 to 10 μM.

TABLE 4

| | Cytotoxicity | | | |
|---|---|---|---|---|
| Example No. | M-NFS-60 IC$_{50}$ | Kasumi-1 IC$_{50}$ | MV4-11 IC$_{50}$ | THP-1 IC$_{50}$ |
| 1 | >10 μM | + | + | >10 μM |
| 4 | >10 μM | + | + | >10 μM |
| 5 | + | + | + | >10 μM |
| 6 | >10 μM | >10 μM | + | >10 μM |
| 7 | +++ | +++ | >10 μM | >10 μM |
| 8 | >10 μM | >10 μM | + | >10 μM |
| 10 | +++ | >10 | + | >10 μM |
| 11 | >10 | + | + | >10 μM |
| 12 | +++ | ++ | >10 μM | >10 μM |
| 13 | + | + | + | + |
| 14 | >10 μM | >10 μM | + | >10 μM |
| 16 | +++ | +++ | >10 μM | >10 μM |
| 17 | +++ | ++ | + | >10 μM |
| 19 | +++ | ++ | >10 μM | >10 μM |
| 20 | >10 μM | + | >10 μM | >10 μM |
| 24 | +++ | +++ | + | >10 μM |
| 25 | +++ | ++ | + | + |
| 26 | +++ | + | >10 μM | >10 μM |
| 27 | +++ | +++ | >10 μM | >10 μM |
| 28 | ++ | + | + | >10 μM |
| 30 | +++ | >10 μM | >10 μM | >10 μM |
| 31 | +++ | +++ | + | >10 μM |
| 32 | +++ | ++ | + | >10 μM |
| 33 | +++ | +++ | + | >10 μM |
| 35 | +++ | +++ | + | >10 μM |
| 36 | >10 μM | ++ | + | >10 μM |
| 37 | +++ | >10 μM | >10 μM | >10 μM |
| 38 | +++ | ++ | +++ | >10 μM |
| 39 | >10 μM | ++ | + | >10 μM |
| 40 | +++ | >10 μM | >10 μM | >10 μM |
| 41 | >10 μM | + | + | >10 μM |
| 42 | + | + | + | >10 μM |
| 43 | ++ | ++ | + | >10 μM |
| 44 | + | + | + | >10 μM |
| 45 | +++ | ++ | >10 μM | >10 μM |
| 46 | + | + | + | >10 μM |
| 47 | + | >10 μM | + | >10 μM |
| 48 | >10 μM | + | >10 μM | >10 μM |
| 49 | +++ | ++ | + | >10 μM |
| 50 | +++ | ++ | >10 μM | >10 μM |
| 51 | >10 μM | ++ | >10 μM | >10 μM |
| 52 | ++ | ++ | +++ | >10 μM |
| 53 | ++ | + | +++ | >10 μM |
| 54 | +++ | ++ | + | >10 μM |
| 56 | ++ | + | ++ | >10 μM |
| 58 | +++ | +++ | >10 μM | >10 μM |
| 59 | +++ | ++ | + | + |
| 60 | +++ | + | + | >10 μM |
| 61 | >10 μM | ++ | >10 μM | >10 μM |
| 62 | +++ | +++ | >10 μM | >10 μM |
| 63 | + | >10 μM | >10 μM | >10 μM |
| 64 | +++ | ++ | + | >10 μM |
| 65 | +++ | >10 μM | >10 μM | >10 μM |
| 66 | +++ | +++ | + | >10 μM |
| 67 | +++ | + | + | + |
| 68 | +++ | +++ | + | >10 μM |
| 69 | ++ | >10 μM | >10 μM | >10 μM |
| 71 | +++ | +++ | >10 μM | >10 μM |
| 72 | +++ | +++ | >10 μM | >10 μM |
| 73 | +++ | +++ | >10 μM | >10 μM |
| 74 | +++ | ++ | + | >10 μM |
| 75 | +++ | ++ | >10 μM | >10 μM |
| 76 | +++ | + | + | >10 μM |
| 77 | ++ | + | + | + |
| 78 | +++ | ++ | >10 μM | >10 μM |
| 79 | +++ | ++ | + | >10 μM |
| 80 | +++ | +++ | + | + |
| 81 | +++ | >10 μM | >10 μM | >10 μM |
| 82 | +++ | +++ | + | + |
| 83 | +++ | +++ | >10 μM | >10 μM |
| 84 | +++ | ++ | + | + |
| 85 | +++ | +++ | + | + |
| 86 | +++ | + | >10 μM | >10 μM |
| 87 | ++ | + | >10 μM | >10 μM |
| 88 | +++ | ++ | + | >10 μM |
| 89 | +++ | + | + | + |
| 90 | +++ | ++ | >10 μM | >10 μM |
| 91 | ++ | + | + | >10 μM |
| 92 | + | ++ | + | >10 μM |
| 93 | +++ | +++ | >10 μM | >10 μM |
| 94 | +++ | ++ | >10 μM | >10 μM |
| 95 | +++ | ++ | + | + |
| 96 | +++ | >10 μM | + | >10 μM |
| 97 | +++ | ++ | + | >10 μM |
| 98 | +++ | +++ | + | >10 μM |
| 99 | +++ | >10 μM | >10 μM | >10 μM |
| 100 | +++ | ++ | + | >10 μM |
| 101 | +++ | +++ | + | >10 μM |
| 102 | +++ | +++ | >10 μM | >10 μM |
| 103 | +++ | +++ | + | >10 μM |
| 104 | + | + | + | >10 μM |
| 105 | +++ | ++ | + | >10 μM |
| 106 | ++ | + | >10 μM | >10 μM |
| 107 | +++ | ++ | + | >10 μM |
| 108 | + | >10 μM | >10 μM | >10 μM |
| 109 | + | + | >10 μM | >10 μM |
| 110 | +++ | + | + | >10 μM |
| 111 | +++ | ++ | + | >10 μM |
| 112 | +++ | +++ | + | >10 μM |
| 113 | +++ | ++ | + | >10 μM |
| 114 | + | + | + | >10 μM |
| 115 | +++ | + | + | >10 μM |
| 116 | +++ | ++ | + | >10 μM |
| 117 | +++ | + | + | >10 μM |
| 118 | +++ | + | >10 μM | >10 μM |
| 119 | + | >10 μM | + | >10 μM |
| 120 | +++ | +++ | >10 μM | >10 μM |
| 121 | + | ++ | + | >10 μM |
| 122 | + | ++ | + | >10 μM |
| 123 | >10 μM | + | + | >10 μM |
| 124 | +++ | ++ | + | + |
| 125 | + | +++ | >10 μM | >10 μM |
| 126 | ++ | +++ | + | >10 μM |
| 127 | + | ++ | + | >10 μM |
| 128 | ++ | + | + | >10 μM |
| 129 | ++ | + | + | >10 μM |
| 130 | +++ | ++ | + | >10 μM |
| 131 | +++ | >10 μM | >10 μM | >10 μM |
| 132 | ++ | >10 μM | >10 μM | >10 μM |
| 133 | +++ | ++ | >10 μM | >10 μM |
| 134 | +++ | ++ | + | >10 μM |
| 135 | +++ | +++ | + | >10 μM |
| 136 | ++ | + | + | >10 μM |
| 137 | +++ | ++ | + | >10 μM |
| 138 | +++ | +++ | + | >10 μM |
| 139 | +++ | >10 μM | >10 μM | >10 μM |
| 141 | +++ | +++ | + | >10 μM |

TABLE 4-continued

| | Cytotoxicity | | | |
|---|---|---|---|---|
| Example No. | M-NFS-60 $IC_{50}$ | Kasumi-1 $IC_{50}$ | MV4-11 $IC_{50}$ | THP-1 $IC_{50}$ |
| 143 | +++ | >10 μM | + | >10 μM |
| 144 | +++ | >10 μM | >10 μM | >10 μM |
| 145 | +++ | ++ | + | >10 μM |
| 146 | + | + | + | >10 μM |

3. Osteoclast Tartrate-Resistant Acid Phosphatase Assay

A serial dilution of test compound was dispensed into a 96-well black clear bottom plate. Compound was diluted by the addition of DMEM media supplemented with 10% characterized fetal bovine serum. Diluted compound was transferred to a 96-well black clear bottom plate. Three thousand osteoclast precursors (Lonza, Walkersville, Md.) were added per well in growth medium containing Receptor Activator of Nuclear Factor Kappa-beta ligand (RANKL) and M-CSF. Plates were incubated for 7 days at 37° C., 5% $CO_2$, and 95% humidity to allow differentiation of osteoclast precursors. At the end of the incubation period, 50 μL of supernatant from each well was transferred to a clear 96-well plate. Tartrate-resistant acid phosphatase activity in the supernatant samples was determined using an acid phosphatase assay kit (Sigma, St. Louis, Mo.). Absorbance was measured at 550 nm using a plate reader. The readout from control reaction (cells cultured in complete growth medium mixture) was designated as 0% inhibition and the readout for the cells cultured in medium without RANKL as 100% inhibition. The Inhibition activity against osteoclast differentiation for each compound at 1 μM treatment in duplicate was measured.

The compounds of formula I exhibited more than 50% inhibition activity against osteoclast differentiation at 1 μM treatment are listed in following Table 5.

TABLE 5

| Inhibition of osteoclast differentiation | |
|---|---|
| Compound with >50% inhibition activity against osteoclast differentiation (at 1 μM treatment) | Example 7, 10, 12, 16, 17, 19, 24, 25, 26, 27, 28, 31, 32, 33, 35, 37, 38, 40, 45, 49, 50, 52, 53, 54, 56, 58, 59, 60, 62, 64, 65, 66, 67, 68, 69, 71, 72, 73, 74, 75, 76, 77, 78, 79, 80, 81, 82, 83, 84, 85, 86, 87, 88, 89, 90, 91, 93, 94, 95, 96, 97, 98, 99, 100, 101, 102, 103, 105, 106, 107, 108, 109, 110, 111, 112, 113, 114, 115, 116, 117, 118, 120, 124, 125, 126, 127, 129, 130, 131, 132, 133, 134, 135, 136, 137, 138, 139, 141, 143, 144, 145 |

Some embodiments of the invention relate to methods for treating a protein kinase-related disease, such as a disease or disorder mediated by CSF-1R, FLT3, c-KIT, and/or PDGFR kinase, or mediated by a mutant kinase of CSF-1R, FLT3, c-KIT, or PDGFR. A method in accordance with one embodiment of the invention comprises administering to a subject in need thereof an effective amount of a compound of the invention.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A compound of formula (I):

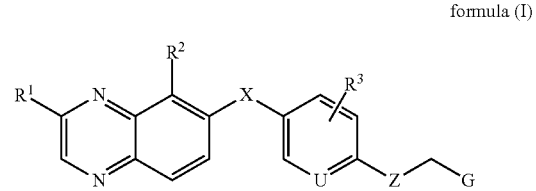

formula (I)

or a stereoisomer, a tautomer, a pharmaceutically acceptable salt thereof, wherein:

X is selected from the group consisting of $CR^4R^5$, $NR^6$, O and S;

Z is selected from the group consisting of —$NR^7$— and —O—;

U is N or $CR^8$;

G is selected from the group consisting of aryl, heteroaryl, cycloalkyl, heterocycle and alkyne;

$R^1$ is selected from the group consisting of hydrogen, deuterium, halogen, amino, hydroxyl, $C_1$-$C_6$ alkyl, $C_2$-$C_6$ alkenyl, $C_2$-$C_6$ alkynyl, $C_3$-$C_6$ cycloalkyl, $C_5$-$C_6$ cycloalkenyl, $C_1$-$C_6$ alkylamino, $C_1$-$C_6$ dialkylamino, $C_3$-$C_6$ cycloalkylamino, $C_1$-$C_6$ alkoxy, $C_3$-$C_6$ cycloalkoxy, aryl, a 3-to-6 membered heterocyclyl, and a 5-to-6 membered heteroaryl, wherein the alkylamino, dialkylamino, alkoxy, alkyl, alkenyl, alkynyl, cycloalkyl, cycloalkenyl, cycloalkylamino, cycloalkoxy, heterocyclyl, aryl and heteroaryl are optionally substituted with halogen, amino, hydroxyl, cyano, nitro, acyl, acyloxy, $C_1$-$C_4$ alkyl, hydroxyl $C_1$-$C_4$ alkyl, alkoxy $C_1$-$C_4$ alkyl, acyloxy $C_1$-$C_4$ alkyl, $C_1$-$C_4$ alkoxy, $C_1$-$C_4$ dialkylamino, $C_3$-$C_6$ cycloalkyl, a 3-to-6 membered heterocyclyl, aryl, and a 5-to-6 membered heteroaryl;

$R^2$ is selected from the group consisting of hydrogen, deuterium, halogen, nitro, cyano, trifluoromethyl, $C_1$-$C_6$ alkylamino, $C_1$-$C_6$ dialkylamino, $C_1$-$C_6$ alkoxy, carboxylic acid, $C_1$-$C_6$ alkyl carbonyl, $C_2$-$C_6$ alkenyl carbonyl, $C_1$-$C_6$ alkoxy carbonyl, amino carbonyl, $C_1$-$C_6$ alkylamino carbonyl and $C_1$-$C_6$ dialkylamino carbonyl;

$R^3$ is selected from the group consisting of hydrogen, deuterium, halogen, hydroxyl, amino, cyano, trifluoromethyl, $C_1$-$C_6$ alkyl, $C_1$-$C_6$ alkoxy, $C_1$-$C_6$ alkylamino and $C_1$-$C_6$ dialkylamino;

$R^4$ is selected from the group consisting of hydrogen, deuterium, halogen, hydroxyl, amino, $C_1$-$C_6$ alkyl, $C_1$-$C_6$ haloalkyl, $C_1$-$C_6$ alkoxy and aryl;

$R^5$ is selected from the group consisting of hydrogen, deuterium, $C_1$-$C_6$ alkyl and $C_1$-$C_6$ haloalkyl;

$R^6$ is selected from the group consisting of hydrogen, $C_1$-$C_6$ alkyl and $C_1$-$C_6$ haloalkyl;

$R^7$ is selected from the group consisting of hydrogen, $C_1$-$C_6$ alkyl and $C_1$-$C_6$ haloalkyl; and $R^8$ is selected from the group consisting of hydrogen, deuterium, halogen, hydroxyl, amino, cyano, trifluoromethyl, $C_1$-$C_6$ alkyl, $C_1$-$C_6$ alkoxy, $C_1$-$C_6$ alkylamino and $C_1$-$C_6$ dialkylamino.

2. The compound of claim 1, wherein G is selected from:

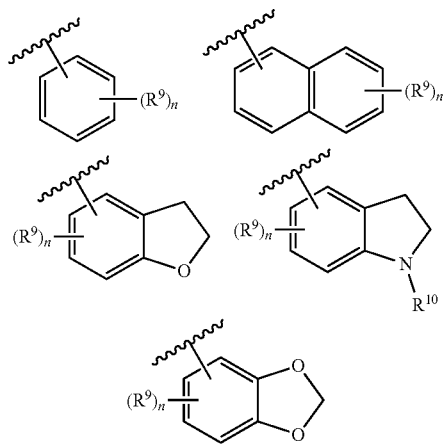

wherein

R⁹ is selected from the group consisting of hydrogen, deuterium, halogen, nitro, cyano, trifluoromethoxy, $C_1$-$C_6$ alkyl, $C_1$-$C_6$ haloalkyl, $C_1$-$C_6$ alkylamino$C_1$-$C_6$ alkyl, $C_1$-$C_6$ dialkylamino$C_1$-$C_6$ alkyl, $C_1$-$C_6$ alkylamino, $C_1$-$C_6$ alkoxy$C_1$-$C_6$ alkyl, $C_1$-$C_6$ dialkylamino, $C_1$-$C_6$ alkoxy, carboxylic acid, carbonyl $C_1$-$C_6$ alkoxy, carbonyl $C_1$-$C_6$ alkylamino, and carbonyl $C_1$-$C_6$ dialkylamino;

R¹⁰ is selected from the group consisting of hydrogen, $C_1$-$C_6$ alkyl and $C_1$-$C_6$ haloalkyl; and each n is individually and independently 0, 1, 2, or 3.

3. The compound of claim 1, wherein G is selected from:

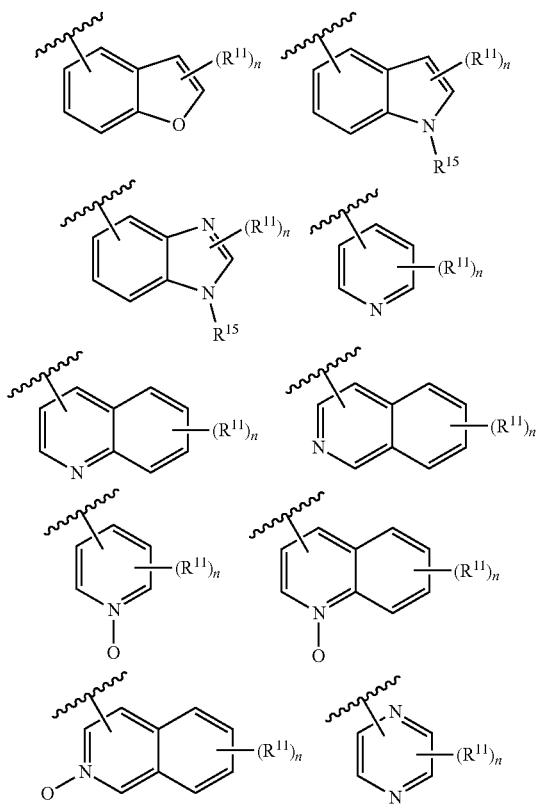

-continued

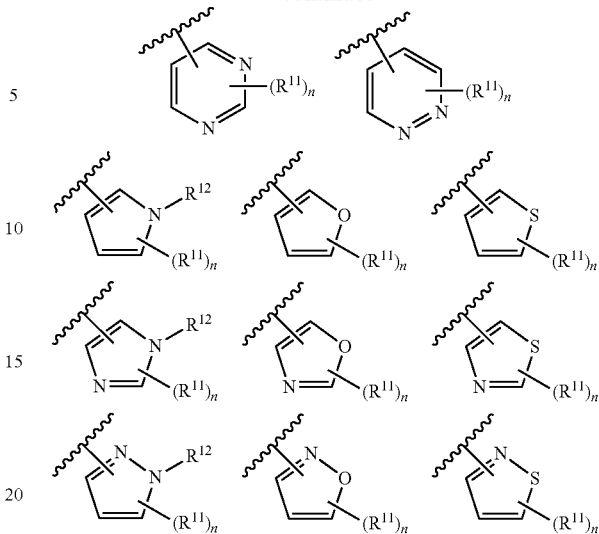

wherein

R¹¹ is selected from the group consisting of hydrogen, deuterium, halogen, nitro, cyano, $C_1$-$C_6$ alkyl, $C_1$-$C_6$ haloalkyl, $C_3$-$C_6$ cycloalkyl, $C_3$-$C_6$ cycloalkyl $C_1$-$C_6$ alkyl, $C_1$-$C_6$ alkylamino, $C_1$-$C_6$ dialkylamino, $C_1$-$C_6$ alkoxy, $C_1$-$C_6$ alkoxy $C_1$-$C_6$ alkyl, carboxylic acid, carbonyl $C_1$-$C_6$ alkoxy, carbonyl $C_1$-$C_6$ alkylamino and carbonyl $C_1$-$C_6$ dialkylamino;

R¹² is selected from the group consisting of hydrogen, $C_1$-$C_6$ alkyl and $C_1$-$C_6$ haloalkyl; and each n is individually and independently 0, 1, 2, or 3.

4. The compound of claim 1, wherein G is selected from:

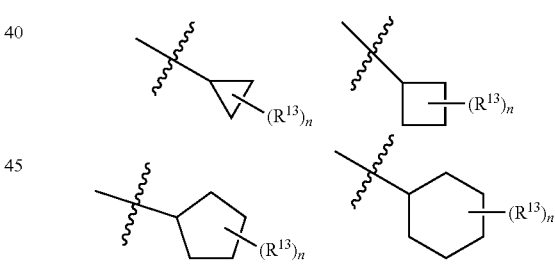

R¹³ is selected from the group consisting of hydrogen, deuterium, halogen, nitro, cyano, $C_1$-$C_6$ alkyl, $C_1$-$C_6$ haloalkyl, $C_1$-$C_6$ alkylamino, $C_1$-$C_6$ dialkylamino, $C_1$-$C_6$ alkoxy, carboxylic acid, $C_1$-$C_6$ alkoxycarbonyl, $C_1$-$C_6$ alkylaminocarbonyl and $C_1$-$C_6$ dialkylaminocarbonyl; and each n is individually and independently 0, 1, 2, or 3.

5. The compound of claim 1, wherein G is selected from:

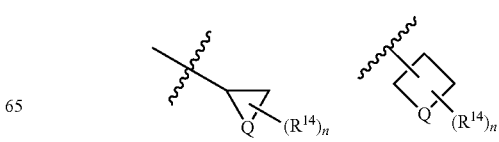

-continued

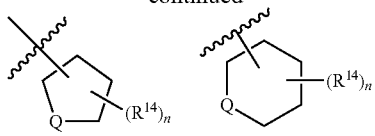

wherein
R¹⁴ is selected from the group consisting of hydrogen, deuterium, halogen, nitro, cyano, $C_1$-$C_6$ alkyl, $C_1$-$C_6$ haloalkyl, $C_1$-$C_6$ alkylamino, $C_1$-$C_6$ dialkylamino, $C_1$-$C_6$ alkoxy, carboxylic acid, $C_1$-$C_6$ alkoxycarbonyl, $C_1$-$C_6$ alkylaminocarbonyl and $C_1$-$C_6$ dialkylaminocarbonyl;
Q is selected from $NR^{15}$, O, and S, wherein $R^{15}$ is selected from the group consisting of hydrogen, $C_1$-$C_6$ alkyl and $C_1$-$C_6$ haloalkyl; and
each n is individually and independently 0, 1, 2, or 3.

6. The compound of claim 1, wherein G is:

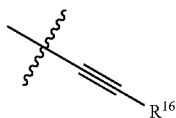

wherein $R^{16}$ is selected from the group consisting of hydrogen, deuterium, $C_1$-$C_6$ alkyl, $C_1$-$C_6$ haloalkyl, 3-to-6 membered heterocyclyl, 5-to-6 membered heteroaryl, $C_1$-$C_6$ alkoxycarbonyl, $C_1$-$C_6$ alkylaminocarbonyl and $C_1$-$C_6$ dialkylaminocarbonyl.

7. The compound of claim 1, wherein X is NH.
8. The compound of claim 1, wherein Z is —O—.
9. The compound of claim 1, where the compound is:
3-methoxy-6-((6-(((6-(trifluoromethyl)pyridin-3-yl)methyl)amino)pyridin-3-yl)amino)quinoxaline-5-carbonitrile;
$N^5$-(3-methoxyquinoxalin-6-yl)-$N^2$-((6-(trifluoromethyl)pyridin-3-yl)methyl)pyridine-2,5-diamine;
3-methoxy-6-((3-methoxy-4-((4-methoxybenzyl)oxy)phenyl)amino)quinoxaline-5-carbonitrile;
3-methoxy-6-((6-((4-(trifluoromethyl)benzyl)amino)pyridin-3-yl)amino)quinoxaline-5-carbonitrile;
3-methoxy-N-(3-methoxy-4-((4-methoxybenzyl)oxy)phenyl)quinoxalin-6-amine;
3-methoxy-6-((6-(pyridin-3-ylmethoxy)pyridin-3-yl)amino)quinoxaline-5-carbonitrile;
3-(dimethylamino)-6-((3-methoxy-4-((4-methoxybenzyl)oxy)phenyl)amino)quinoxaline-5-carbonitrile;
3-methoxy-6-((3-methoxy-4-(pyridin-3-ylmethoxy)phenyl)amino)quinoxaline-5-carbonitrile;
3-methoxy-6-((6-((4-methoxybenzyl)oxy)pyridin-3-yl)amino)quinoxaline-5-carbonitrile;
3-methoxy-6-(3-methoxy-4-((4-methoxybenzyl)oxy)phenoxy)quinoxaline-5-carbonitrile;
6-(3-methoxy-4-(4-methoxybenzyloxy)phenylamino)-3-(methylamino)quinoxaline-5-carbonitrile;
3-(2-(dimethylamino)ethoxy)-6-(3-methoxy-4-(4-methoxybenzyloxy)phenylamino)-quinoxaline-5-carbonitrile;
3-methoxy-6-(3-methoxy-4-(4-methoxybenzylamino)phenylamino)quinoxaline-5-carbonitrile;
3-methoxy-6-(4-(4-methoxybenzyloxy)phenylamino)quinoxaline-5-carbonitrile;
6-(3-methoxy-4-(4-methoxybenzyloxy)phenylamino)-3-morpholinoquinoxaline-5-carbonitrile;
3-(isopropylamino)-6-(3-methoxy-4-(4-methoxybenzyloxy)phenylamino)quinoxaline-5-carbonitrile;
6-(2-fluoro-4-(4-methoxybenzyloxy)phenylamino)-3-methoxyquinoxaline-5-carbonitrile;
3-(dimethylamino)-6-(3-methoxy-4-(4-methoxybenzyloxy)phenoxy)quinoxaline-5-carbonitrile;
6-(4-(4-ethoxybenzyloxy)-3-methoxyphenylamino)-3-methoxyquinoxaline-5-carbonitrile;
3-methoxy-6-(3-methoxy-4-(4-(trifluoromethoxy)benzyloxy)phenylamino)quinoxaline-5-carbonitrile;
6-(3-fluoro-4-(4-methoxybenzyloxy)phenylamino)-3-methoxyquinoxaline-5-carbonitrile;
6-(4-(benzyloxy)-3-methoxyphenylamino)-3-methoxyquinoxaline-5-carbonitrile;
N-(3-methoxy-4-(4-methoxybenzyloxy)phenyl)-3-morpholinoquinoxalin-6-amine;
$N^7$-(3-methoxy-4-(4-methoxybenzyloxy)phenyl)-$N^2$-methylquinoxaline-2,7-diamine;
3-methoxy-6-(3-methoxy-4-(4-methoxybenzyloxy)phenoxy)quinoxaline-5-carbonitrile;
6-(3-methoxy-4-(4-methoxybenzyloxy)phenoxy)-3-morpholinoquinoxaline-5-carbonitrile;
6-(4-(4-chlorobenzyloxy)-3-methoxyphenoxy)-3-methoxyquinoxaline-5-carbonitrile;
6-(4-(4-isopropylbenzylamino)-3-methoxyphenylamino)-3-methoxyquinoxaline-5-carbonitrile;
6-(3-ethoxy-4-(4-methoxybenzyloxy)phenoxy)-3-methoxyquinoxaline-5-carbonitrile;
6-(3-methoxy-4-(4-methoxybenzyloxy)phenylamino)-3-(4-methylpiperazin-1-yl) quinoxaline-5-carbonitrile;
6-(3-methoxy-4-(4-(trifluoromethoxy)benzyloxy)phenylamino)-3-morpholinoquinoxaline-5-carbonitrile;
6-(4-(4-ethylbenzyloxy)-3-methoxyphenylamino)-3-morpholinoquinoxaline-5-carbonitrile;
6-(4-(4-fluorobenzyloxy)-3-methoxyphenylamino)-3-methoxyquinoxaline-5-carbonitrile;
6-(4-(4-ethoxybenzyloxy)-3-methoxyphenylamino)-3-morpholinoquinoxaline-5-carbonitrile;
6-(4-(cyclopropylmethoxy)-3-methoxyphenylamino)-3-morpholinoquinoxaline-5-carbonitrile;
6-(5-methoxy-6-(4-methoxybenzyloxy)pyridin-3-ylamino)-3-morpholinoquinoxaline-5-carbonitrile;
6-(4-(4-methoxybenzyloxy)phenylamino)-3-morpholinoquinoxaline-5-carbonitrile;
6-(3-methoxy-4-(4-methoxybenzylamino)phenylamino)-3-morpholinoquinoxaline-5-carbonitrile;
6-(4-(4-fluorobenzyloxy)-3-methoxyphenylamino)-3-morpholinoquinoxaline-5-carbonitrile;
6-(3-methoxy-4-((3-methyl oxetan-3-yl)methoxy)phenylamino)-3-morpholinoquinoxaline-5-carbonitrile;
6-(3-methoxy-4-((1-methylpiperidin-4-yl)methoxy)phenylamino)-3-morpholino-quinoxaline-5-carbonitrile;
6-(3-methoxy-4-(pyridin-3-ylmethoxy)phenylamino)-3-morpholinoquinoxaline-5-carbonitrile;
6-(4-(cyclopentylmethoxy)-3-methoxyphenylamino)-3-morpholinoquinoxaline-5-carbonitrile;
6-(4-((2,3-dihydrobenzofuran-5-yl)methoxy)-3-methoxyphenylamino)-3-morpholino-quinoxaline-5-carbonitrile;
6-(3-methoxy-4-(pyridin-4-ylmethoxy)phenylamino)-3-morpholinoquinoxaline-5-carbonitrile;
6-(3-ethoxy-4-(pyridin-4-ylmethoxy)phenylamino)-3-morpholinoquinoxaline-5-carbonitrile;

6-(3-methoxy-4-(1-methyl-1H-imidazol-2-yl)methoxy) phenylamino)-3-morpholino-quinoxaline-5-carbonitrile;

6-(4-(4-chlorobenzyloxy)-3-methoxyphenylamino)-3-morpholinoquinoxaline-5-carbonitrile;

6-(3-methoxy-4-((6-methoxypyridin-3-yl)methoxy)phenylamino)-3-morpholino-quinoxaline-5-carbonitrile;

6-(3-methoxy-4-(pyrazin-2-ylmethoxy)phenylamino)-3-morpholinoquinoxaline-5-carbonitrile;

6-(6-(4-methoxybenzyloxy)pyridin-3-ylamino)-3-morpholinoquinoxaline-5-carbonitrile;

6-(2-fluoro-4-(4-methoxybenzyloxy)phenylamino)-3-morpholinoquinoxaline-5-carbonitrile;

6-(3-methoxy-4-((6-methylpyridin-3-yl)methoxy)phenylamino)-3-morpholino-quinoxaline-5-carbonitrile;

6-(3-methoxy-4-(1-methyl-1H-imidazol-5-yl)methoxy) phenylamino)-3-morpholino-quinoxaline-5-carbonitrile;

6-(3-fluoro-4-(4-methoxybenzyloxy)phenylamino)-3-morpholinoquinoxaline-5-carbonitrile;

6-(3-methoxy-4-(pyridin-2-ylmethoxy)phenylamino)-3-morpholinoquinoxaline-5-carbonitrile;

6-(4-(3,4-dimethoxybenzyloxy)-3-methoxyphenylamino)-3-morpholinoquinoxaline-5-carbonitrile;

6-(3-methoxy-4-((6-methoxypyridin-3-yl)methoxy)phenylamino)-3-(piperazin-1-yl) quinoxaline-5-carbonitrile;

6-((3-methoxy-4-((4-methoxybenzyl)oxy)phenyl) (methyl)amino)-3-morpholino-quinoxaline-5-carbonitrile;

6-((3-methoxy-4-((5-methylisoxazol-3-yl)methoxy)phenyl)amino)-3-morpholino-quinoxaline-5-carbonitrile;

6-((3-methoxy-4-((4-methoxybenzyl)oxy)phenyl) amino)-3-(pyrrolidin-1-yl)quinoxaline-5-carbonitrile;

6-(3-chloro-4-((4-methoxybenzyl)oxy)phenyl)amino)-3-morpholinoquinoxaline-5-carbonitrile;

6-((4-((4-cyanobenzyl)oxy)-3-methoxyphenyl)amino)-3-morpholinoquinoxaline-5-carbonitrile;

6-((4-((3-cyanobenzyl)oxy)-3-methoxyphenyl)amino)-3-morpholinoquinoxaline-5-carbonitrile;

3-(4-(2-hydroxyethyl)piperazin-1-yl)-6-((3-methoxy-4-((4-methoxybenzyl)oxy)phenyl) amino)quinoxaline-5-carbonitrile;

6-((3-methoxy-4-((6-methylpyridin-3-yl)methoxy)phenyl)amino)-3-(piperazin-1-yl) quinoxaline-5-carbonitrile;

1-(8-cyano-7-((3-methoxy-4-((4-methoxybenzyl)oxy) phenyl)amino)quinoxalin-2-yl) piperidin-4-yl acetate;

6-((3-methoxy-4-((6-methoxypyridin-3-yl)methoxy)phenyl)amino)-3-(4-methylpiperidin-1-yl)quinoxaline-5-carbonitrile;

3-(1H-imidazol-1-yl)-6-((3-methoxy-4-((6-methoxypyridin-3-yl)methoxy)phenyl)amino)quinoxaline-5-carbonitrile;

(1-(8-cyano-7-((3-methoxy-4-((4-methoxybenzyl)oxy) phenyl)amino)quinoxalin-2-yl) piperidin-4-yl)methyl acetate;

3-(4-acetylpiperazin-1-yl)-6-((3-methoxy-4-((4-methoxybenzyl)oxy)phenyl)amino) quinoxaline-5-carbonitrile;

6-((3-methoxy-4-((6-(trifluoromethyl)pyridin-3-yl) methoxy)phenyl)amino)-3-morpholinoquinoxaline-5-carbonitrile;

2-(4-(8-cyano-7-((3-methoxy-4-((6-methoxypyridin-3-yl)methoxy)phenyl)amino) quinoxalin-2-yl)piperazin-1-yl)ethyl acetate;

3-(4-(2-hydroxyethyl)piperazin-1-yl)-6-((3-methoxy-4-((6-methoxypyridin-3-yl) methoxy)phenyl)amino)quinoxaline-5-carbonitrile;

6-((3-methoxy-4-((4-methoxybenzyl)oxy)phenyl) amino)-3-((2-morpholinoethyl)amino) quinoxaline-5-carbonitrile;

3-((1-benzylpiperidin-4-yl)amino)-6-((3-methoxy-4-((4-methoxybenzyl)oxy)phenyl) amino)quinoxaline-5-carbonitrile;

6-((4-((3-cyanobenzyl)oxy)-3-methoxyphenyl)amino)-3-(4-methylpiperazin-1-yl) quinoxaline-5-carbonitrile;

6-((3-methoxy-4-((6-methoxypyridin-3-yl)methoxy)phenyl)amino)-3-(pyrrolidin-1-yl) quinoxaline-5-carbonitrile;

3-(4-isopropylpiperazin-1-yl)-6-((3-methoxy-4-((4-methoxybenzyl)oxy)phenyl)amino) quinoxaline-5-carbonitrile;

6-((4-(benzo[d][1,3]dioxol-5-ylmethoxy)-3-methoxyphenyl)amino)-3-morpholino-quinoxaline-5-carbonitrile;

3-(4-(dimethylamino)piperidin-1-yl)-6-((3-methoxy-4-((6-methoxypyridin-3-yl)methoxy)phenyl)amino)quinoxaline-5-carbonitrile;

3-(azetidin-1-yl)-6-((3-methoxy-4-((4-methoxybenzyl) oxy)phenyl)amino)quinoxaline-5-carbonitrile;

6-((4-((3-cyanobenzyl)oxy)-3-methoxyphenyl)amino)-3-(4-(dimethylamino) piperidin-1-yl)quinoxaline-5-carbonitrile;

3-(4-(dimethylamino)piperidin-1-yl)-6-((4-((3-fluoro-4-methoxybenzyl)oxy)-3-methoxyphenyl)amino)quinoxaline-5-carbonitrile;

3-(azetidin-1-yl)-6-((3-methoxy-4-((6-methoxypyridin-3-yl)methoxy)phenyl)amino) quinoxaline-5-carbonitrile;

3-(azetidin-1-yl)-6-((4-((3-cyanobenzyl)oxy)-3-methoxyphenyl)amino)quinoxaline-5-carbonitrile;

6-((4-(benzyloxy)-3-methoxyphenyl)amino)-3-morpholinoquinoxaline-5-carbonitrile;

3-(4-(dimethylamino)piperidin-1-yl)-6-((4-((3-fluorobenzyl)oxy)-3-methoxyphenyl) amino)quinoxaline-5-carbonitrile;

6-((3-methoxy-4-((4-methoxybenzyl)oxy)phenyl) amino)-3-(piperazin-1-yl)quinoxaline-5-carbonitrile;

6-((4-((3-fluorobenzyl)oxy)-3-methoxyphenyl)amino)-3-morpholinoquinoxaline-5-carbonitrile;

6-(3-methoxy-4-(prop-2-yn-1-yloxy)phenyl)amino)-3-morpholinoquinoxaline-5-carbonitrile;

6-((4-((3-fluoro-4-methoxybenzyl)oxy)-3-methoxyphenyl)amino)-3-morpholino-quinoxaline-5-carbonitrile;

6-((4-((2-fluoro-4-methoxybenzyl)oxy)-3-methoxyphenyl)amino)-3-morpholino-quinoxaline-5-carbonitrile;

6-((3-methoxy-4-((6-methoxypyridin-3-yl)methoxy)phenyl)amino)-3-(4-methyl-piperazin-1-yl)quinoxaline-5-carbonitrile;

6-((4-((3-cyano-4-methoxybenzyl)oxy)-3-methoxyphenyl)amino)-3-morpholino-quinoxaline-5-carbonitrile;

6-((3-methoxy-4-((6-methoxypyridin-3-yl)methoxy)phenyl)amino)-3-(4-(2-methoxyethyl)piperazin-1-yl)quinoxaline-5-carbonitrile;

6-((3-methoxy-4-((6-propylpyridin-3-yl)methoxy)phenyl)amino)-3-morpholino-quinoxaline-5-carbonitrile;

6-((4-((3,4-difluorobenzyl)oxy)-3-methoxyphenyl) amino)-3-morpholinoquinoxaline-5-carbonitrile;

6-((3-methoxy-4-((6-methylpyridin-3-yl)methoxy)phenyl)amino)-3-(4-(2-methoxyethyl) piperazin-1-yl)quinoxaline-5-carbonitrile;

6-((4-((6-ethylpyridin-3-yl)methoxy)-3-methoxyphenyl) amino)-3-morpholino-quinoxaline-5-carbonitrile;

6-((3-methoxy-4-((6-methoxypyridin-3-yl)methoxy)phenyl)amino)-3-(4-morpholino-piperidin-1-yl)quinoxaline-5-carbonitrile;
6-((4-((6-isopropylpyridin-3-yl)methoxy)-3-methoxyphenyl)amino)-3-morpholino-quinoxaline-5-carbonitrile;
6-((4-((6-(dimethylamino)pyridin-3-yl)methoxy)-3-methoxyphenyl)amino)-3-morpholinoquinoxaline-5-carbonitrile;
6-((3-methoxy-4-((1-methyl-1H-pyrazol-4-yl)methoxy) phenyl)amino)-3-morpholino-quinoxaline-5-carbonitrile;
N-(3-methoxy-4-((4-methoxybenzyl)oxy)phenyl)-3-(prop-1-en-2-yl)quinoxalin-6-amine;
6-((3-methoxy-4-((6-(methoxymethyl)pyridin-3-yl) methoxy)phenyl)amino)-3-morpholinoquinoxaline-5-carbonitrile;
6-((3-methoxy-4-((4-methoxybenzyl)oxy)phenyl) amino)-3-(prop-1-en-2-yl) quinoxaline-5-carbonitrile;
3-isopropyl-6-((3-methoxy-4-((4-methoxybenzyl)oxy) phenyl)amino)quinoxaline-5-carbonitrile;
6-((4-((6-(fluoromethyl)pyridin-3-yl)methoxy)-3-methoxyphenyl)amino)-3-morpholino-quinoxaline-5-carbonitrile;
6-((4-((6-(difluoromethyl)pyridin-3-yl)methoxy)-3-methoxyphenyl)amino)-3-morpholinoquinoxaline-5-carbonitrile;
6-((4-((6-ethoxypyridin-3-yl)methoxy)-3-methoxyphenyl)amino)-3-morpholino-quinoxaline-5-carbonitrile;
3-(3,6-dihydro-2H-pyran-4-yl)-6-((3-methoxy-4-((6-methylpyridin-3-yl)methoxy)phenyl)amino)quinoxaline-5-carbonitrile;
6-((3-methoxy-4-((6-methylpyridin-3-yl)methoxy)phenyl)amino)-3-(tetrahydro-2H-pyran-4-yl)quinoxaline-5-carbonitrile;
6-((4-((6-((dimethylamino)methyl)pyridin-3-yl) methoxy)-3-methoxyphenyl)amino)-3-morpholinoquinoxaline-5-carbonitrile;
6-((3-methoxy-4-((1-ethyl-1H-pyrazol-4-yl)methoxy) phenyl)amino)-3-morpholino-quinoxaline-5-carbonitrile;
6-((3-methoxy-4-((1-propyl-1H-pyrazol-4-yl)methoxy) phenyl)amino)-3-morpholino-quinoxaline-5-carbonitrile;
3-(4-cyclopropylpiperazin-1-yl)-6-((3-methoxy-4-((6-methoxypyridin-3-yl)methoxy) phenyl)amino)quinoxaline-5-carbonitrile;
3-isopropoxy-6-((3-methoxy-4-((6-methoxypyridin-3-yl) methoxy)phenyl)amino) quinoxaline-5-carbonitrile;
6-((4-((6-cyclopropylpyridin-3-yl)methoxy)-3-methoxyphenyl)amino)-3-morpholino-quinoxaline-5-carbonitrile;
6-((4-(furan-3-ylmethoxy)-3-methoxyphenyl)amino)-3-morpholinoquinoxaline-5-carbonitrile;
6-((4-(furan-2-ylmethoxy)-3-methoxyphenyl)amino)-3-morpholinoquinoxaline-5-carbonitrile;
6-((3-methoxy-4-((tetrahydrofuran-2-yl)methoxy)phenyl)amino)-3-morpholino-quinoxaline-5-carbonitrile;
6-((3-methoxy-4-((5-methylthiophen-2-yl)methoxy)phenyl)amino)-3-morpholino-quinoxaline-5-carbonitrile;
6-((3-methoxy-4-((5-(methoxymethyl)pyridin-2-yl) methoxy)phenyl)amino)-3-morpholinoquinoxaline-5-carbonitrile;
6-((3-methoxy-4-(thiophen-3-ylmethoxy)phenyl)amino)-3-morpholinoquinoxaline-5-carbonitrile;
6-((3-methoxy-4-(thiophen-2-ylmethoxy)phenyl)amino)-3-morpholinoquinoxaline-5-carbonitrile;
6-((3-methoxy-4-((2-methylpyrimidin-5-yl)methoxy) phenyl)amino)-3-morpholino-quinoxaline-5-carbonitrile;
6-((3-methoxy-4-((6-methylpyridin-3-yl)methoxy)phenyl)(methyl)amino)-3-morpholino-quinoxaline-5-carbonitrile;
6-((4-((6-cyclopropylpyridin-3-yl)methoxy)-3-methoxyphenyl)(methyl)amino)-3-morpholinoquinoxaline-5-carbonitrile;
6-((4-((1-(2-fluoroethyl)-1H-pyrazol-4-yl)methoxy)-3-methoxyphenyl)amino)-3-morpholinoquinoxaline-5-carbonitrile;
6-((3-methoxy-4-((5-methoxypyridin-2-yl)methoxy)phenyl)amino)-3-morpholino-quinoxaline-5-carbonitrile;
3-(dimethylamino)-6-((3-methoxy-4-((6-methylpyridin-3-yl)methoxy)phenyl)amino) quinoxaline-5-carbonitrile;
6-((4-((1-cyclopropyl-1H-pyrazol-4-yl)methoxy)-3-methoxyphenyl)amino)-3-morpholinoquinoxaline-5-carbonitrile;
6-((3-methoxy-4-((6-methylpyridin-3-yl)methoxy)phenyl)amino)-3-morpholinoquinoxaline-5-carboxamide;
3-(3-(dimethylamino)azetidin-1-yl)-6-((3-methoxy-4-((6-methylpyridin-3-yl)methoxy) phenyl)amino)quinoxaline-5-carbonitrile;
3-(dimethylamino)-6-((3-methoxy-4-((6-methoxypyridin-3-yl)methoxy)phenyl)amino) quinoxaline-5-carbonitrile;
3-(3-methoxy-3-methylazetidin-1-yl)-6-((3-methoxy-4-((6-methylpyridin-3-yl)methoxy) phenyl)amino)quinoxaline-5-carbonitrile;
6-((4-((3-cyano-4-methoxybenzyl)oxy)-3-methoxyphenyl)amino)-3-(dimethylamino) quinoxaline-5-carbonitrile;
6-((4-((3-cyano-4-methoxybenzyl)oxy)-3-methoxyphenyl)amino)-3-methoxyquinoxaline-5-carbonitrile;
6-((4-((1-(cyclopropylmethyl)-1H-pyrazol-4-yl) methoxy)-3-methoxyphenyl)amino)-3-morpholinoquinoxaline-5-carbonitrile;
3-morpholino-6-((6-((4-(trifluoromethyl)benzyl)amino) pyridin-3-yl)amino)quinoxaline-5-carbonitrile;
6-((5-methoxy-6-((6-methylpyridin-3-yl)methoxy)pyridin-3-yl)amino)-3-morpholinoquinoxaline-5-carbonitrile;
6-((5-methoxy-6-((6-methoxypyridin-3-yl)methoxy)pyridin-3-yl)amino)-3-morpholinoquinoxaline-5-carbonitrile;
3-((2S,6R)-2,6-dimethylmorpholino)-6-((3-methoxy-4-((6-methylpyridin-3-yl)methoxy) phenyl)amino)quinoxaline-5-carbonitrile; or
6-((3-methoxy-4-((6-methyl-1-($\lambda^1$-oxidaneyl)-1$\lambda^4$-pyridin-3-yl)methoxy)phenyl)amino)-3-morpholinoquinoxaline-5-carbonitrile.

10. A pharmaceutical composition comprising the compound according to claim 1, a stereoisomer thereof, or a pharmaceutically acceptable salt thereof, and a pharmaceutically acceptable diluent or carrier.

11. A method for treating a disease or disorder mediated by CSF-1R and/or KIT kinase, comprising administering to a subject in need thereof a therapeutically effective amount of the pharmaceutical composition of claim 10, wherein the disease or disorder is selected from the group consisting of multiple myeloma, acute myeloid leukemia (AML), chronic myeloid leukemia (CML), prostate cancer, breast cancer, ovarian cancer, melanoma, glioblastoma multiforme, giant cell tumor of bone, non-small-cell lung cancers, giant cell tumor of the tendon sheath, metastasis of tumors to other tissues, myelofibrosis, pigmented villonodular synovitis, and gastrointestinal stromal tumor.

12. The compound of claim 2, wherein X is NH.
13. The compound of claim 3, wherein X is NH.
14. The compound of claim 4, wherein X is NH.
15. The compound of claim 5, wherein X is NH.
16. The compound of claim 6, wherein X is NH.
17. The compound of claim 2, wherein Z is —O—.

* * * * *